US012178855B2

(12) United States Patent
Bhat et al.

(10) Patent No.: US 12,178,855 B2
(45) Date of Patent: Dec. 31, 2024

(54) COMPOSITIONS AND METHODS FOR FACILITATING DELIVERY OF SYNTHETIC NUCLEIC ACIDS TO CELLS

(71) Applicant: Translate Bio MA, Inc., Lexington, MA (US)

(72) Inventors: Balkrishen Bhat, Carlsbad, CA (US); Jia Tay, Acton, MA (US); Saswata Karmakar, Acton, MA (US); Nelson Chau, Needham, MA (US)

(73) Assignee: Translate Bio MA, Inc., Lexington, MA (US)

( * ) Notice: Subject to any disclaimer, the term of this patent is extended or adjusted under 35 U.S.C. 154(b) by 1209 days.

(21) Appl. No.: 16/961,187

(22) PCT Filed: Jan. 10, 2019

(86) PCT No.: PCT/US2019/013070
§ 371 (c)(1),
(2) Date: Jul. 9, 2020

(87) PCT Pub. No.: WO2019/140102
PCT Pub. Date: Jul. 18, 2019

(65) Prior Publication Data
US 2021/0052706 A1 Feb. 25, 2021

Related U.S. Application Data

(60) Provisional application No. 62/615,577, filed on Jan. 10, 2018.

(51) Int. Cl.
*C07H 21/04* (2006.01)
*A61K 38/45* (2006.01)
*A61K 47/54* (2017.01)
*C12N 15/113* (2010.01)

(52) U.S. Cl.
CPC ............ *A61K 38/45* (2013.01); *A61K 47/549* (2017.08); *C12N 15/113* (2013.01); *C12N 2310/3231* (2013.01); *C12N 2310/3519* (2013.01); *C12Y 201/03003* (2013.01)

(58) Field of Classification Search
None
See application file for complete search history.

(56) References Cited

U.S. PATENT DOCUMENTS

| 4,762,779 | A | 8/1988 | Snitman |
| 4,789,737 | A | 12/1988 | Miyoshi et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,845,205 | A | 7/1989 | Huynh Dinh et al. |
| 4,876,335 | A | 10/1989 | Yamane et al. |
| 4,904,582 | A | 2/1990 | Tullis |
| 4,948,882 | A | 8/1990 | Ruth |
| 4,958,013 | A | 9/1990 | Letsinger |
| 5,013,830 | A | 5/1991 | Ohtsuka et al. |
| 5,023,243 | A | 6/1991 | Tullis |
| 5,034,506 | A | 7/1991 | Summerton et al. |
| 5,082,830 | A | 1/1992 | Brakel et al. |
| 5,109,124 | A | 4/1992 | Ramachandran et al. |
| 5,112,963 | A | 5/1992 | Pieles et al. |
| 5,118,802 | A | 6/1992 | Smith et al. |
| 5,130,302 | A | 7/1992 | Spielvogel et al. |
| 5,134,066 | A | 7/1992 | Rogers et al. |
| 5,138,045 | A | 8/1992 | Cook et al. |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,185,444 | A | 2/1993 | Summerton et al. |
| 5,188,897 | A | 2/1993 | Suhadolnik et al. |
| 5,214,134 | A | 5/1993 | Weis et al. |
| 5,214,136 | A | 5/1993 | Lin et al. |
| 5,216,141 | A | 6/1993 | Benner |
| 5,218,105 | A | 6/1993 | Cook et al. |
| 5,220,007 | A | 6/1993 | Pederson et al. |
| 5,235,033 | A | 8/1993 | Summerton et al. |
| 5,245,022 | A | 9/1993 | Weis et al. |
| 5,254,469 | A | 10/1993 | Warren, III et al. |
| 5,256,775 | A | 10/1993 | Froehler |
| 5,258,506 | A | 11/1993 | Urdea et al. |
| 5,262,536 | A | 11/1993 | Hobbs, Jr. |
| 5,264,423 | A | 11/1993 | Cohen et al. |

(Continued)

FOREIGN PATENT DOCUMENTS

| WO | WO 1999/67378 A1 | 12/1999 |
| WO | WO 2005/042777 A2 | 5/2005 |
| WO | WO 2007/112753 A2 | 10/2007 |
| WO | WO 2007/112754 A2 | 10/2007 |
| WO | WO 2009/043353 A2 | 4/2009 |
| WO | WO 2011/012316 A2 | 2/2011 |
| WO | WO 2013/166121 A1 | 11/2013 |
| WO | WO 2014/172698 A1 | 10/2014 |
| WO | WO 2014/179620 A1 | 11/2014 |
| WO | WO 2015/006740 A2 | 1/2015 |
| WO | WO 2016/091391 A1 | 6/2016 |
| WO | WO 2016/107877 A1 | 7/2016 |

(Continued)

OTHER PUBLICATIONS

Extended European Search Report for Application No. EP 17828273. 7, mailed Feb. 28, 2020.

(Continued)

*Primary Examiner* — Kimberly Chong
(74) *Attorney, Agent, or Firm* — Wolf, Greenfield & Sacks, P.C.

(57) ABSTRACT

Provided herein are compositions and methods for facilitating or enhancing delivery of nucleic acids, such as synthetic mRNAs, into cells or tissues. Such compositions and methods may include use of a targeting moiety-conjugated, such as an N-acetylgalactosamine (GalNAc)-conjugated, oligonucleotide to facilitate or enhance delivery.

21 Claims, 17 Drawing Sheets
Specification includes a Sequence Listing.

(56) References Cited

U.S. PATENT DOCUMENTS

| | | |
|---|---|---|
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer, Jr. et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,633,360 A | 5/1997 | Bischofberger et al. |
| 5,652,355 A | 7/1997 | Metelev et al. |
| 5,652,356 A | 7/1997 | Agrawal |
| 5,663,312 A | 9/1997 | Chaturvedula |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,922 A | 12/1997 | Cook |
| 5,750,692 A | 5/1998 | Cook et al. |
| 6,287,860 B1 | 9/2001 | Monia et al. |
| 7,314,923 B2 | 1/2008 | Kaneko et al. |
| 7,335,765 B2 | 2/2008 | Kaneko et al. |
| 7,399,845 B2 | 7/2008 | Seth et al. |
| 7,569,686 B1 | 8/2009 | Bhat et al. |
| 7,741,457 B2 | 6/2010 | Seth et al. |
| 7,816,333 B2 | 10/2010 | Kaneko et al. |
| 7,951,926 B2 | 5/2011 | Morvan et al. |
| 8,022,193 B2 | 9/2011 | Seth et al. |
| 8,828,956 B2 | 9/2014 | Manoharan et al. |
| 8,962,580 B2 | 2/2015 | Manoharan et al. |
| 9,061,021 B2 | 6/2015 | Guild et al. |
| 9,181,549 B2 | 11/2015 | Prakash et al. |
| 9,198,972 B2 | 12/2015 | Manoharan et al. |
| 11,253,601 B2 | 2/2022 | Bhat et al. |
| 2007/0068265 A1 | 3/2007 | Watanabe |
| 2011/0009471 A1 | 1/2011 | Kaneko et al. |
| 2012/0071540 A1 | 3/2012 | Lu et al. |
| 2012/0136042 A1 | 5/2012 | Manoharan et al. |
| 2015/0184195 A1 | 7/2015 | Thess et al. |
| 2015/0218554 A1 | 8/2015 | Thess |
| 2015/0299695 A1 | 10/2015 | Uhlmann et al. |
| 2015/0320847 A1 | 11/2015 | Thess et al. |
| 2016/0058842 A1 | 3/2016 | Turecek et al. |
| 2017/0009244 A1 | 1/2017 | Sahin et al. |
| 2017/0029847 A1 | 2/2017 | Thess |
| 2017/0056528 A1 | 3/2017 | De Fougerolles et al. |
| 2017/0252461 A1 | 9/2017 | Chakraborty et al. |
| 2017/0349896 A1* | 12/2017 | Albaek ............ A61P 43/00 |
| 2018/0055869 A1* | 3/2018 | Ozsolak ........... A61K 31/7105 |
| 2019/0224326 A1 | 7/2019 | Bhat et al. |
| 2022/0218829 A1 | 7/2022 | Bhat et al. |

FOREIGN PATENT DOCUMENTS

| WO | WO 2016/130943 A1 | 8/2016 |
| WO | WO 2016/205410 A2 | 12/2016 |
| WO | WO 2017/001554 A1 | 1/2017 |
| WO | WO 2017/059902 A1 | 4/2017 |
| WO | WO 2017/075038 A1 | 5/2017 |
| WO | WO 2017/153936 A1 | 9/2017 |
| WO | WO 2017/167910 A1 | 10/2017 |

OTHER PUBLICATIONS

International Search Report and Written Opinion for International Appliction No. PCT/US2017/041469, mailed Dec. 12, 2017.

International Preliminary Report on Patentability for International Application No. PCT/US2017/041469, mailed Jan. 24, 2019.

International Search Report and Written Opinion for International Appliction No. PCT/US2019/013070, mailed May 1, 2019.

International Preliminary Report on Patentability for International Application No. PCT/US2019/013070, mailed Jul. 23, 2020.

Bejjani et al., N-tritylprolinal: an efficient building block for the stereoselective synthesis of proline-derived amino alcohols. J Org Chem. 2003;68(25):9747-9752. doi:10.1021/jo034976g.

Braasch et al., Novel antisense and peptide nucleic acid strategies for controlling gene expression. Biochemistry. 2002;41(14):4503-4510. doi:10.1021/bi0122112.

Brown et al., Conjugation of an oligonucleotide to Tat, a cell-penetrating peptide, via click chemistry. Tetrahedron Letters. Sep. 22, 2010:51(38): 5032-5034.

(56) References Cited

OTHER PUBLICATIONS

Crooke et al., Pharmacokinetic properties of several novel oligonucleotide analogs in mice. J Pharmacol Exp Ther. 1996;277(2):923-937.
De Mesmaeker et al., Antisense Oligonucleotides. Acc. Chem. Res. 1995;28:366-74.
Dohmen et al., Defined Folate-PEG-siRNA Conjugates for Receptor-specific Gene Silencing. Mol Ther Nucleic Acids. Jan. 2012; 1(1): e7. EPub Jan. 31, 2012. doi: 10.1038/mtna.2011.10. 6 pages.
Efthymiou et al., Chemical architecture and applications of nucleic acid derivatives containing 1,2,3-triazole functionalities synthesized via click chemistry. Molecules. Oct. 26, 2012;17(11):12665-703. doi: 10.3390/molecules171112665.
Englishsch et al.,Angewandle Chemie, International Edition, 1991, 30, p. 613.
Gabeyehu et al., Novel biotinylated nucleotide—analogs for labeling and colorimetric detection of DNA. Nucleic Acids Res. 1987;15(11):4513-4534. doi:10.1093/nar/15.11.4513.
Gooding et al., Oligonucleotide conjugates—Candidates for gene silencing therapeutics. Eur J Pharm Biopharm. Oct. 2016;107:321-40. doi: 10.1016/j.ejpb.2016.07.024. Epub Aug. 10, 2016.
He et al., Conjugation and Evaluation of Triazole-Linked Single Guide RNA for CRISPR-Cas9 Gene Editing. Chembiochem. Oct. 4, 2016;17(19):1809-1812. doi: 10.1002/cbic.201600320. Epub Aug. 19, 2016.
Heasman, Morpholino oligos: making sense of antisense?. Dev Biol. 2002;243(2):209-214. doi:10.1006/dbio.2001.0565.
Horie et al., Synthesis and properties of ENA oligonucleotides targeted to human telomerase RNA subunit. Nucleic Acids Symp Ser (Oxf). 2005;(49):171-172. doi:10.1093/nass/49.1.171.
Huang, Preclinical and Clinical Advances of GalNAc-Decorated Nucleic Acid Therapeutics. Mol Ther Nucleic Acids. Mar. 17, 2017;6:116-132. doi: 10.1016/j.omtn.2016.12.003. Epub Dec. 10, 2016.
Iversen, Phosphorodiamidate morpholino oligomers: favorable properties for sequence-specific gene inactivation. Curr Opin Mol Ther. 2001;3(3):235-238.
Jayaprakash et al., Non-nucleoside building blocks for copper-assisted and copper-free click chemistry for the efficient synthesis of RNA conjugates. Org Lett. Dec. 3, 2010;12(23):5410-3. doi: 10.1021/ol102205j. Epub Nov. 4, 2010.
Kabanov et al., A new class of antivirals: antisense oligonucleotides combined with a hydrophobic substituent effectively inhibit influenza virus reproduction and synthesis of virus-specific proteins in MDCK cells. FEBS Lett. 1990;259(2):327-330. doi:10.1016/0014-5793(90)80039-1.
Kasuya et al., In vivo delivery of bionanocapsules displaying Phaseolus vulgaris agglutinin-L4 isolectin to malignant tumors overexpressing N-acetylglucosaminyltransferase V. Hum Gene Ther. 2008;19(9):887-895. doi:10.1089/hum.2008.037.
Khorev et al., Trivalent, Gal/GalNAc-containing ligands designed for the asialoglycoprotein receptor. Bioorg Med Chem. 2008;16(9):5216-5231. doi:10.1016/j.bmc.2008.03.017.
Kikkeri et al., Facile synthesis of size dependent Ru(II)-carbohydrate dendrimers via click chemistry. Chem Commun (Camb). 2010;46(13):2197-2199. doi:10.1039/b925113h.
Koizumi et al., ENA oligonucleotides as therapeutics. Curr Opin Mol Ther. 2006;8(2):144-149.
Kornberg., DNA Replication. W. H. Freeman & Co., San Francisco, 1980, pp. 75-77.
Kroschwitz, The Concise Encyclopedia of Polymer Science And Engineering, pp. 858-859, Kroschwitz, ed. John Wiley & Sons, 199.
Lacerra et al., Restoration of hemoglobin A synthesis in erythroid cells from peripheral blood of thalassemic patients. Proc Natl Acad Sci U S A. 2000;97(17):9591-9596. doi:10.1073/pnas.97.17.9591.
Letsinger et al., Cholesteryl-conjugated oligonucleotides: synthesis, properties, and activity as inhibitors of replication of human immunodeficiency virus in cell culture. Proc Natl Acad Sci U S A. 1989;86(17):6553-6556. doi:10.1073/pnas.86.17.6553.
Lok et al., Potent gene-specific inhibitory properties of mixed-backbone antisense oligonucleotides comprised of 2'-deoxy-2'-fluoro-D-arabinose and 2'-deoxyribose nucleotides. Biochemistry. 2002;41(10):3457-3467. doi:10.1021/bi0115075.
Manoharan et al. Cholic acid-oligonucleotide conjugates for antisense applications. Bioorg. Med. Chem. Let. Apr. 21, 1994;4(8):1053-1060.
Manoharan et al. Introduction of a lipophilic thioether tether in the minor groove of nucleic acids for antisense applications. Bioorg. Med. Chem. Lett. 1993;3(12):2765-2770.
Manoharan et al. Oligonucleotide Conjugates: Alteration of the Pharmacokinetic Properties of Antisense Agents. Nucleosides & Nucleotides, 1995;14(3-5):969-973.
Manoharan et al., Chemical modifications to improve uptake and bioavailability of antisense oligonucleotides. Ann N Y Acad Sci. 1992;660:306-309. doi:10.1111/j.1749-6632.1992.tb21095.x.
Manoharan et al., Lipidic nucleic acids. Tetrahedron Lett. May 22, 1995;36(21):3651-3654.
Matsuda et al., siRNA conjugates carrying sequentially assembled trivalent N-acetylgalactosamine linked through nucleosides elicit robust gene silencing in vivo in hepatocytes. ACS Chem Biol. May 15, 2015;10(5):1181-7. doi: 10.1021/cb501028c.
Min et al., Oligonucleotides comprised of alternating 2'-deoxy-2'-fluoro-beta-D-arabinonucleosides and D-2'-deoxyribonucleosides (2'F-ANA/DNA 'altimers') induce efficient RNA cleavage mediated by RNase H. Bioorg Med Chem Lett. 2002;12(18):2651-2654. doi:10.1016/s0960-894x(02)00439-0.
Mishra et al., Improved leishmanicidal effect of phosphorotioate antisense oligonucleotides by LDL-mediated delivery. Biochim Biophys Acta. 1995;1264(2):229-237. doi:10.1016/0167-4781(95)00145-7.
Morcos, Achieving efficient delivery of morpholino oligos in cultured cells. Genesis. 2001;30(3):94-102. doi:10.1002/gene.1039.
Morita et al., 2'-O,4'-C-ethylene-bridged nucleic acids (ENA) with nuclease-resistance and high affinity for RNA. Nucleic Acids Res Suppl. 2001;(1):241-242. doi:10.1093/nass/1.1.241.
Nair et al., Multivalent N-acetylgalactosamine-conjugated siRNA localizes in hepatocytes and elicits robust RNAi-mediated gene silencing. J Am Chem Soc. Dec. 10, 2014;136(49):16958-61. doi: 10.1021/ja505986a. Epub Dec. 1, 2014.
Nasevisicius et al., Effective targeted gene 'knockdown' in zebrafish. Nat Genet. 2000;26(2):216-220. doi:10.1038/79951.
Nielsen et al., Sequence-selective recognition of DNA by strand displacement with a thymine-substituted polyamide. Science. 1991;254(5037):1497-1500. doi:10.1126/science.1962210.
Oberhauser et al., Effective incorporation of 2'-O-methyl-oligoribonucleotides into liposomes and enhanced cell association through modification with thiocholesterol. Nucleic Acids Res. 1992;20(3):533-538. doi:10.1093/nar/20.3.533.
Pourceau et al., Synthesis of mannose and galactose oligonucleotide conjugates by bi-click chemistry. J Org Chem. 2009;74(3):1218-1222. doi:10.1021/jo802536q.
Sanghvi, Chapter 15, Antisense Research and Applications, pp. 289-302, Crooke, and Lebleu, eds., CRC Press, 1993. Certain.
Shea et al., Synthesis, hybridization properties and antiviral activity of lipid-oligodeoxynucleotide conjugates. Nucleic Acids Res. 1990;18(13):3777-3783. doi:10.1093/nar/18.13.3777.
Sliedregt et al., Design and synthesis of novel amphiphilic dendritic galactosides for selective targeting of liposomes to the hepatic asialoglycoprotein receptor. J Med Chem. 1999;42(4):609-618. doi:10.1021/jm981078h.
Surono et al., Chimeric RNA/ethylene-bridged nucleic acids promote dystrophin expression in myocytes of duchenne muscular dystrophy by inducing skipping of the nonsense mutation-encoding exon. Hum Gene Ther. 2004;15(8):749-757. doi:10.1089/1043034041648444.
Svinarchuk et al., Inhibition of HIV proliferation in MT-4 cells by antisense oligonucleotide conjugated to lipophilic groups. Biochimie. 1993;75(1-2):49-54. doi:10.1016/0300-9084(93)90024-m.
Wang et al., Cyclohexene Nucleic Acids (CeNA):? Serum Stable Oligonucleotides that Activate RNase H and Increase Duplex Stability with Complementary RNA. J Am. Chem. Soc. 2000, 122, 8595-8602.

(56) References Cited

OTHER PUBLICATIONS

Wang et al., In vitro evaluation of novel antisense oligonucleotides is predictive of in vivo exon skipping activity for Duchenne muscular dystrophy. J Gene Med. 2010;12(4):354-364. doi:10.1002/jgm.1446.

Winkler et al., Oligonucleotide conjugates for therapeutic applications. Ther Deliv. 2013;4(7):791-809. doi:10.4155/tde.13.47.

Wu et al., Improving the antigenicity of sTn antigen by modification of its sialic acid residue for development of glycoconjugate cancer vaccines. Bioconjug Chem. 2006;17(6):1537-1544. doi:10.1021/bc060103s.

Yamada et al., Versatile Site-Specific Conjugation of Small Molecules to siRNA Using Click Chemistry. J. Org. Chem. 2011:76(5); 1198-1211.

EP 17828273.7, Feb. 28, 2020, Extended European Search Report.

PCT/US2017/041469, Dec. 12, 2017, International Search Report and Written Opinion.

PCT/US2017/041469, Jan. 24, 2019, International Preliminary Report on Patentability.

PCT/US2019/013070, May 1, 2019, International Search Report and Written Opinion.

PCT/US2019/013070, Jul. 23, 2020, International Preliminary Report on Patentability.

Extended European Search Report mailed Sep. 23, 2021 for European Application No. EP 19738098.3.

\* cited by examiner

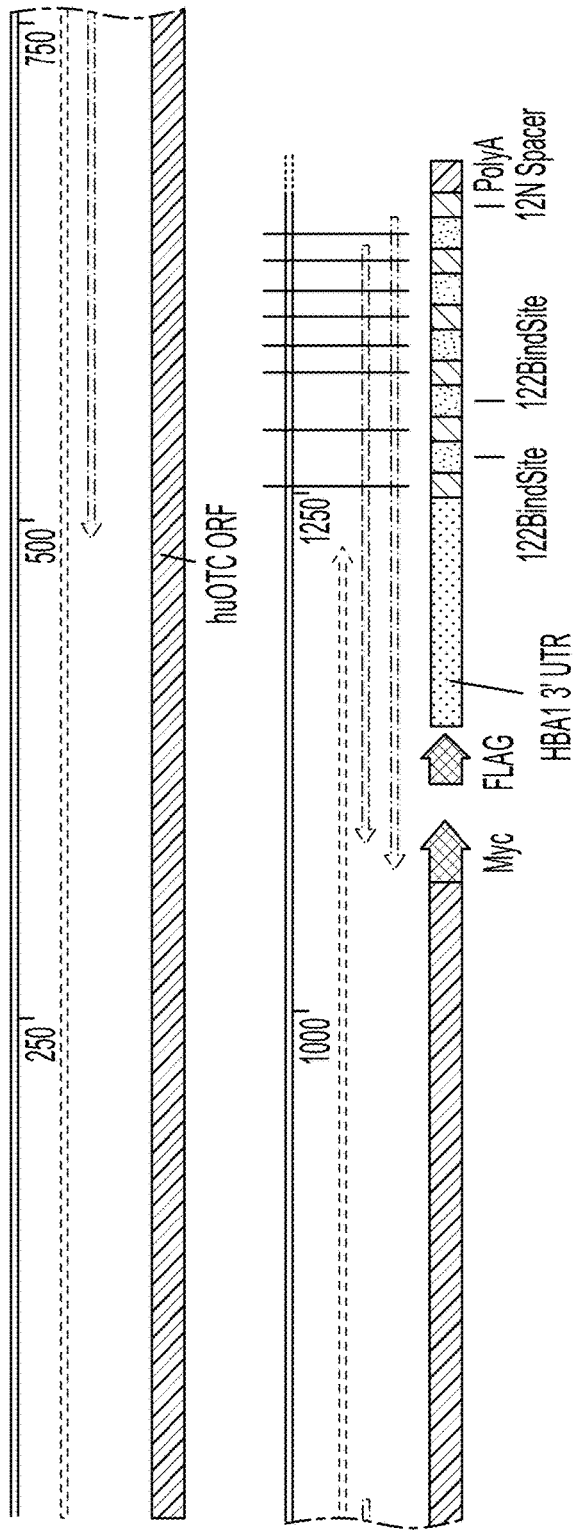
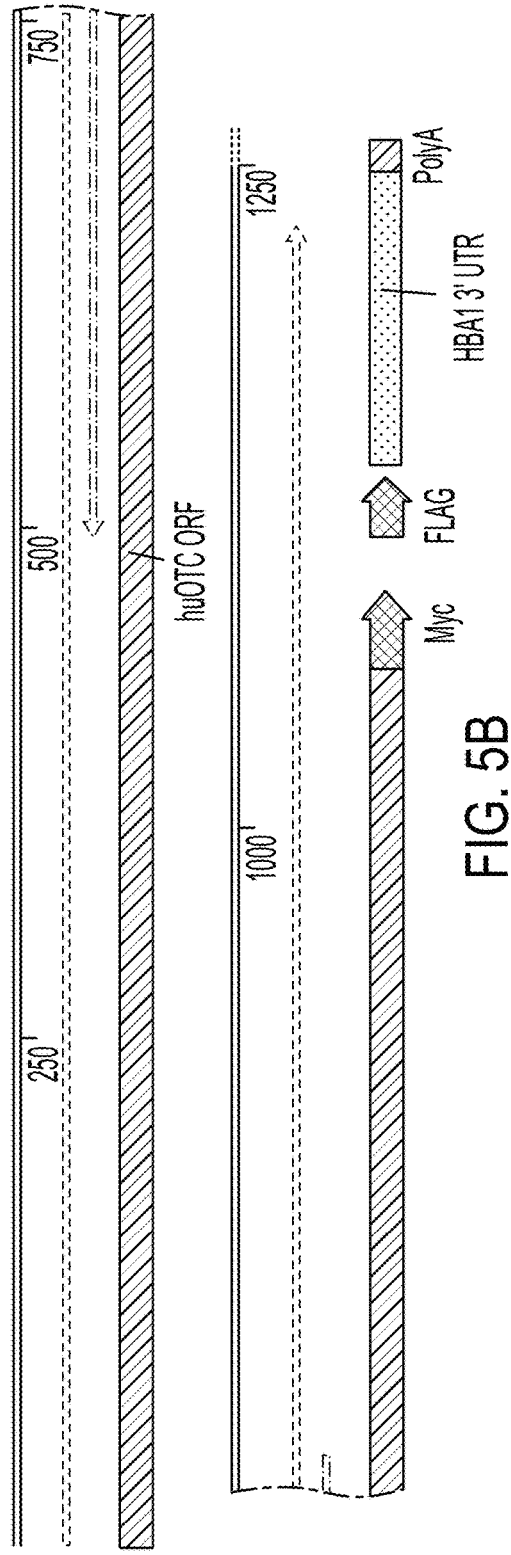
FIG. 5A
FIG. 5B

FIG. 9B

COMPOSITIONS AND METHODS FOR FACILITATING DELIVERY OF SYNTHETIC NUCLEIC ACIDS TO CELLS

CROSS-REFERENCE TO RELATED APPLICATIONS

This application is a national stage filing under 35 U.S.C. § 371 of International Patent Application Serial No. PCT/US2019/013070, filed Jan. 10, 2019, which claims the benefit under 35 U.S.C. § 119(e) of U.S. Provisional Application No. 62/615,577 filed on Jan. 10, 2018, the contents of each of which are incorporated herein by reference in their entirety.

FIELD OF THE INVENTION

The invention relates in part to compositions and methods for modulating protein expression.

BACKGROUND OF THE INVENTION

A considerable portion of human diseases can be treated by selectively altering protein expression by modulating the RNA of the protein-associated transcription units (messenger RNA, noncoding RNAs, protein-coding RNAs or other regulatory coding or noncoding genomic regions). Methods for inhibiting the expression of genes are known in the art and include, for example, antisense-, RNAi- and miRNA-mediated approaches. Such methods may involve enhancing or blocking translation of mRNAs or causing degradation of target RNAs. However, limited approaches are available for delivering nucleic acid therapeutics for such treatments.

SUMMARY OF THE INVENTION

Aspects of the disclosure relate to compositions and methods of facilitating delivery of nucleic acids to cells, such as delivery to liver cells. In some embodiments, it is expected that an oligonucleotide covalently linked to one or more targeting moieties, such as a GalNAc-modified oligonucleotide, will facilitate or enhance delivery of other nucleic acids associated with, e.g., complexed with or based-paired with, the oligonucleotide. In some aspects, it has been found that conjugation of a N-acetylgalactosamine (GalNAc) moiety to an oligonucleotide enhances delivery to liver cells in vivo. In some embodiments, it is expected that an oligonucleotide covalently linked to one or more targeting moieties, such as a GalNAc-conjugated oligonucleotide, will facilitate or enhance delivery of synthetic mRNAs that contain one or more binding sites for the oligonucleotide.

In some aspects, the disclosure provides a composition comprising: an oligonucleotide of up to 50 nucleotides in length covalently linked to a targeting moiety; and a synthetic RNA comprising at least one binding region that is complementary to a contiguous stretch of at least 5 nucleotides of the oligonucleotide.

In some embodiments, the synthetic RNA comprises at least two copies of the binding region. In some embodiments, the synthetic RNA comprises at least three copies of the binding region. In some embodiments, the synthetic RNA comprises at least four copies of the binding region. In some embodiments, the synthetic RNA comprises at least five copies of the binding region. In some embodiments, the synthetic RNA comprises at least six copies of the binding region. In some embodiments, the synthetic RNA comprises at least seven copies of the binding region.

In some embodiments, the copies of the binding region are separated from one another by a spacer region comprising at least one nucleotide. In some embodiments, each spacer region between each copy of the binding region is independently between 3 and 24 nucleotides in length. In some embodiments, each spacer region between each copy of the binding region is independently 3, 6, 12 or 24 nucleotides in length.

In some embodiments, the synthetic RNA is a synthetic mRNA. In some embodiments, the at least one binding region is located in an untranslated region (UTR) of the synthetic mRNA. In some embodiments, the UTR is a 5' UTR. In some embodiments, the UTR is a 3' UTR. In some embodiments, the at least one binding region is located in the polyA tail of the synthetic mRNA.

In some embodiments, the synthetic RNA is a guide RNA.
In some embodiments, the synthetic RNA is a siRNA.
In some embodiments, the binding region comprises a microRNA sequence or a portion thereof. In some embodiments, the binding region comprises a sequence that is not present in an endogenous human mRNA. In some embodiments, the binding region comprises a sequence in a non-coding portion of a synthetic mRNA, such as a 5' portion or a 3' portion, where such complementary sequence is not present in endogenous mRNA that codes for the same protein as the synthetic mRNA.

In some embodiments, the oligonucleotide is between 8 and 20 nucleotides in length. In some embodiments, the oligonucleotide is between 15 and 18 nucleotides in length. In some embodiments, the oligonucleotide is a single-stranded oligonucleotide. In some embodiments, the oligonucleotide comprises at least one modified internucleoside linkage. In some embodiments, the oligonucleotide comprises at least one modified nucleotide. In some embodiments, at least one nucleotide comprises a 2' O-methyl. In some embodiments, the oligonucleotide comprises at least one ribonucleotide, at least one deoxyribonucleotide, at least one 2'-fluoro-deoxyribonucleotides or at least one bridged nucleotide. In some embodiments, the bridged nucleotide is a LNA nucleotide, a cEt nucleotide or a ENA modified nucleotide. In some embodiments, each nucleotide of the oligonucleotide is a LNA nucleotide. In some embodiments, the nucleotides of the oligonucleotide comprise alternating deoxyribonucleotides and 2'-fluoro-deoxyribonucleotides, 2'-O-methyl nucleotides, or bridged nucleotides. In some embodiments, the oligonucleotide is mixmer.

In some embodiments, the targeting moiety comprises one or more ligands selected from a sugar moiety, a folate moiety, and a cell-penetrating peptide. In some embodiments, the targeting moiety comprises one or more sugars. In some embodiments, the targeting moiety comprises one or more mannose moieties. In some embodiments, the targeting moiety comprises three mannose moieties. In some embodiments, the targeting moiety comprises one or more N-acetylgalactosamine ligands. In some embodiments, the targeting moiety comprises three N-acetylgalactosamine ligands.

In some embodiments, the targeting moiety is of one of the following formulae:

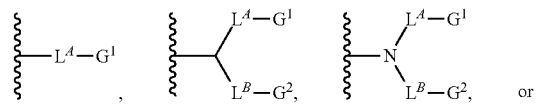

-continued

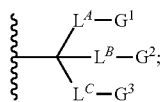

wherein:
each instance of $L^A$, $L^B$, and $L^C$ is independently either absent or is a linker selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted acylene, optionally substituted carbocyclylene, optionally substituted heterocyclylene, optionally substituted arylene, optionally substituted heteroarylene, and combinations thereof; and
each instance of $G^1$, $G^2$, and $G^3$ is independently a ligand.

In some embodiments, the targeting moiety is of the formula:

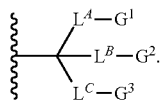

In some embodiments, each instance of $L^A$, $L^B$, and $L^C$ is independently an optionally substituted heteroalkylene linker. In some embodiments, each instance of each instance of $L^A$, $L^B$, and $L^C$ is independently of the following formula:

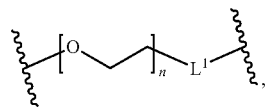

wherein:
$L^1$ is independently a bond, optionally substituted alkylene, or optionally substituted heteroalkylene; and
n is an integer from 1 to 10, inclusive. In some embodiments, each instance of $L^A$, $L^B$, and $L^C$ is independently of the following formula:

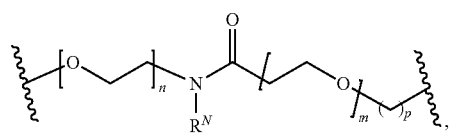

wherein:
each instance of $R^N$ is independently hydrogen, optionally substituted alkyl; optionally substituted acyl; or a nitrogen protecting group;
m is an integer from 0 to 10, inclusive; and
p is an integer from 0 to 10, inclusive. In some embodiments, each instance of $L^A$, $L^B$, and $L^C$ is independently of the following formula:

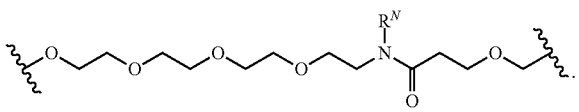

In some embodiments, each instance of $L^A$, $L^B$, and $L^C$ is independently of the following formula:

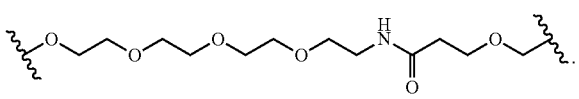 [SMILES: *COCCC(=O)NCCOCCOCCOCCO*]

In some embodiments, each instance of $L^A$, $L^B$, and $L^C$ independently comprises a triazole diradical.

In some embodiments, each triazole diradical independently has a structure selected from:

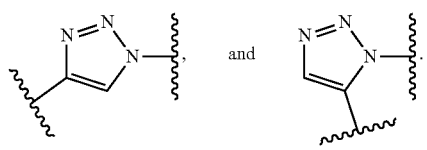 [SMILES: *c1cn(*)nn1 ; *c1cnnn1*]

In some embodiments, each instance of LA, LB, and LC is independently of the formula:

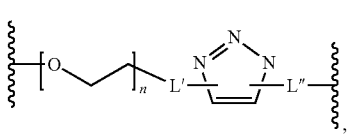

wherein:
each of L' and L" is independently a bond, optionally substituted alkylene, or optionally substituted heteroalkylene; and
n is an integer from 1 to 10, inclusive.

In some embodiments, each instance of $L^A$, $L^B$, and $L^C$ is independently of the formula:

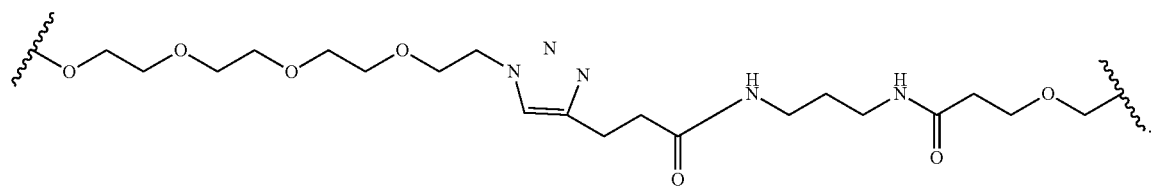

In some embodiments, each instance of $G^1$, $G^2$, and $G^3$ is independently a ligand selected from a sugar moiety, a folate moiety, or a cell-penetrating peptide. In some embodiments, each instance of $G^1$, $G^2$, and $G^3$ is independently a sugar moiety. In some embodiments, each instance of $G^1$, $G^2$, and $G^3$ is independently an N-acetylgalactosamine moiety. In some embodiments, each instance of $G^1$, $G^2$, and $G^3$ is independently of the following formula:

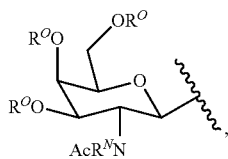

wherein:
$R^N$ is independently hydrogen, optionally substituted alkyl; optionally substituted acyl; or a nitrogen protecting group; and
each instance of $R^O$ is independently hydrogen, optionally substituted alkyl, optionally substituted acyl; or an oxygen protecting group. In some embodiments, each instance of $G^1$, $G^2$, and $G^3$ is independently of the following formula:

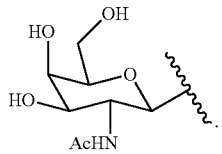

In some embodiments, each instance of $G^1$, $G^2$, and $G^3$ is independently of the formula:

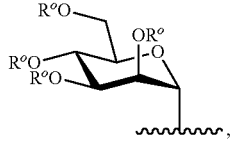

wherein each instance of $R^O$ is independently hydrogen, optionally substituted alkyl, optionally substituted acyl; or an oxygen protecting group.

In some embodiments, $G^1$, $G^2$, and $G^3$ are independently selected from the following formulae:

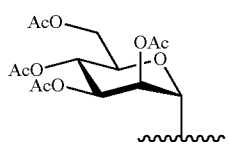 , and 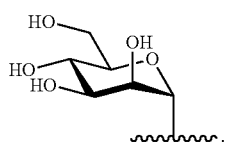 .

In some embodiments, the targeting moiety comprises a group of the formula:

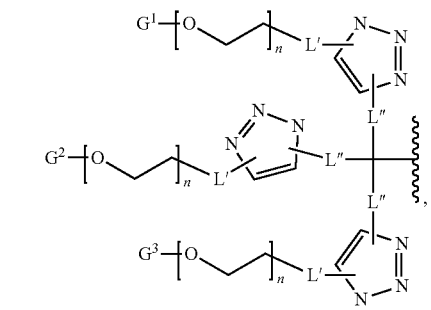

wherein:
each instance of L' and L" is independently a bond, optionally substituted alkylene, or optionally substituted heteroalkylene;
each instance of $G^1$, $G^2$, and $G^3$ is independently a sugar moiety, a folate moiety, or a cell-penetrating peptide; and
n is an integer from 1 to 10, inclusive.

In some embodiments, the targeting moiety comprises a group of the formula:

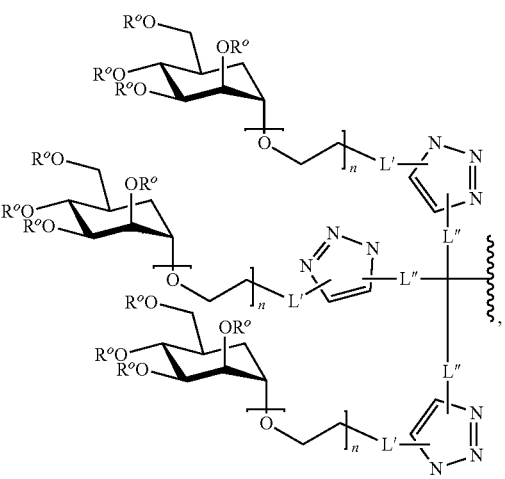

wherein:
each instance of $R^O$ is independently hydrogen, optionally substituted alkyl, optionally substituted acyl; or an oxygen protecting group.

In some embodiments, the targeting moiety comprises a group of the formula:

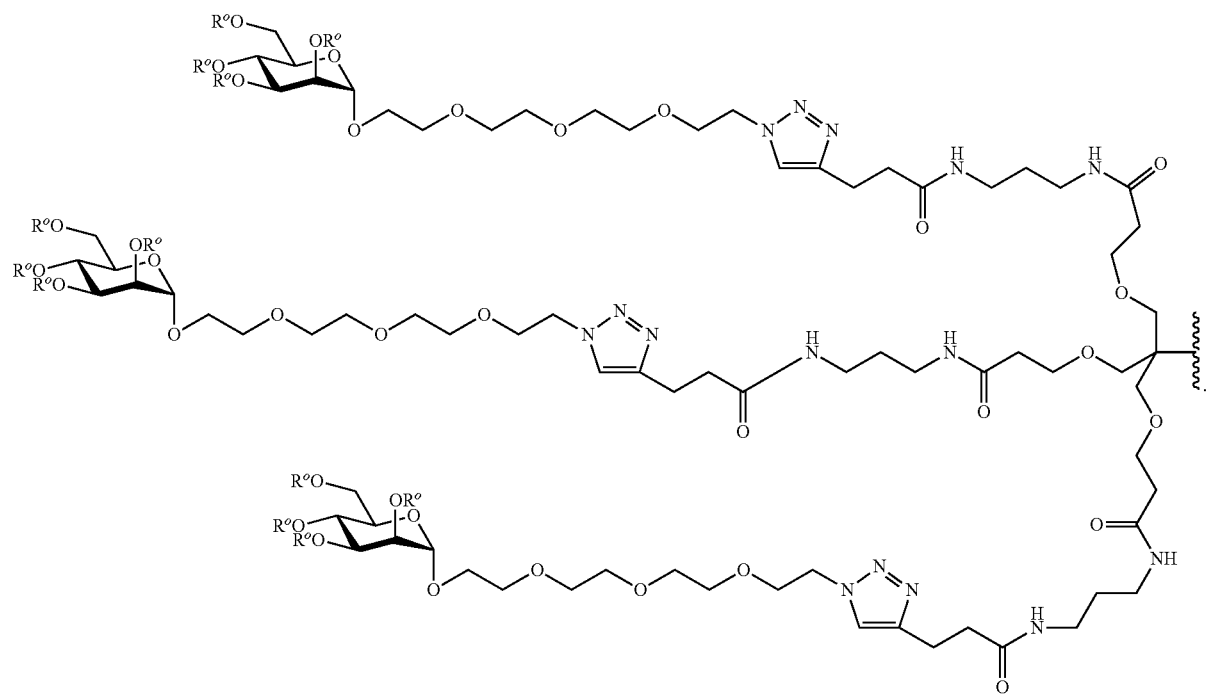
In some embodiments, the targeting moiety comprises a group of the formula:
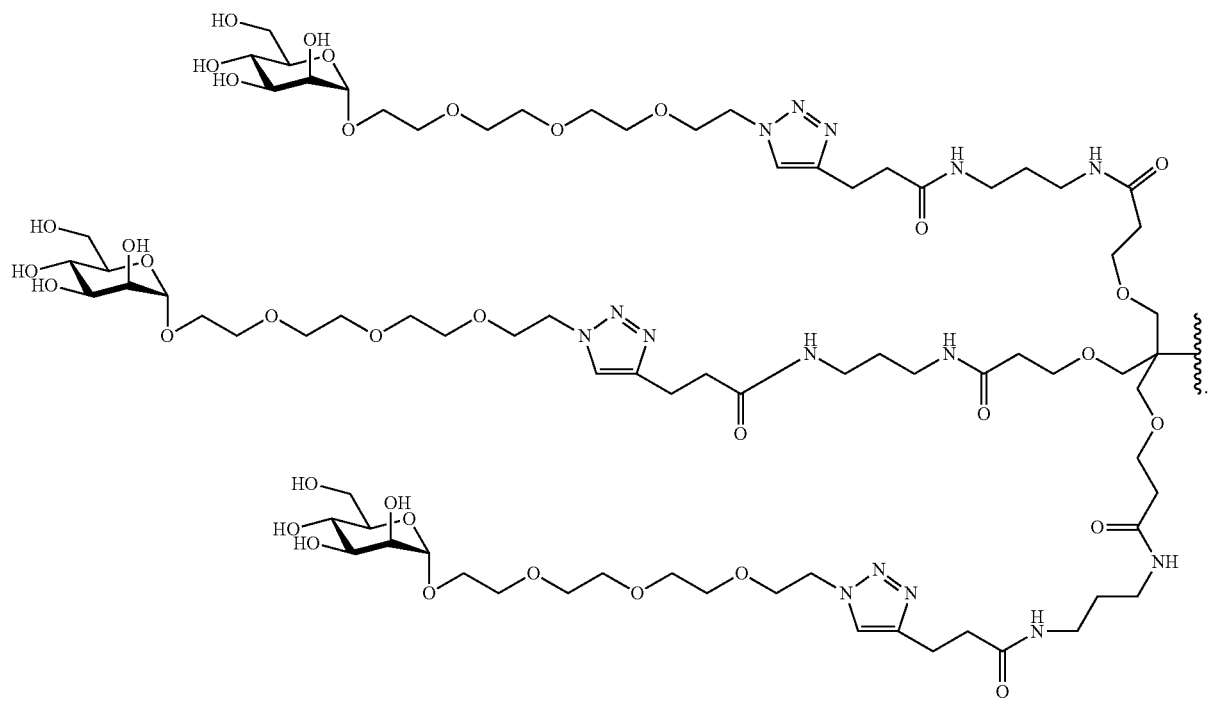
In some embodiments, the targeting moiety comprises a group of the following formula:

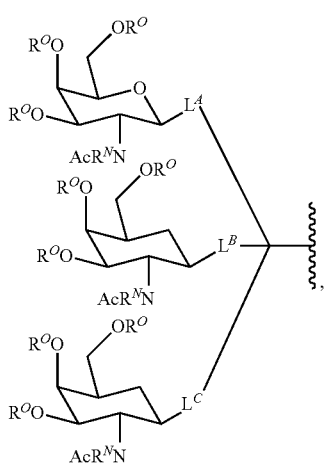

wherein:
 each instance of $R^N$ is independently hydrogen, optionally substituted alkyl, optionally substituted acyl, or a nitrogen protecting group; and
 each instance of $R^O$ is independently hydrogen, optionally substituted alkyl, optionally substituted acyl, or an oxygen protecting group.

In some embodiments, the targeting moiety comprises a group of the following formula:

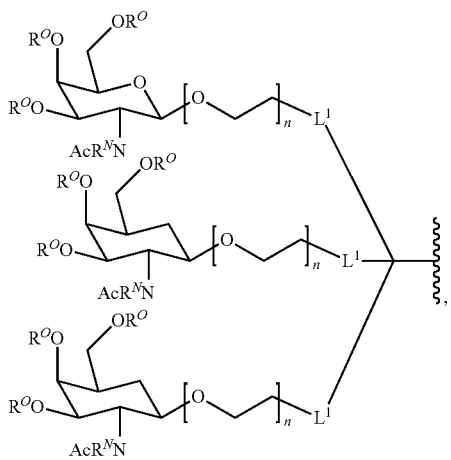

wherein:
 each instance of $L^1$ is independently a bond, optionally substituted alkylene, or optionally substituted heteroalkylene; and
 n is an integer from 1 to 10, inclusive.

In some embodiments, the targeting moiety comprises a group of the following formula:

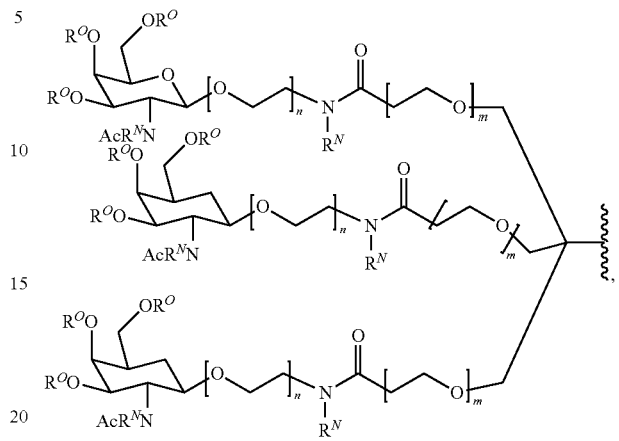

wherein:
 m is an integer from 0 to 10, inclusive; and
 p is an integer from 0 to 10, inclusive.

In some embodiments, the targeting moiety comprises a group of the following formula:

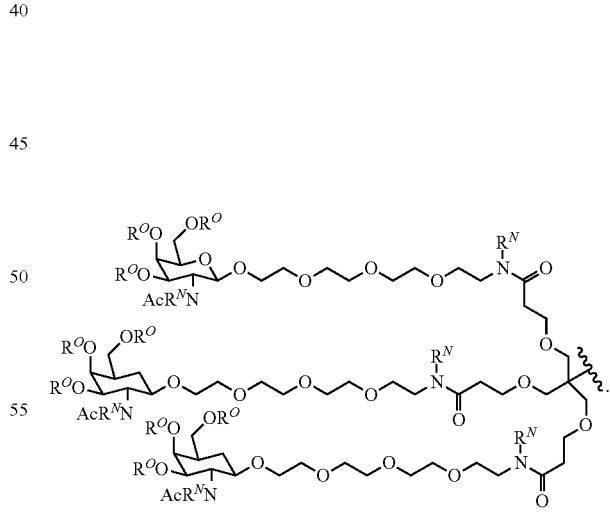

In some embodiments, the targeting moiety comprises a group of the following formula:

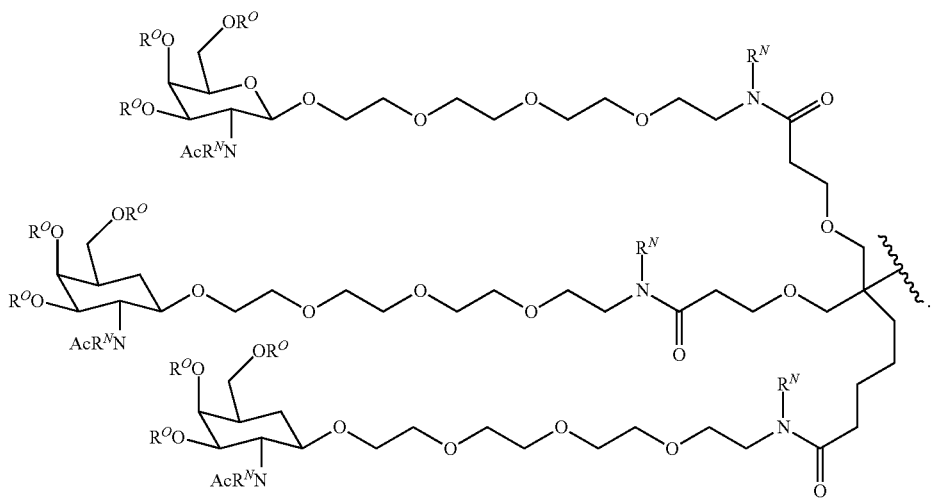

In some embodiments, the targeting moiety comprises a group of the following formula:

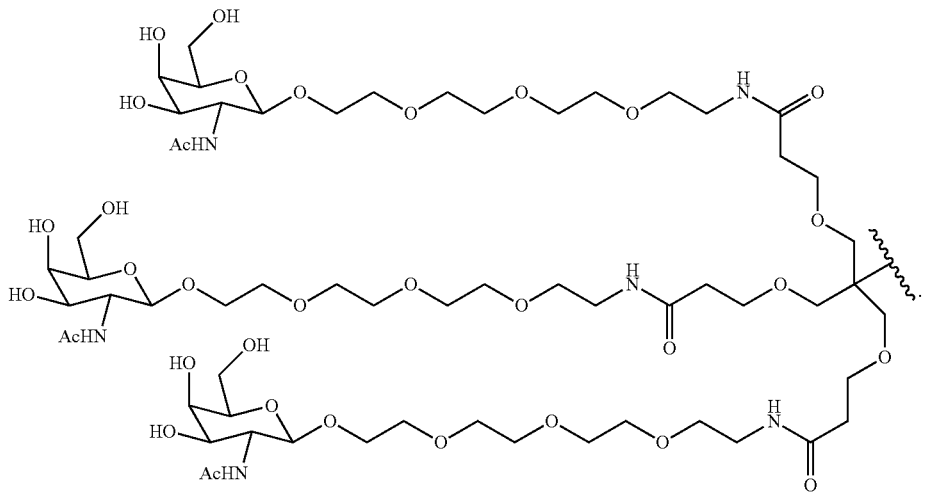 [SMILES: *C(COCCC(=O)NCCOCCOCCOCCOC1OC(CO)C(O)C(O)C1NC(C)=O)(COCCC(=O)NCCOCCOCCOCCOC1OC(CO)C(O)C(O)C1NC(C)=O)COCCC(=O)NCCOCCOCCOCCOC1OC(CO)C(O)C(O)C1NC(C)=O]

In some embodiments, the synthetic RNA comprises at least one modified nucleotide and/or modified internucleotide linkage. In some embodiments, the at least one modified nucleotide is selected from the group consisting of: 2'-amino-2'-deoxynucleotide, 2'-azido-2'-deoxynucleotide, 2'-fluoro-2'-deoxynucleotide, 2'-O-methyl-nucleotide, 2' sugar super modifier, 2'-modified thermostability enhancer, 2'-fluoro-2'-deoxyadenosine-5'-triphosphate, 2'-fluoro-2'-deoxycytidine-5'-triphosphate, 2'-fluoro-2'-deoxyguanosine-5'-triphosphate, 2'-fluoro-2'-deoxyuridine-5'-triphosphate, 2'-O-methyladenosine-5'-triphosphate, 2'-O-methylcytidine-5'-triphosphate, 2'-O-methylguanosine-5'-triphosphate, 2'-O-methyluridine-5'-triphosphate, 2'-O-methylpseudouridine-5'-triphosphate, 2'-O-methylinosine-5'-triphosphate, 2'-amino-2'-deoxycytidine-5'-triphosphate, 2'-amino-2'-deoxyuridine-5'-triphosphate, 2'-azido-2'-deoxycytidine-5'-triphosphate, 2'-azido-2'-deoxyuridine-5'-triphosphate, 2'-O-methylpseudouridine-5'-triphosphate, 2'-O-methyl-5-methyluridine-5'-triphosphate, 2'-azido-2'-deoxyadenosine-5'-triphosphate, 2'-amino-2'-deoxyadenosine-5'-triphosphate, 2'-fluoro-thymidine-5'-triphosphate, 2'-azido-2'-deoxyguanosine-5'-triphosphate, 2'-amino-2'-deoxyguanosine-5'-triphosphate, and N4-methylcytidine-5'-triphosphate. In some embodiments, the synthetic RNA encodes Ornithine transcarbamylase (OTC).

In other aspects, the disclosure provides a method of delivering a synthetic RNA to a cell, the method comprising delivering to the cell the composition of any one of the above-mentioned embodiments or any other embodiments described herein. In some embodiments, the cell is in vitro. In some embodiments, the cell is in vivo. In some embodiments, the cell is ex vivo.

In other aspects, the disclosure provides a method of treating ornithine transcarbamylase deficiency in a subject, the method comprising administering an therapeutically effective amount of a composition to a subject having ornithine transcarbamylase deficiency, wherein the composition is of any one of the above-mentioned embodiments or any other embodiments described herein and wherein the synthetic RNA encodes Ornithine transcarbamylase (OTC). In certain aspects, the disclosure provides a method of treating ornithine transcarbamylase deficiency in a subject, the method comprising administering an therapeutically effective amount of a composition to a subject having ornithine transcarbamylase deficiency, wherein the composition is synthetic mRNA that encodes Ornithine transcarbamylase (OTC) and where one or more of the 5' portion, the 3' portion and a portion of the poly A portion of the synthetic mRNA, includes a sequence that is complementary to the oligonucleotide covalently linked to the targeting moiety.

In other aspects, the disclosure provides a kit comprising: an oligonucleotide of any one of the above-mentioned embodiments or any other embodiments described herein; and a synthetic RNA of any one of the above-mentioned embodiments or any other embodiments described herein.

In other aspects, the disclosure provides a synthetic RNA of any one of the above-mentioned embodiments or any other embodiments described herein.

In yet other aspects, the disclosure provides a pharmaceutical preparation comprising a complex, wherein the complex comprises:
- a single-stranded nucleic acid non-covalently associated with an oligonucleotide;
- wherein the single-stranded nucleic acid is substantially longer than the oligonucleotide; and
- wherein the oligonucleotide is covalently linked to one or more targeting moieties.

In some embodiments, the complex is of the following formula:

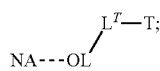

wherein:
NA is a single-stranded nucleic acid;
OL is an oligonucleotide;
----- represents one or more non-covalent bonds;
$L^T$ is a covalent bond or a linker moiety; and
T is a targeting moiety;
wherein the single-stranded nucleic acid is substantially longer than the oligonucleotide.

In some embodiments, the single-stranded nucleic acid is hybridized to the oligonucleotide. In some embodiments, the single-stranded nucleic acid is non-covalently associated with the oligonucleotide via one or more Watson-Crick base pairing interactions. In some embodiments, the oligonucleotide is associated with an end of the single-stranded nucleic acid. In some embodiments, the oligonucleotide stabilizes the single-stranded nucleic acid. In some embodiments, the complex is outside of a cell.

In some embodiments, the targeting moiety comprises one or more ligands selected from a sugar moiety, a folate moiety, and a cell-penetrating peptide. In some embodiments, the targeting moiety comprises one or more sugar ligands. In some embodiments, the targeting moiety comprises one or more mannose ligands. In some embodiments, the targeting moiety comprises three mannose ligands. In some embodiments, the targeting moiety comprises one or more N-acetylgalactosamine ligands. In some embodiments, the targeting moiety comprises three N-acetylgalactosamine ligands.

In some embodiments, the targeting moiety is of one of the following formulae:

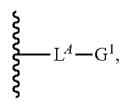 , 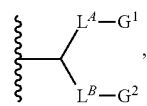 ,

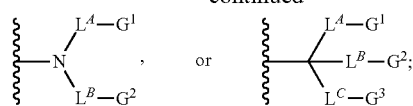

wherein:
each instance of $L^A$, $L^B$, and $L^C$ is independently either absent or is a linker selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted acylene, optionally substituted carbocyclylene, optionally substituted heterocyclylene, optionally substituted arylene, optionally substituted heteroarylene, and combinations thereof; and
each instance of $G^1$, $G^2$, and $G^3$ is independently a ligand.

In some embodiments, the targeting moiety comprises a group of the following formula:

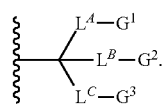

In some embodiments, each instance of $L^A$, $L^B$, and $L^C$ is independently an optionally substituted heteroalkylene linker. In some embodiments, each instance of each instance of $L^A$, $L^B$, and $L^C$ is independently of the following formula:

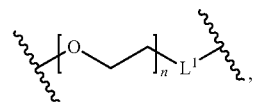

wherein:
$L^1$ is independently a bond, optionally substituted alkylene, or optionally substituted heteroalkylene; and
n is an integer from 1 to 10, inclusive. In some embodiments, each instance of $L^A$, $L^B$, and $L^C$ is independently of the following formula:

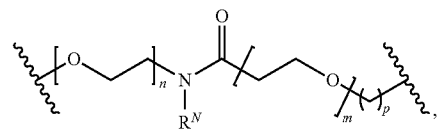

wherein:
each instance of $R^N$ is independently hydrogen, optionally substituted alkyl; optionally substituted acyl; or a nitrogen protecting group;
m is an integer from 0 to 10, inclusive; and
p is an integer from 0 to 10, inclusive. In some embodiments, each instance of $L^A$, $L^B$, and $L^C$ is independently of the following formula:

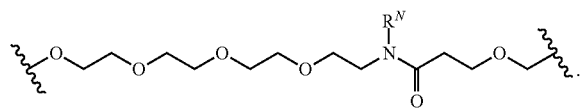

In some embodiments, each instance of $L^A$, $L^B$, and $L^C$ is independently of the following formula:

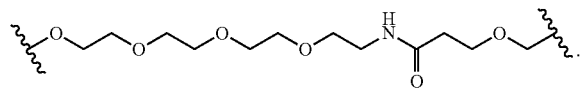 [SMILES: *COCCC(=O)NCCOCCOCCOCCO*]

In some embodiments, each instance of $L^A$, $L^B$, and $L^C$ independently comprises a triazole diradical. In some embodiments, the triazole diradical has a structure selected from:

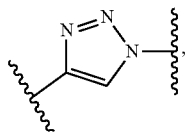 and 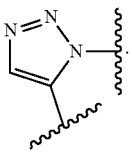

In some embodiments, each instance of $L^A$, $L^B$, and $L^C$ is independently of the formula:

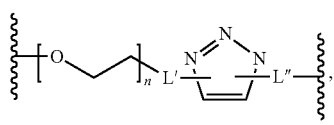

wherein:
each of L' and L" is independently a bond, optionally substituted alkylene, or optionally substituted heteroalkylene; and
n is an integer from 1 to 10, inclusive. In some embodiments, each instance of $L^A$, $L^B$, and $L^C$ is independently of the formula:

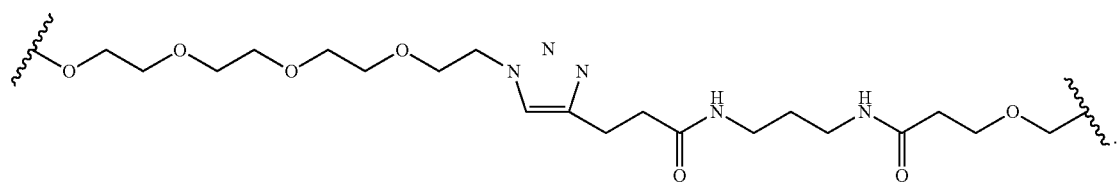

In some embodiments, each instance of $G^1$, $G^2$, and $G^3$ is independently a ligand selected from a sugar moiety, a folate moiety, or a cell-penetrating peptide. In some embodiments, each instance of $G^1$, $G^2$, and $G^3$ is independently a sugar moiety. In some embodiments, each instance of $G^1$, $G^2$, and $G^3$ is independently an N-acetylgalactosamine moiety.

In some embodiments, each instance of $G^1$, $G^2$, and $G^3$ is independently of the following formula:

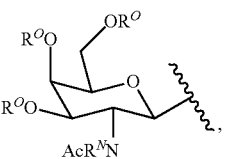

wherein:
$R^N$ is independently hydrogen, optionally substituted alkyl; optionally substituted acyl; or a nitrogen protecting group; and
each instance of $R^O$ is independently hydrogen, optionally substituted alkyl, optionally substituted acyl; or an oxygen protecting group. In some embodiments, each instance of $G^1$, $G^2$, and $G^3$ is independently of the following formula:

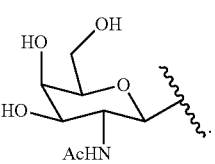 [SMILES: *C1OC(CO)C(O)C(O)C1NC(C)=O]

In some embodiments, each instance of $G^1$, $G^2$, and $G^3$ is independently mannose or a mannose derivative. In some embodiments, each instance of $G^1$, $G^2$, and $G^3$ is independently of the following formula:

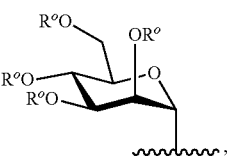

wherein each instance of $R^O$ is independently hydrogen, optionally substituted alkyl, optionally substituted acyl; or an oxygen protecting group. In some embodiments, $G^1$, $G^2$, and $G^3$ are independently selected from the following formulae:

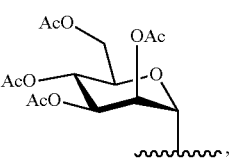, and

-continued

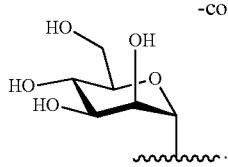

In some embodiments, the targeting moiety comprises a group of the formula:

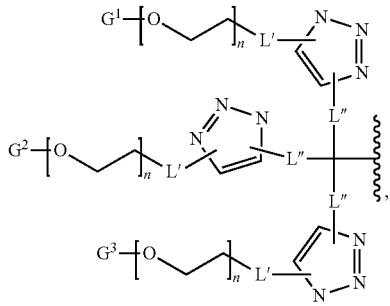

wherein:
each instance of L' and L" is independently a bond, optionally substituted alkylene, or optionally substituted heteroalkylene;
each instance of $G^1$, $G^2$, and $G^3$ is independently a sugar moiety, a folate moiety, or a cell-penetrating peptide; and
n is an integer from 1 to 10, inclusive.

In some embodiments, the targeting moiety comprises a group of the formula:

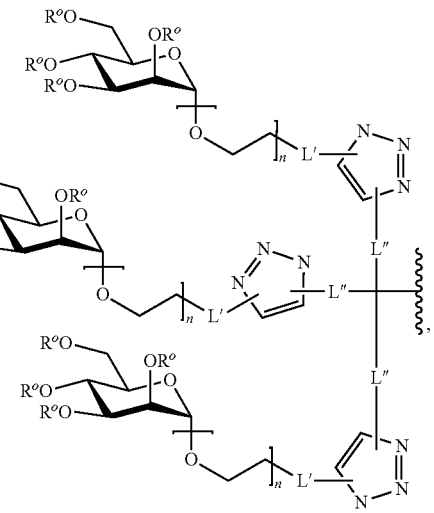

wherein:
each instance of $R^O$ is independently hydrogen, optionally substituted alkyl, optionally substituted acyl; or an oxygen protecting group.

In some embodiments, the targeting moiety comprises a group of the formula:

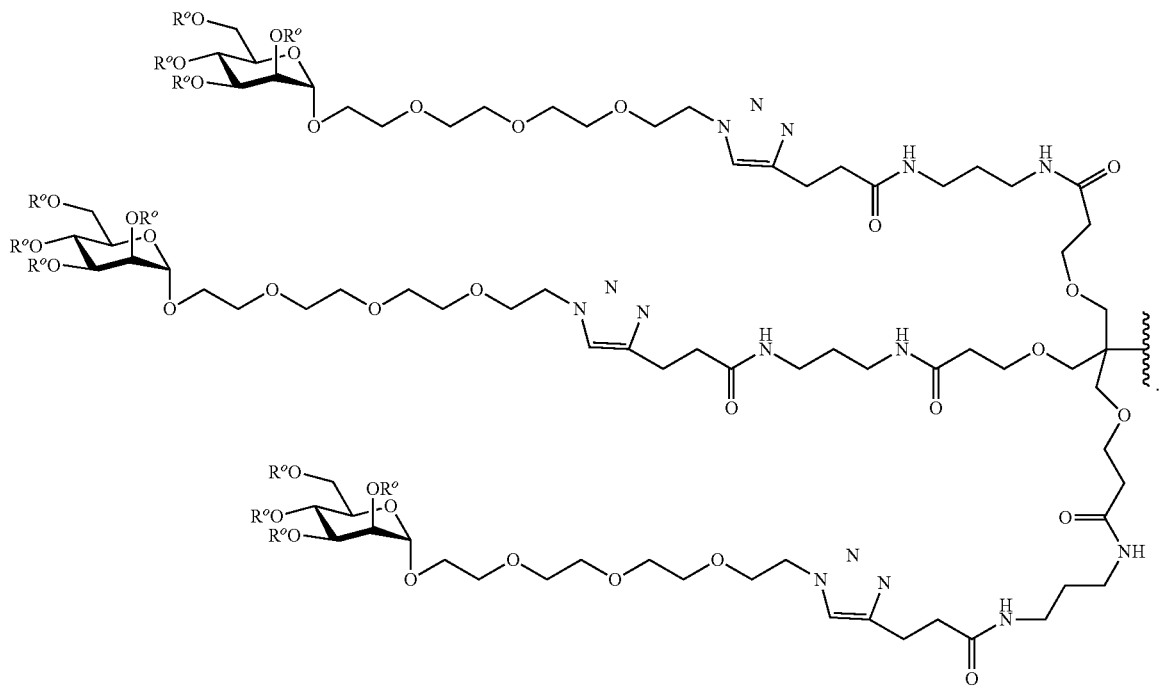

In some embodiments, the targeting moiety comprises a group of the formula:

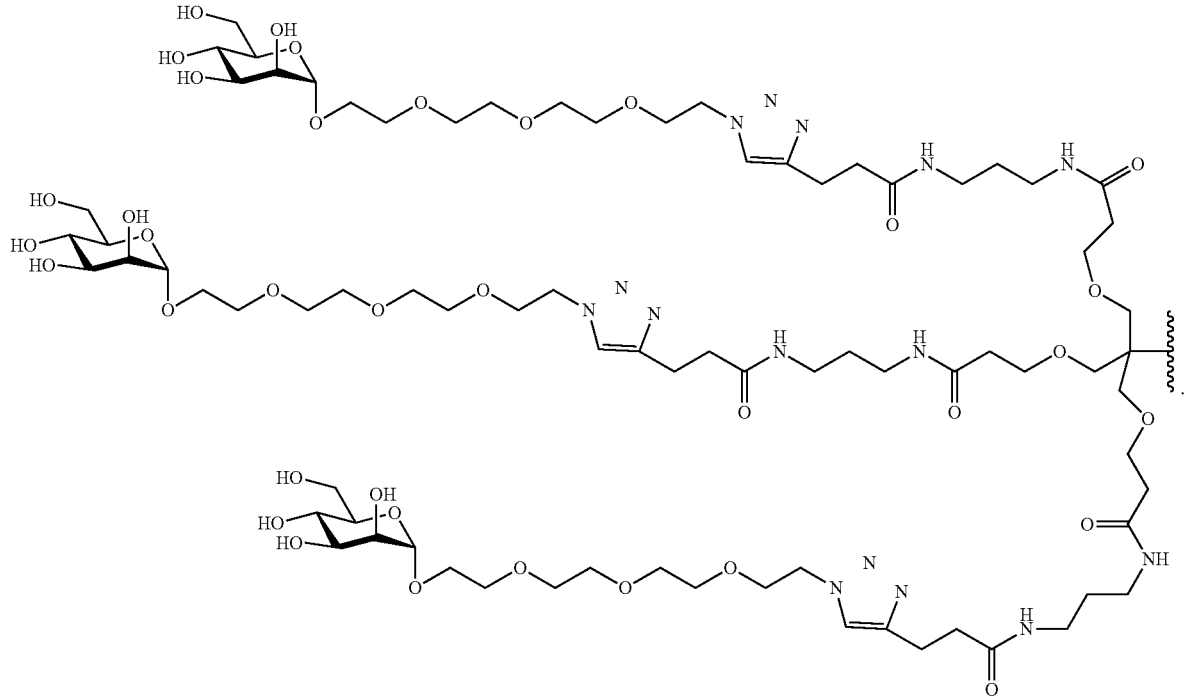

In some embodiments, the targeting moiety comprises a group of the formula:

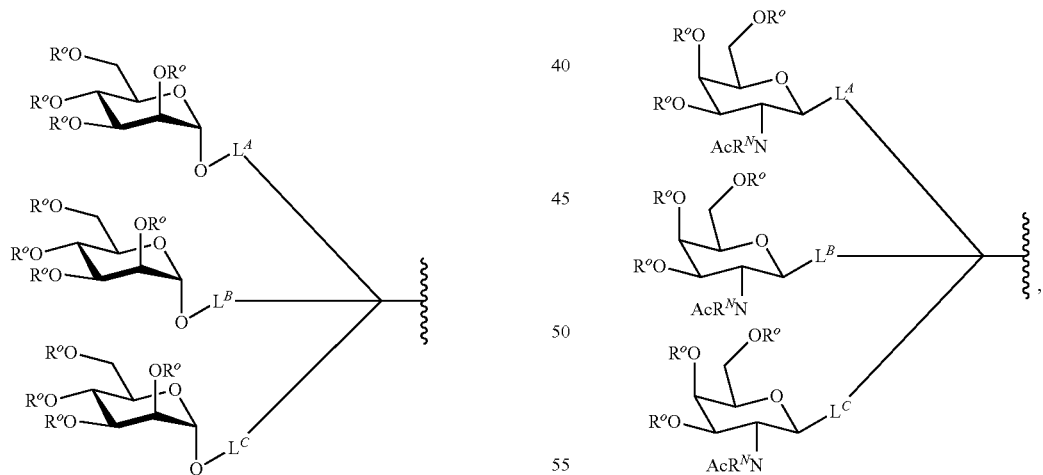

wherein each instance of $R^O$ is independently hydrogen, optionally substituted alkyl, optionally substituted acyl; or an oxygen protecting group.

In some embodiments, the targeting moiety comprises a group of the following formula:

wherein:
each instance of $R^N$ is independently hydrogen, optionally substituted alkyl, optionally substituted acyl, or a nitrogen protecting group; and
each instance of $R^O$ is independently hydrogen, optionally substituted alkyl, optionally substituted acyl, or an oxygen protecting group.

In some embodiments, the targeting moiety comprises a group of the following formula:

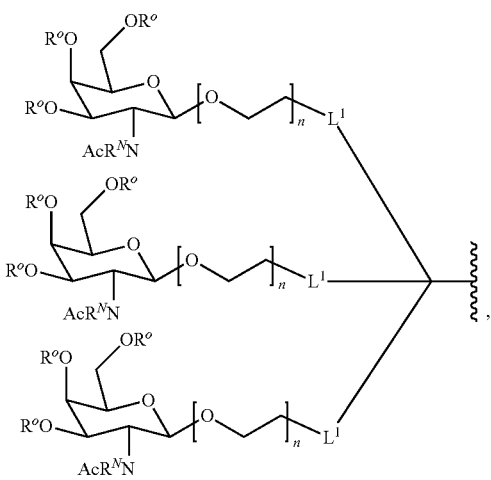

wherein:
 each instance of L¹ is independently a bond, optionally substituted alkylene, or optionally substituted heteroalkylene; and
 n is an integer from 1 to 10, inclusive.

In some embodiments, the targeting moiety comprises a group of the following formula:

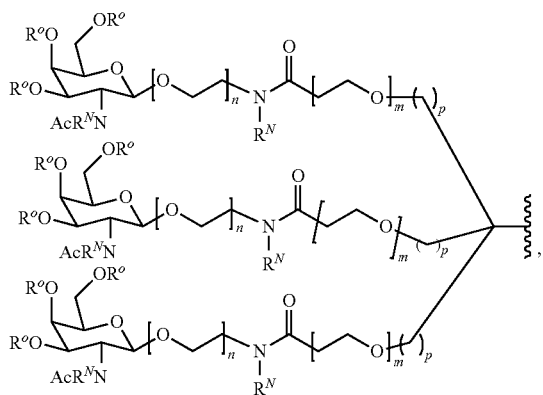

wherein:
 m is an integer from 0 to 10, inclusive; and
 p is an integer from 0 to 10, inclusive.

In some embodiments, the targeting moiety comprises a group of the following formula:

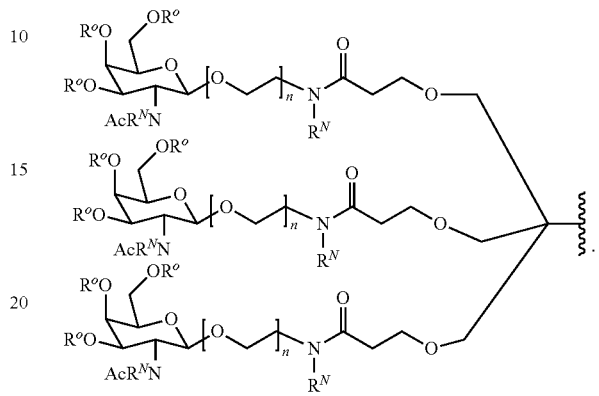

In some embodiments, the targeting moiety comprises a group of the following formula:

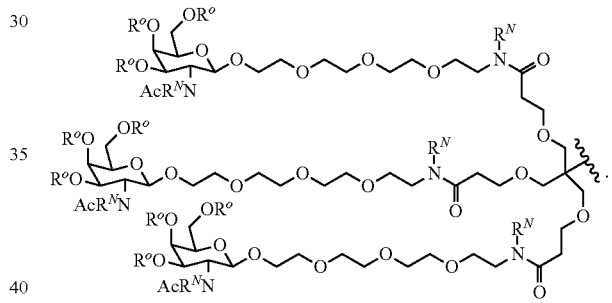

In some embodiments, the targeting moiety comprises a group of the following formula:

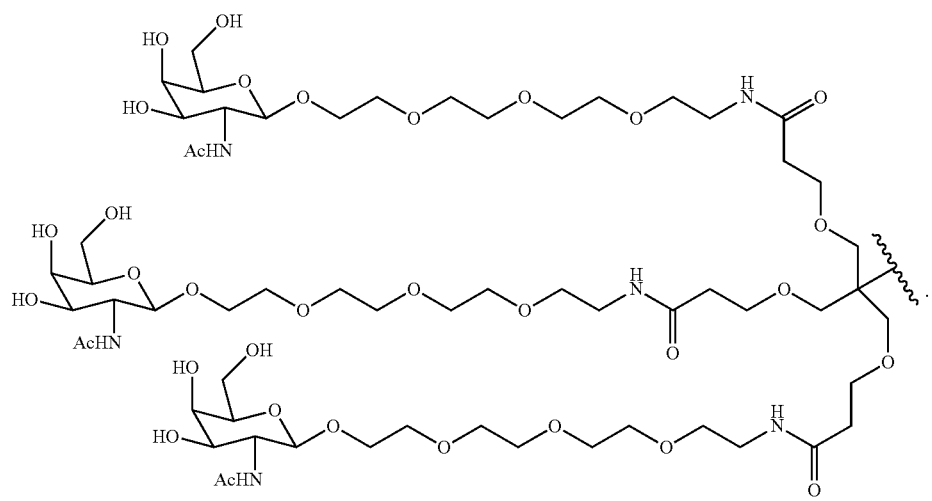 [SMILES: *C(COCCC(=O)NCCOCCOCCOCCOC1OC(CO)C(O)C(O)C1NC(C)=O)(COCCC(=O)NCCOCCOCCOCCOC1OC(CO)C(O)C(O)C1NC(C)=O)COCCC(=O)NCCOCCOCCOCCOC1OC(CO)C(O)C(O)C1NC(C)=O]

In some embodiments, $L^T$ is a linker moiety selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted acylene, optionally substituted carbocyclylene, optionally substituted heterocyclylene, optionally substituted arylene, optionally substituted heteroarylene, and combinations thereof. In some embodiments, $L^T$ is of the following formula:

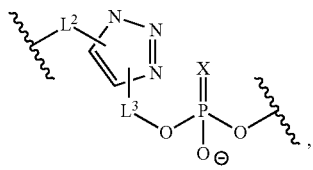

wherein:

X is O or S;

each of $L^2$, and $L^3$ is independently a bond, optionally substituted alkylene, or optionally substituted heteroalkylene. In some embodiments, $L^T$ is of the following formula:

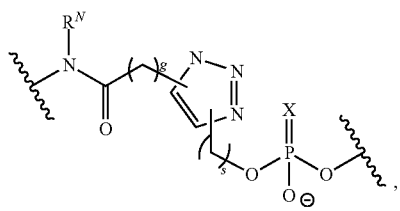

wherein:

$R^N$ is independently hydrogen, optionally substituted alkyl, optionally substituted acyl, or a nitrogen protecting group;

q is an integer from 0 to 20, inclusive; and s is an integer from 0 to 20, inclusive. In some embodiments, $L^T$ is of the following formula:

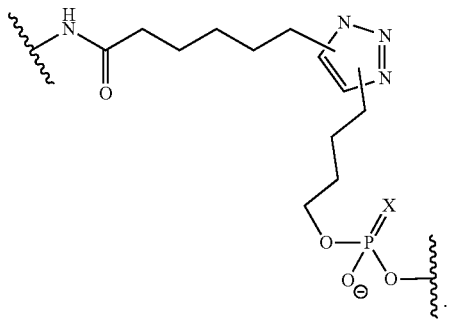

In some embodiments, $L^T$ is of the following formula:

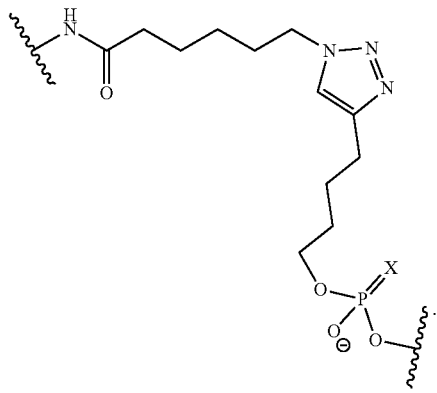

In some embodiments, the single-stranded nucleic acid is an RNA. In some embodiments, the single-stranded nucleic acid is a DNA. In some embodiments, the oligonucleotide is up to 50 nucleotides in length. In some embodiments, the oligonucleotide comprises at least one modified internucleoside linkage. In some embodiments, the oligonucleotide comprises at least one modified nucleotide.

In other aspects, the disclosure provides a method for treating a disease or condition in a subject in need thereof, the method comprising administering to the subject a pharmaceutical preparation of any one of the above-mentioned embodiments or any other embodiments described herein. In some embodiments, the disease or condition is a neurological condition, autoimmune disease, inflammatory disease, liver disease, proliferative disease, ocular condition, cardiovascular disease, metabolic condition, or hematological disease. In some embodiments, the subject is a human.

In other aspects, the disclosure provides a method of delivering a single-stranded nucleic acid to a cell, the method comprising contacting the cell with a pharmaceutical preparation of any one of the above-mentioned embodiments or any other embodiments described herein. In some embodiments, the cell is contacted in vivo. In some embodiments, the cell is contacted in vitro. In some embodiments, the cell is contacted ex vivo.

In other aspects, the disclosure provides a method of modulating gene expression in a subject, the method comprising administering to the subject a pharmaceutical preparation of any one of the above-mentioned embodiments or any other embodiments described herein. In some embodiments, the subject is a human. In some embodiments, the method is a method for increasing gene expression in a subject. In some embodiments, the method is a method for decreasing gene expression in a subject.

In other aspects, the disclosure provides a kit comprising a pharmaceutical preparation of any one of the above-mentioned embodiments or any other embodiments described herein.

The details of one or more embodiments of the invention are set forth in the description below. Other features or advantages of the present invention will be apparent from the following drawings and detailed description of several embodiments, and also from the appending claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 5A is a schematic of an exemplary synthetic mRNA containing a human OTC open reading frame (ORF) and a hemoglobin subunit alpha 1 (HBA1) 3'UTR followed by a synthetic 3'UTR region for binding anti-miR122 GalNAc-conjugated oligonucleotides and a polyA tail. The synthetic region contains an alternating pattern of a 15 nucleotide binding site that contains a partial miR122 sequence complementary to the oligonucleotide (122BindSite) and a 12 nucleotide spacer (12N Spacer).

FIG. 5B is a schematic of an exemplary synthetic mRNA containing a human OTC open reading frame (ORF) and a hemoglobin subunit alpha 1 (HBA1) 3'UTR followed by a polyA tail.

In FIG. 8B, sequences correspond from top to bottom to SEQ ID NOs: 19 and 20.

FIG. 9A and FIGS. 9B-9C are schematics of an exemplary synthetic mRNA containing either a human OTC ORF or containing an ORF with a mouse leader peptide and human OTC exons 2-10, either way followed by a synthetic 3'UTR that contains a Hba-a1 3'UTR and a synthetic UTR sequence for binding to a GalNAc-conjugated oligonucleotide with an exemplary arrangement of alternating 12 nucleotide spacers and oligonucleotide binding sites shown. In FIGS. 9B-9C, sequences correspond from top to bottom to SEQ ID NOs: 21 and 22.

DETAILED DESCRIPTION OF THE INVENTION

Figure 1A:
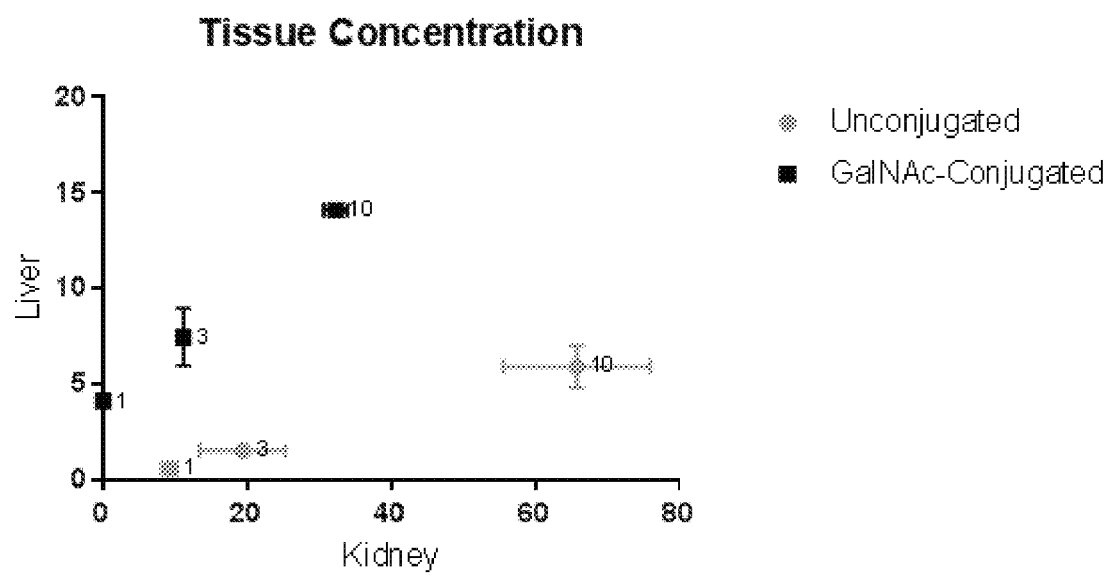
FIG. 1A is a graph showing the tissue concentration in liver versus kidney of an oligonucleotide either unconjugated or conjugated to a GalNAc moiety. The amount delivered was 1, 3, or 10 mg/kg of each oligonucleotide and the tissue concentration was measured 6 days after administration of the oligonucleotide. The number next to each data point represents the number of animals tested. Sequences correspond from top to bottom to SEQ ID NOs: 17 and 18.

The disclosure provides compositions and methods of facilitating delivery of nucleic acids to cells, such as delivery to liver cells (particularly hepatocytes). In some embodiments, oligonucleotides are provided that are associated with (e.g., covalently linked to) one or more targeting moieties that direct the oligonucleotides and complexes containing the oligonucleotides to a particular cell or tissue. In some embodiments, such oligonucleotides are associated with (e.g., covalently linked to) one or more GalNAc-moieties that direct the oligonucleotide to hepatocytes. In some embodiments, such GalNac-modified oligonucleotides facilitate or enhance delivery of other nucleic acids associated with, e.g., complexed with or based-paired with, the oligonucleotides. In some aspects, it has been found that oligonucleotides having one or more N-acetylgalactosamine (GalNAc) moieties exhibit enhanced delivery to liver tissue or hepatocytes in vivo compared with oligonucleotides that do not have such targeting moieties. In some embodiments, use of an oligonucleotide covalently linked to one or more targeting moieties, such as a GalNAc-conjugated oligonucleotide, facilitates or enhances delivery of synthetic mRNAs that contain one or more binding sites for the oligonucleotide.

Nucleic Acids

In some aspects, nucleic acids are provided in a complex or composition with an oligonucleotide as described herein covalently linked to a targeting moiety as described herein. In some embodiments, association of a nucleic acid with an oligonucleotide covalently linked to a targeting moiety facilitates or enhances delivery of the nucleic acid to a cell, e.g., compared to delivery in the absence of the oligonucleotide.

The nucleic acid may be single-stranded or double-stranded. Single stranded nucleic acids may include secondary structures, e.g., a loop or helix structure. In some embodiments, the nucleic acid is an RNA (e.g., an mRNA, a tRNA, rRNA, snoRNA, miRNA, ncRNA, long-noncoding RNA, or shRNA). In some embodiments, the nucleic acid is a DNA. In some embodiments, the nucleic acid comprises RNA and DNA nucleotides.

In some embodiments, the nucleic acid is substantially longer than an oligonucleotide as described herein. In some embodiments, the nucleic acid is at least two times, at least three times, at least four times, at least five times, at least 10 times, at least 20 times, at least 50 times, at least 100 times, at least 200 times, at least 500 times, or at least 1000 times as long as an oligonucleotide as described herein. In some embodiments, the nucleic acid is at least 50, at least 100, at least 200, at least 300, at least 400, at least 500, at least 600, at least 700, at least 800, at least 900, at least 1000, at least 2000, at least 3000, at least 4000, at least 5000, or at least 10000 nucleotides longer than an oligonucleotide as described herein.

In some embodiments, the nucleic acid is a synthetic RNA. As used herein the term, "synthetic RNA" refers to a RNA produced through an in vitro transcription reaction or through artificial (non-natural) chemical synthesis or through a combination thereof. In some embodiments, a synthetic RNA is an mRNA. In some embodiments, a synthetic RNA encodes a protein. In some embodiments, the synthetic RNA is a functional RNA (e.g., a tRNA, rRNA, snoRNA, miRNA, ncRNA, long-noncoding RNA, or shRNA). In some embodiments, a synthetic RNA comprises one or more modified nucleotides as described herein. In some embodiments, the synthetic RNA further comprises a poly A tail, a Kozak sequence, a 3' untranslated region, a 5' untranslated region, or any combination thereof. Poly A tails in particular can be added to a synthetic RNA using a variety of art-recognized techniques, e.g., using poly A polymerase (Yokoe, el al. Nature Biotechnology. 1996; 14: 1252-1256), using transcription directly from PCR products, or by ligating to the 3' end of a synthetic RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)). In one embodiment, the poly A tail, the Kozak sequence, the 3' untranslated region, the 5' untranslated region, or the any combination thereof comprises one or more modified nucleotides as described herein.

In some embodiments, a synthetic RNA (e.g., synthetic mRNA) is up to 0.5 kilobases (kb), 1 kb, 1.5 kb, 2 kb, 2.5 kb, 3 kb, 4 kb, 5 kb, 6 kb, 7 kb, 8 kb, 9 kb, 10 kb, 15 kb, 20 kb, kb, 30 kb or more in length. In some embodiments, a synthetic RNA is in a range of 0.1 kb to 1 kb, 0.5 kb to 2 kb, 0.5 kb to 10 kb, 1 kb to 5 kb, 2 kb to 5 kb, 1 kb to 10 kb, 3 kb to 10 kb, 5 kb to 15 kb, or 1 kb to 30 kb in length.

In some embodiments, the synthetic RNA (e.g., synthetic mRNA) comprises at least one, at least two, at least three, at least four, at least five, at least six, or at least seven binding regions, e.g., one, two three, four, five, sex, seven, or eight binding regions, that is/are complementary to a contiguous stretch of at least 5 nucleotides of an oligonucleotide provided herein. In some embodiments, copies of the binding region are separated from one another by a spacer region comprising at least one nucleotide. In some embodiments, each spacer region between each copy of the binding region is independently between 3 and 24 nucleotides (e.g., 3, 4, 5, 6, 7, 8, 9, 10, 11, 12, 13, 14, 15, 16, 17, 18, 19, 20, 21, 22, 23, or 24 nucleotides) in length.

In some embodiments, the synthetic RNA is a synthetic mRNA and the at least one binding region (such as at least two, at least three, at least four, at least five, at least six, or at least seven binding regions, e.g., one, two three, four, five, sex, seven, or eight binding regions) is located in an untranslated region (UTR) of the synthetic mRNA. In some embodiments, at least one binding region is included in the 5' UTR of the synthetic mRNA. In some embodiments, at least one binding region is included in the 3' UTR of the synthetic mRNA. In some embodiments, the at least one binding region includes at least a portion of the sequence from the poly A portion of the synthetic mRNA. In some embodiments, each binding region has the same sequence.

In some embodiments, the synthetic mRNA UTR that includes a binding region complementary to the oligonucleotide covalently linked to the targeting moiety is a UTR sequence as described in PCT Published Application No. WO 2017/167910, WO 2017/153936, WO 2017/059902, WO 2017/001554, WO 2016/107877, or WO 2016/091391, or in U.S. Published Patent Application No. US 2017/0009244, US 2017/0252461, US 2017/0056528, US 2017/0029847, US 2015/0184195, US 2015/0218554, US 2015/0320847 or US 2007/0068265, each of which published application is herein incorporated by reference.

In some embodiments, the synthetic mRNA 5' UTR that includes a binding region is a sequence derived from cytomegalovirus, including but not limited to each of the sequences described in U.S. Pat. No. 9,061,021, which is herein incorporated by reference.

In some embodiments, the synthetic mRNA 3' UTR that includes a binding region is a sequence derived from human growth hormone, including but not limited to each of the sequences described in U.S. Pat. No. 9,061,021, which is herein incorporated by reference.

In some embodiments, at least one binding region has a different sequence than at least one other binding region. In some embodiments, each binding region has a different sequence than every other binding region. In some embodiments, the binding region comprises or consists of a non-naturally occurring sequence, e.g., a sequence that is not present in an endogenous human mRNA. In some embodiments, the binding region comprises or consists of a naturally occurring sequence, e.g., a sequence already present in a human mRNA. In some embodiments, the binding region comprises or consists of a microRNA sequence or a portion thereof, such as a miR-122 sequence or portion thereof.

In some embodiments, the synthetic RNA is unmodified. In some embodiments, the synthetic RNA is modified to include at least one modified nucleotide or modified internucleotide linkage. In some embodiments, a synthetic mRNA provided herein contains modified nucleotides in the open reading frame. In some embodiments, the modified nucleotide is selected from the group consisting of: 2'-amino-2'-deoxynucleotide, 2'-azido-2'-deoxynucleotide, 2'-fluoro-2'-deoxynucleotide, 2'-O-methyl-nucleotide, 2' sugar super modifier, 2'-modified thermostability enhancer, 2'-fluoro-2'-deoxyadenosine-5'-triphosphate, 2'-fluoro-2'-deoxycytidine-5'-triphosphate, 2'-fluoro-2'-deoxyguanosine-5'-triphosphate, 2'-fluoro-2'-deoxyuridine-5'-triphosphate, 2'-O-methyladenosine-5'-triphosphate, 2'-O-methylcytidine-5'-triphosphate, 2'-O-methylguanosine-5'-triphosphate, 2'-O-methyluridine-5'-triphosphate, pseudouridine-5'-triphosphate, 2'-O-methylinosine-5'-triphosphate, 2'-amino-2'-deoxycytidine-5'-triphosphate, 2'-amino-2'-deoxyuridine-5'-triphosphate, 2'-azido-2'-deoxycytidine-5'-triphosphate, 2'-azido-2'-deoxyuridine-5'-triphosphate, 2'-O-methylpseudouridine-5'-triphosphate, 2'-O-methyl-5-methyluridine-5'-triphosphate, 2'-azido-2'-deoxyadenosine-5'-triphosphate, 2'-amino-2'- deoxyadenosine-5'-triphosphate, 2'-fluoro-thymidine-5'-triphosphate, 2'-azido-2'-deoxyguanosine-5'-triphosphate, 2'-amino-2'-deoxyguanosine-5'-triphosphate, and N4-methylcytidine-5'-triphosphate. See, e.g., U.S. Pat. No. 8,278,036 or WO2011/012316 for a discussion of such residues and their incorporation into a synthetic RNA. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification.

In some embodiments, the synthetic RNA comprises a 5' cap. In some embodiments, the cap is a methyl guanosine (m7G) cap. In some embodiments, the cap is a mRNA cap analogue (e.g., mCAP (m7G(5')ppp(5')G) or Anti-Reverse Cap Analog (ARCA) (3' O-Me-m7G(5')ppp(5')G)). For mRNA capping enzymes and procedures, see, e.g., Fechter, P.; Brownlee, G. G. "Recognition of mRNA cap structures by viral and cellular proteins" J. Gen. Virology 2005, 86, 1239-1249; European patent publication 2 010 659 A2; U.S. Pat. No. 6,312,926. In some embodiments, a 5' cap is added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase.

In some embodiments, the synthetic RNA comprises or consists of a sequence, or portion thereof, described in the Examples.

Targeting Moieties

Aspects of the disclosure relate to use of targeting moieties, e.g., covalently coupled to an oligonucleotide as described herein. Exemplary targeting moieties include lipids, carbohydrates (e.g., sugars, including monosaccharide, disaccharide, trisaccharide, tetrasaccharide, or oligosaccharide ligands, or sugar derivatives), cs, peptides (e.g., cell-penetrating peptides), proteins (e.g., antibodies or fragments thereof), small molecules, aptamers, particles, and combinations thereof.

In some embodiments, the targeting moiety comprises one or more sugars. The term "sugar" refers to monosaccharides, disaccharides, or polysaccharides (e.g., trisaccharide, tetrasaccharide, oligosaccharide). It also includes amino sugars.

Most monosaccharides can be represented by the general formula $C_yH_{2y}O_y$, (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose.

A sugar including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, isomaltose, trehalose, cellobiose, xylobiose, laminaribiose, gentiobiose, mannobiose, melibiose, nigerose, or rutinose. Exemplary trisaccharides include, but are not limited to, isomaltotriose, nigerotriose, maltotriose, melezitose, maltotriulose, raffinose, and kestose. The term "sugar" also includes other natural or synthetic stereoisomers of the carbohydrates described herein.

An "amino sugar" is a sugar in which a hydroxyl group has been replaced with an amine group (e.g., amino group, monosubstituted amino group, or disubstituted amino group). Amino sugars include glucosamine, galactosamine, and the like. N-acetylgalactosamine (GalNAc) is an example of an amino sugar.

In some embodiments, the targeting moiety comprises one or more sugars selected from lactose, galactose, galactosamine (e.g., N-acetylgalactosamine (GalNAc)), glucosamine (e.g., N-acetylgalactosamine (GalNAc)), mannose, fucose, and the like.

In some embodiments, the targeting moiety comprises one or more (e.g., one, two, three or more) amino sugars. In some embodiments, the targeting moiety comprises one or more (e.g., one, two, three or more) N-acetylgalactosamine (GalNAc) ligands.

As used herein, a "folate" is folic acid, or an ester or amide thereof. Based on the natural high affinity of folate for the folate receptor protein (FR), which is commonly expressed on the surface of many cells, including those of human cancers, folate conjugates also bind tightly to the FR and trigger cellular uptake via endocytosis.

As used herein, a "cell-penetrating peptide" is a peptide that facilitates cellular uptake of a conjugated "payload" molecule. Non-limiting examples of cell-penetrating peptides include KFF (KFFKFFKFFK (SEQ ID NO: 2)), ANT (RQIKIWFQNRRMKWKK (SEQ ID NO: 3)), TAT (GRKKKRRQRRRYK (SEQ ID NO: 4)), (RXR)4XB (RXRRXRRXRRXRXB (SEQ ID NO: 5)), (RFR)4XB (RFRRFRRFRRFRXB (SEQ ID NO: 6)), PKFF (KFFKFFKFFK(SEQ ID NO: 2)-O-cgatcattcaaa(SEQ ID NO: 7)-NH2), PANT (RQIKIWFQNRRMKWKK(SEQ ID NO: 3)-O-cgatcattcaaa(SEQ ID NO: 7)-NH2), PTAT (GRKKKRRQRRRYK(SEQ ID NO: 4)-O-cgatcattcaaa (SEQ ID NO: 7)-NH2), PRXR (RXRRXRRXRRXRXB (SEQ ID NO: 5)-O-cgatcattcaaa(SEQ ID NO: 7)-NH2), and PRFR (RFRRFRRFRRFRXB(SEQ ID NO: 6)-O-cgatcattcaaa(SEQ ID NO: 7)-NH2).

Other examples of "targeting moieties" contemplated include those disclosed in, e.g., U.S. Pat. Nos. 8,962,580; 8,828,956; 9,198,972; 9,181,549; International Publication No. WO 2015/006740; International Publication No. WO 2013/166121; and International Publication No. WO 2014/172698; the entire contents of each of which is incorporated herein by reference.

In some embodiments, the targeting moiety comprises a group of one of the following formulae:

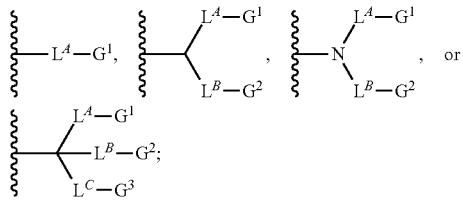

wherein:

each instance of $L^A$, $L^B$, and $L^C$ is independently either absent or is a linker selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted acylene, optionally substituted carbocyclylene, optionally substituted heterocyclylene, optionally substituted arylene, optionally substituted heteroarylene, and combinations thereof; and each instance of $G^1$, $G^2$, and $G^3$ is independently a ligand.

In some embodiments, each instance of $L^A$, $L^B$, and $L^C$ is independently either absent or is an optionally substituted heteroalkylene linker. In some embodiments, each instance of $L^A$, $L^B$, and $L^C$ is independently a $C_{1-30}$ alkylene linker. In some embodiments, each instance of $L^A$, $L^B$, and $L^C$ is independently a $C_{10-20}$ alkylene linker. In some embodiments, each instance of $L^A$, $L^B$, and $L^C$ is independently a heteroalkylene linker comprising 1-20 carbon atoms. In some embodiments, each instance of $L^A$, $L^B$, and $L^C$ is independently a heteroalkylene linker comprising 10-20 carbon atoms. In some embodiments, $L^A$, $L^B$, and $L^C$ independently comprise a polyethylene glycol (PEG) moiety. In some embodiments, each instance of each instance of $L^A$, $L^B$, and $L^C$ is independently of the following formula:

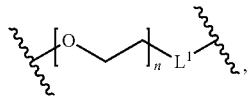

wherein:

$L^1$ is independently a bond, optionally substituted alkylene, or optionally substituted heteroalkylene; and n is an integer from 1 to 10, inclusive.

In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8. In certain embodiments, n is 9. In certain embodiments, n is 10.

In some embodiments, each instance of $L^A$, $L^B$, and $L^C$ is independently either absent or is of the following formula:

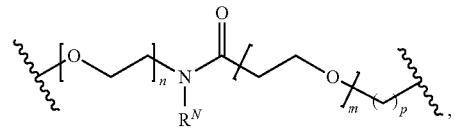

wherein:

each instance of $R^N$ is independently hydrogen, optionally substituted alkyl; optionally substituted acyl; or a nitrogen protecting group;

m is an integer from 0 to 10, inclusive; and p is an integer from 0 to 10, inclusive.

In certain embodiments, m is 0. In certain embodiments, m is 1. In certain embodiments, m is 2. In certain embodiments, m is 3. In certain embodiments, m is 4. In certain embodiments, m is 5. In certain embodiments, m is 6. In certain embodiments, m is 7. In certain embodiments, m is 8. In certain embodiments, m is 9. In certain embodiments, m is 10.

In certain embodiments, p is 0. In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7. In certain embodiments, p is 8. In certain embodiments, p is 9. In certain embodiments, p is 10.

In some embodiments, each instance of $L^A$, $L^B$, and $L^C$ is either absent or is independently of the following formula:

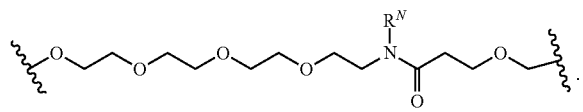

In some embodiments, each instance of $L^A$, $L^B$, and $L^C$ is independently either absent or is of the following formula:

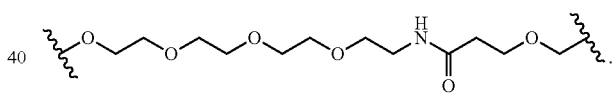

In some embodiments, each instance of $L^A$, $L^B$, and $L^C$ independently comprises a triazole diradical. In certain embodiments, each triazole diradical independently has a structure selected from:

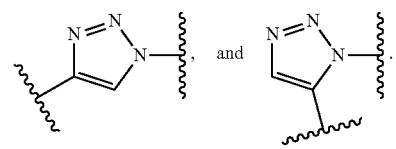 [SMILES: *c1cn(*)nn1 ; *c1cnnn1*]

In certain embodiments, each instance of $L^A$, $L^B$, and $L^C$ is independently of the formula:

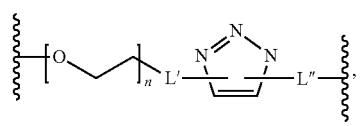

wherein each of L' and L" is independently a bond, optionally substituted alkylene, or optionally substituted heteroalkylene; and n is an integer from 1 to 10, inclusive.

In certain embodiments, each instance of $L^A$, $L^B$, and $L^C$ is independently either absent or is of the formula:

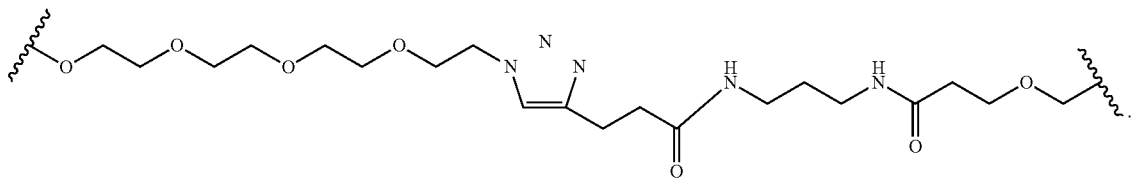

As described herein, each of $G^1$, $G^2$, and $G^3$ is independently a ligand. In some embodiments, each instance of $G^1$, $G^2$, and $G^3$ is independently a sugar ligand. Examples of sugars (e.g., sugar ligands) are provided herein. In some embodiments, each instance of $G^1$, $G^2$, and $G^3$ is independently an N-acetylgalactosamine (GalNAc) ligand. Other examples of "ligands" contemplated include those disclosed in, e.g., U.S. Pat. Nos. 8,962,580; 8,828,956; 9,198,972; 9,181,549; International Publication No. WO 2015/006740; International Publication No. WO 2013/166121; and International Publication No. WO 2014/172698; the entire contends of each of which is incorporated herein by reference.

In certain embodiments, each instance of $G^1$, $G^2$, and $G^3$ is independently of the formula:

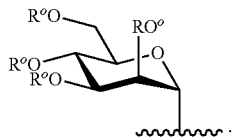

wherein each instance of $R^O$ is independently hydrogen, optionally substituted alkyl, optionally substituted acyl; or an oxygen protecting group. In certain embodiments, at least one instance of $R^O$ is hydrogen. In certain embodiments, each instance of $R^O$ is hydrogen. In certain embodiments, at least one instance of $R^O$ is optionally substituted alkyl. In certain embodiments, at least one instance of $R^O$ is optionally substituted acyl. In certain embodiments, at least one instance of $R^O$ is an oxygen protecting group.

In particular embodiments, $G^1$, $G^2$, and $G^3$ are independently selected from the formulae:

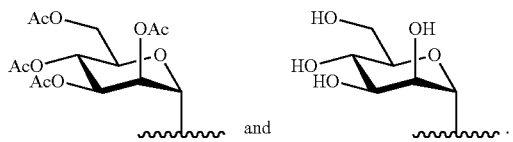

In some embodiments, each instance of $G^1$, $G^2$, and $G^3$ is independently of the following formula:

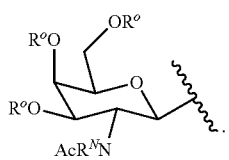

wherein:
$R^N$ is independently hydrogen, optionally substituted alkyl; optionally substituted acyl; or a nitrogen protecting group; and
each instance of $R^O$ is independently hydrogen, optionally substituted alkyl, optionally substituted acyl; or an oxygen protecting group.

As generally defined herein, Ac is —C(=O)CH$_3$.

In certain embodiments, at least one instance of $R^O$ is hydrogen. In certain embodiments, each instance of $R^O$ is hydrogen. In certain embodiments, at least one instance of $R^O$ is optionally substituted alkyl. In certain embodiments, at least one instance of $R^O$ is optionally substituted acyl. In certain embodiments, at least one instance of $R^O$ is an oxygen protecting group.

In certain embodiments, at least one instance of $R^N$ is hydrogen. In certain embodiments, at least one instance of $R^N$ is optionally substituted alkyl. In certain embodiments, at least one instance of $R^N$ is optionally substituted acyl. In certain embodiments, at least one instance of $R^N$ is a nitrogen protecting group. In certain embodiments, each instance of $R^N$ is hydrogen.

In some embodiments, each instance of $G^1$, $G^2$, and $G^3$ is independently N-acetylgalactosamine (GalNAc), of the following formula:

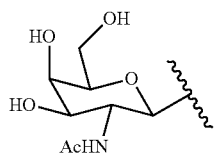

In some embodiments, the targeting moiety comprises a group of the following formula:

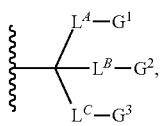

wherein:
each instance of $L^A$, $L^B$, and $L^C$ is independently either absent or is a linker selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted acylene, optionally substituted carbocyclylene, optionally substituted heterocyclylene, optionally substituted arylene, optionally substituted heteroarylene, and combinations thereof; and each instance of $G^1$, $G^2$, and $G^3$ is independently a ligand.

In some embodiments, the targeting moiety comprises a group of the following formula:

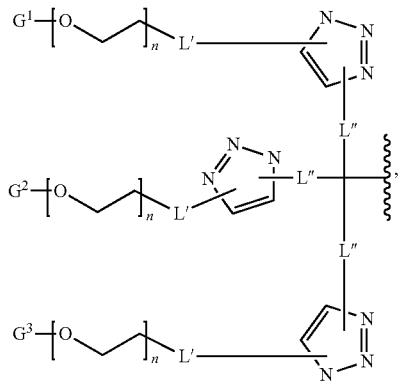

wherein each instance of L' and L" is independently a bond, optionally substituted alkylene, or optionally substituted heteroalkylene; each instance of $G^1$, $G^2$, and $G^3$ is independently a sugar moiety, a folate moiety, or a cell-penetrating peptide; and n is an integer from 1 to 10, inclusive.

In some embodiments, the targeting moiety comprises a group of the following formula:

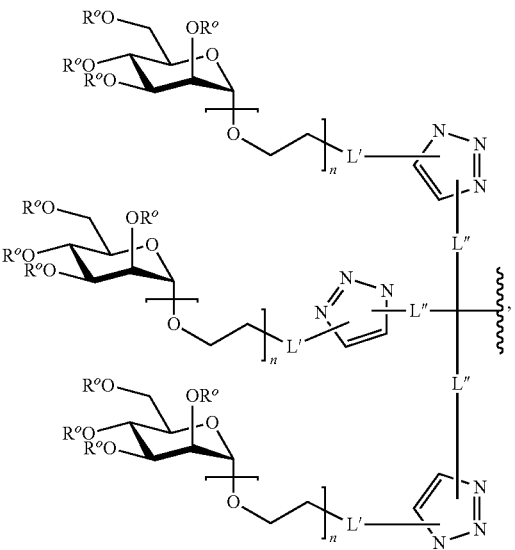

wherein each instance of $R^O$ is independently hydrogen, optionally substituted alkyl, optionally substituted acyl; or an oxygen protecting group.

In some embodiments, the targeting moiety comprises a group of the following formula:

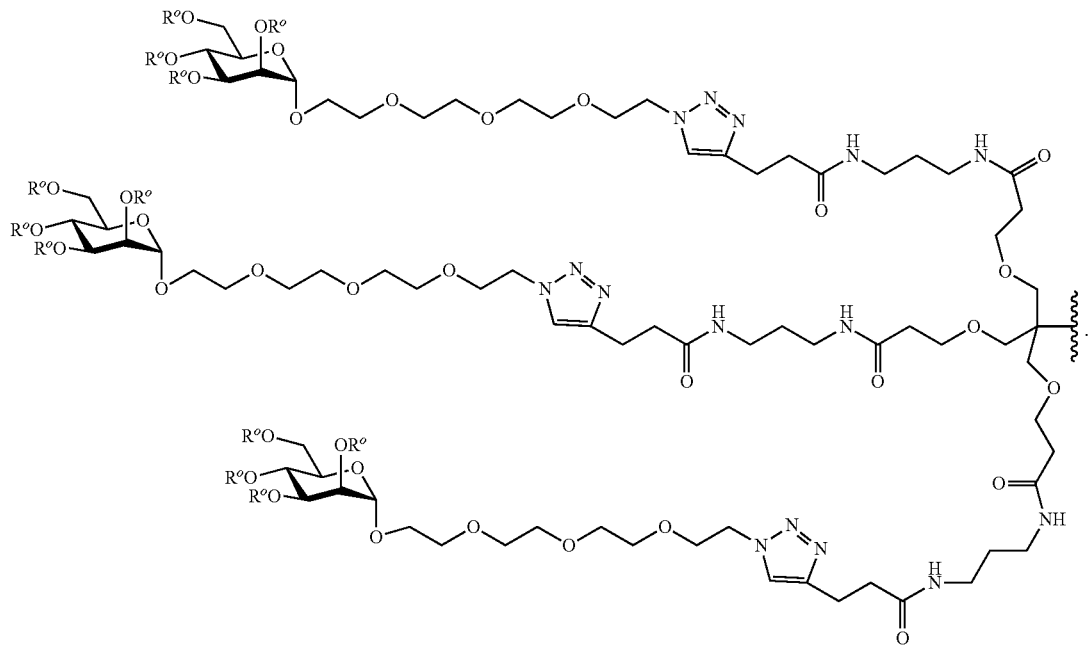

In some embodiments, the targeting moiety comprises a group of the following formula:

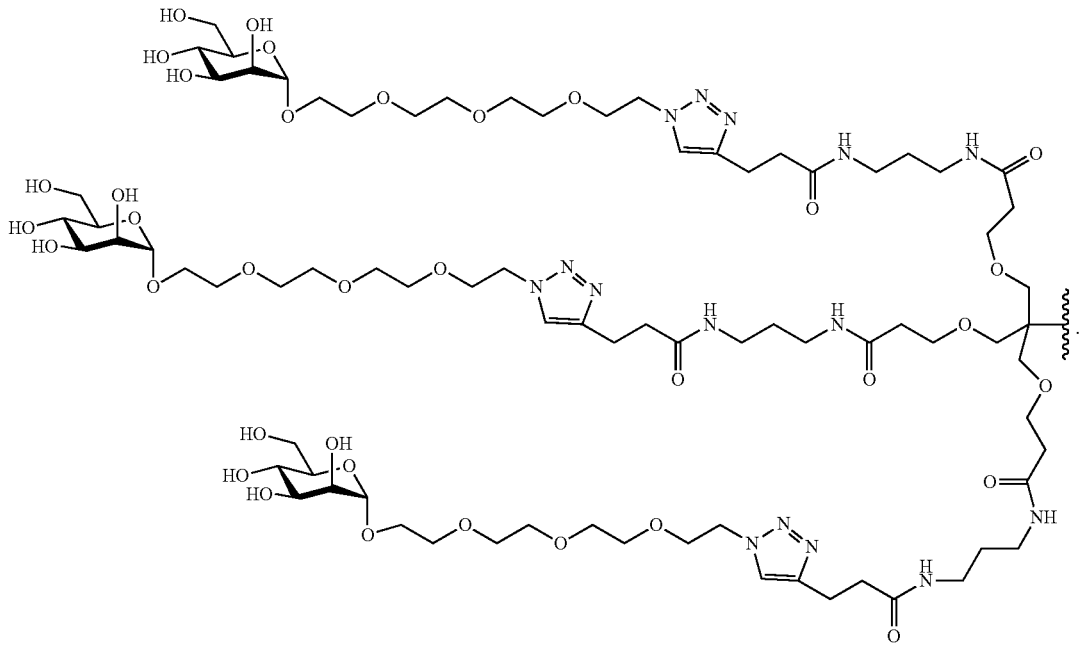

In some embodiments, the targeting moiety comprises a group of the following formula:

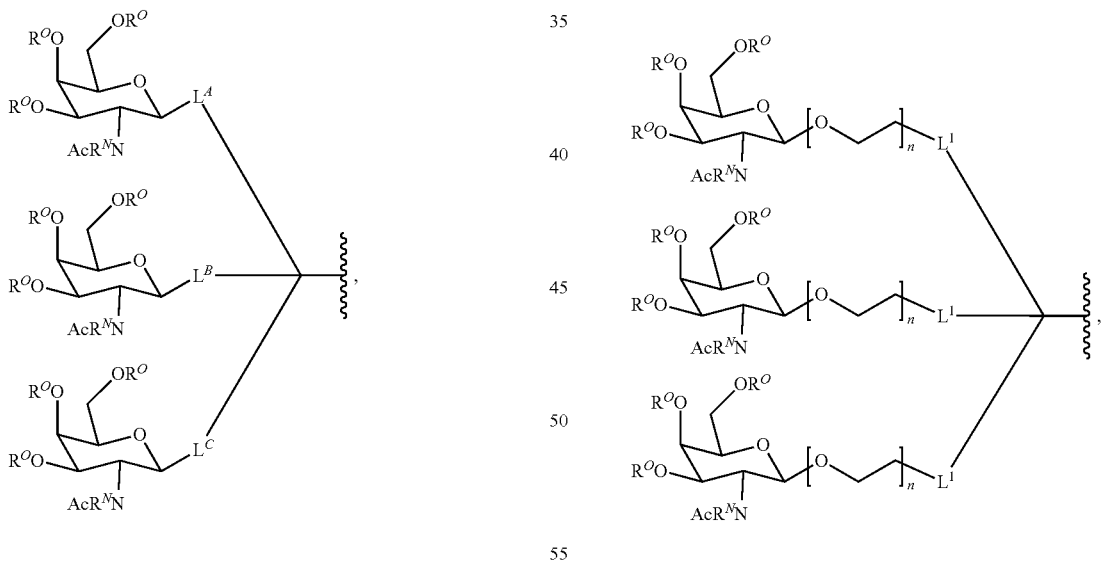

wherein:
  each instance of $R^N$ is independently hydrogen, optionally substituted alkyl, optionally substituted acyl, or a nitrogen protecting group; and
  each instance of $R^O$ is independently hydrogen, optionally substituted alkyl, optionally substituted acyl, or an oxygen protecting group.

In some embodiments, the targeting moiety comprises a group of the following formula:

wherein:
  each instance of $L^1$ is independently a bond, optionally substituted alkylene, or optionally substituted heteroalkylene; and
  n is an integer from 1 to 10, inclusive.

In some embodiments, the targeting moiety comprises a group of the following formula:

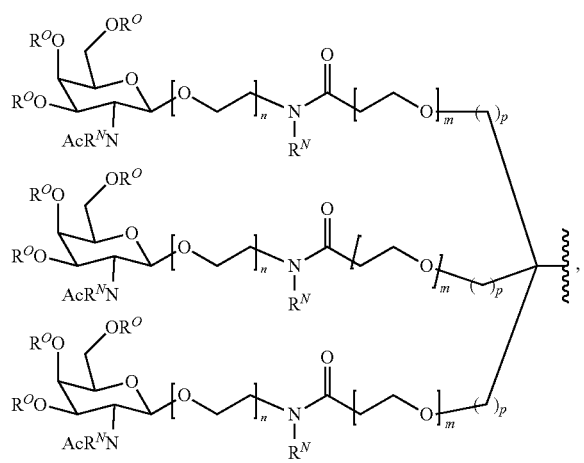
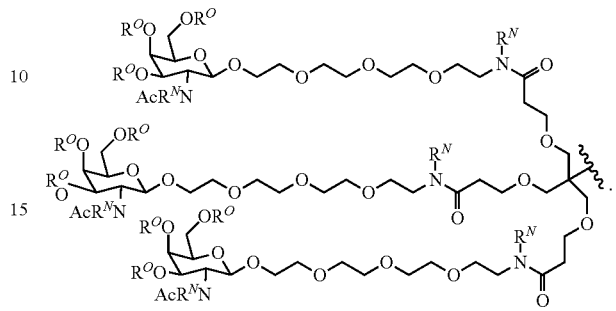
wherein:
m is an integer from 0 to 10, inclusive; and
p is an integer from 0 to 10, inclusive.
In some embodiments, the targeting moiety comprises a group of the following formula:
In some embodiments, the targeting moiety comprises a group of the following formula:
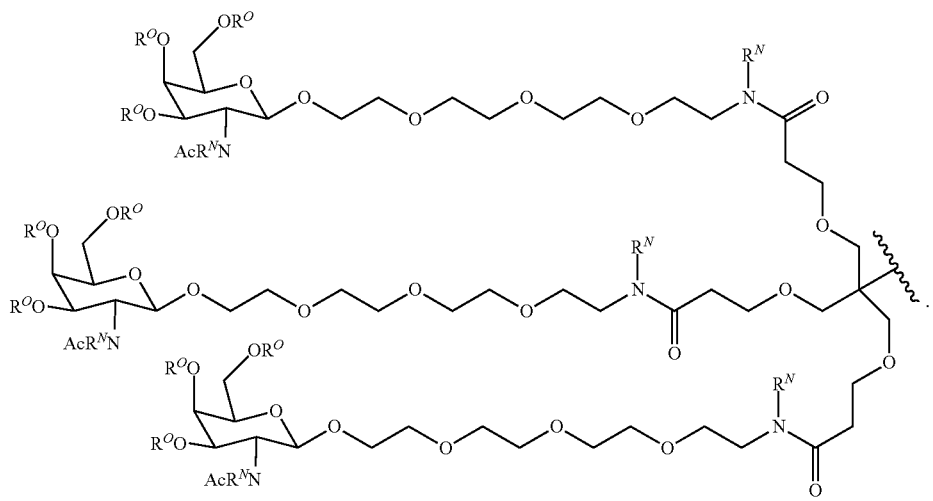
In some embodiments, the targeting moiety comprises a group of the following formula:
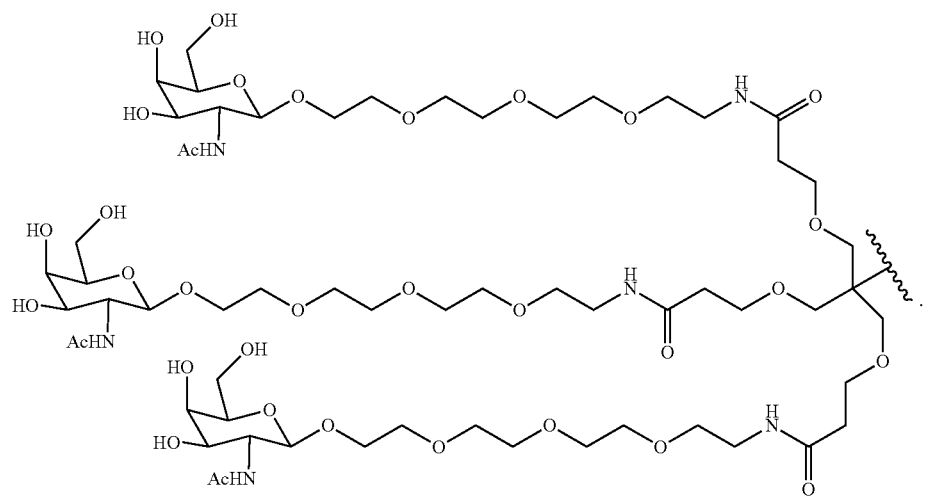 [SMILES: *C(COCCC(=O)NCCOCCOCCOCCOC1OC(CO)C(O)C(O)C1NC(C)=O)(COCCC(=O)NCCOCCOCCOCCOC1OC(CO)C(O)C(O)C1NC(C)=O)COCCC(=O)NCCOCCOCCOCCOC1OC(CO)C(O)C(O)C1NC(C)=O]

As generally defined herein, $L^1$, L', L" are each independently a bond, optionally substituted alkylene, or optionally substituted heteroalkylene.

In certain embodiments, at least one instance of $L^1$ is optionally substituted alkylene. In certain embodiments, at least one instance of $L^1$ is optionally substituted $C_{1-20}$ alkylene. In certain embodiments, at least one instance of $L^1$ is optionally substituted $C_{1-10}$ alkylene. In certain embodiments, at least one instance of $L^1$ is optionally substituted heteroalkylene. In certain embodiments, at least one instance of $L^1$ is optionally substituted $C_{1-20}$ heteroalkylene. In certain embodiments, at least one instance of $L^1$ is optionally substituted $C_{1-10}$ heteroalkylene. An optionally substituted heteroalkylene linker may contain one or more esters, amides, carbonates, carbamates, ureas, or other heteroatom-containing groups, in the linker. For example, in certain embodiments, at least one instance of $L^1$ is of the formula:

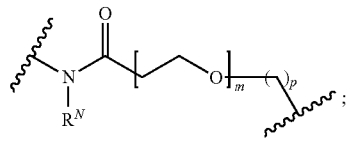

wherein $R^N$, m, and p are as defined herein. In certain embodiments, at least one instance of $L^1$ is of the formula:

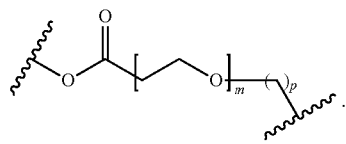

In certain embodiments, at least one instance of $L^1$ is of the formula:

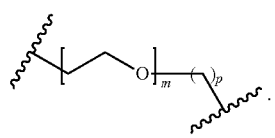

For example, in certain embodiments, each instance of $L^1$ is of the formula:

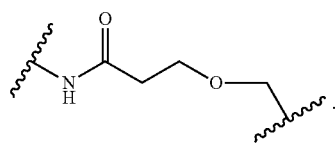 [SMILES: *COCCC(=O)N*]

In certain embodiments, L' and L" are independently a bond, optionally substituted alkylene (e.g., optionally substituted $C_{1-20}$ alkylene, optionally substituted $C_{1-10}$ alkylene, optionally substituted $C_{1-6}$ alkylene, or unsubstituted alkylene). In certain embodiments, at least one instance of L' and L" is optionally substituted heteroalkylene. In certain embodiments, at least one instance of L' and L" is optionally substituted $C_{1-20}$ heteroalkylene. In certain embodiments, at least one instance of L' and L" is optionally substituted $C_{1-10}$ heteroalkylene. In certain embodiments, at least one instance of L' and L" is optionally substituted $C_{1-6}$ heteroalkylene. An optionally substituted heteroalkylene linker may contain one or more esters, amides, carbonates, carbamates, phosphodiesters, phosphorothioates, ureas, or other heteroatom-containing groups, in the linker. In certain embodiments, at least one instance of L' and L" is substituted $C_{1-20}$ heteroalkylene. In certain embodiments, at least one instance of L' and L" is substituted $C_{1-10}$ heteroalkylene. In certain embodiments, at least one instance of L' and L" is substituted $C_{1-6}$ heteroalkylene. For example, in certain embodiments, at least one instance of L' and L" is of the formula:

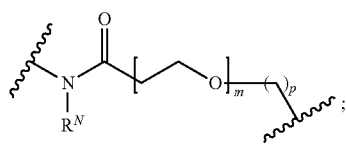

wherein $R^N$, m, and p are as defined herein. In certain embodiments, at least one instance of L' and L" is of the formula:

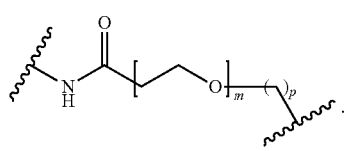

In certain embodiments, at least one instance of L' and L" is of the formula:

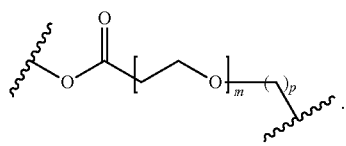

In certain embodiments, at least one instance of L' and L" is of the formula:

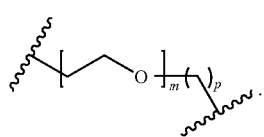

In certain embodiments, at least one instance of L' and L" is of the formula:

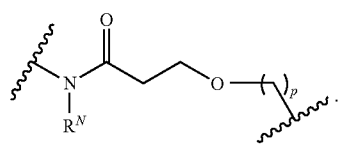

In certain embodiments, at least one instance of L' and L" is of the formula:

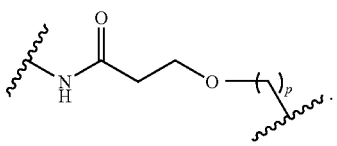

In certain embodiments, at least one instance of L' and L" is of the formula:

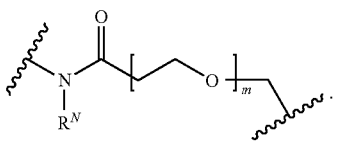

In certain embodiments, at least one instance of L' and L" is of the formula:

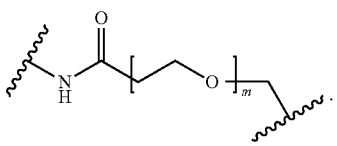

In certain embodiments, at least one instance of L' and L" is of the formula:

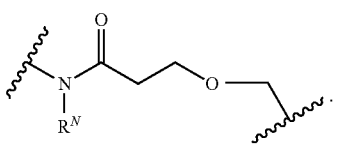

In certain embodiments, at least one instance of L' and L" is of the formula:

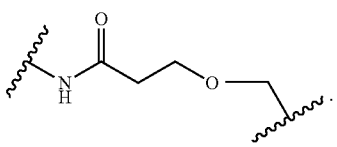

In certain embodiments, each instance of L' and L" is of the formula:

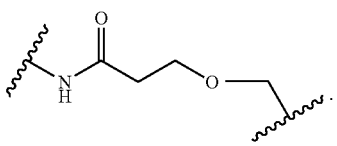

In some embodiments of the invention, the oligonucleotide (OL) is linked to the targeting moiety (T) via a linker ($L^T$). In some embodiments, $L^T$ is a bond (i.e., covalent bond). In some embodiments, $L^T$ is a linker moiety selected from the group consisting of optionally substituted alkylene, optionally substituted alkenylene, optionally substituted alkynylene, optionally substituted heteroalkylene, optionally substituted heteroalkenylene, optionally substituted heteroalkynylene, optionally substituted acylene, optionally substituted carbocyclylene, optionally substituted heterocyclylene, optionally substituted arylene, optionally substituted heteroarylene, and combinations thereof.

In some embodiments, $L^T$ comprises optionally substituted alkylene. In some embodiments, $L^T$ comprises optionally substituted $C_{1-20}$ alkylene. In some embodiments, $L^T$ comprises optionally substituted heteroalkylene. In some embodiments, $L^T$ comprises optionally substituted heteroalkylene comprising 1-20 carbon atoms. In some embodiments, $L^T$ comprises optionally substituted heterocyclylene. In some embodiments, $L^T$ Comprises optionally substituted heteroarylene. In some embodiments, $L^T$ comprises optionally substituted alkylene and optionally substituted heteroarylene. In some embodiments, $L^T$ comprises optionally substituted alkylene, optionally substituted heteroalkylene, and/or optionally substituted heteroarylene.

In some embodiments, the oligonucleotide (OL) can be linked to the targeting moiety (T) via bioconjugation. In some embodiments, the bioconjugation technique is a click chemistry technique. "Click chemistry" is a chemical approach introduced by Sharpless in 2001 and describes chemistry tailored to generate substances quickly and reliably by joining units together. See, e.g., Kolb, Finn and Sharpless *Angewandte Chemie International Edition* 2001 40, 2004-2021; Evans, *Australian Journal of Chemistry* 2007 60, 384-395). Exemplary coupling reactions (some of which may be classified as "click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgen cycloaddition; thiol-yne addition; imine formation; Michael additions (e.g., maleimide addition); and Diels-Alder reactions (e.g., tetrazine [4+2] cycloaddition). Examples of click chemistry reactions can be found in, e.g., Kolb, H. C.; Finn, M. G. and Sharpless, K. B. *Angew. Chem. Int. Ed.* 2001, 40, 2004-2021. Kolb, H. C. and Shrapless, K. B. *Drug Disc. Today*, 2003, 8, 112-1137; Rostovtsev, V. V.; Green L. G.; Fokin, V. V. and Shrapless, K. B. *Angew. Chem. Int. Ed.* 2002, 41, 2596-2599; Tomoe, C. W.; Christensen, C. and Meldal, M. *J. Org. Chem.* 2002, 67, 3057-3064. Wang, Q. et al. *J. Am. Chem. Soc.* 2003, 125, 3192-3193; Lee, L. V. et al. *J. Am. Chem. Soc.* 2003 125, 9588-9589; Lewis, W. G. et al. *Angew. Chem. Int. Ed.* 2002, 41, 1053-41057; Manetsch, R. et al., *J. Am. Chem. Soc.* 2004, 126, 12809-12818; Mocharla, V. P. et al. *Angew. Chem., Int. Ed.* 2005, 44, 116-120.

Therefore, in some embodiments, $L^T$ is a linker comprising a moiety formed by click chemistry (e.g., any moiety described above). For example, in some embodiments, $L^T$ comprises a triazole moiety.

In some embodiments, $L^T$ is of the following formula:

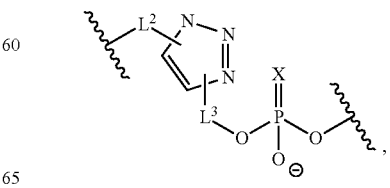

wherein:

X is O or S;

each of $L^2$, and $L^3$ is independently a bond, optionally substituted alkylene, or optionally substituted heteroalkylene;

In certain embodiments, $L^2$ is optionally substituted alkylene. In certain embodiments, $L^2$ is optionally substituted $C_{1-20}$ alkylene. In certain embodiments, $L^2$ is optionally substituted $C_{1-10}$ alkylene. In certain embodiments, $L^2$ is optionally substituted heteroalkylene. In certain embodiments, $L^2$ is optionally substituted $C_{1-20}$ heteroalkylene. In certain embodiments, $L^2$ is optionally substituted $C_{1-10}$ heteroalkylene. An optionally substituted heteroalkylene linker may contain one or more esters, amides, carbonates, carbamates, ureas, or other heteroatom-containing groups, in the linker. For example, in certain embodiments, $L^2$ is of the formula:

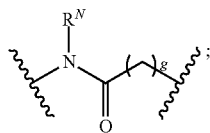

wherein $R^N$ and are as defined herein. In certain embodiments, $L^2$ is of one of the following formulae:

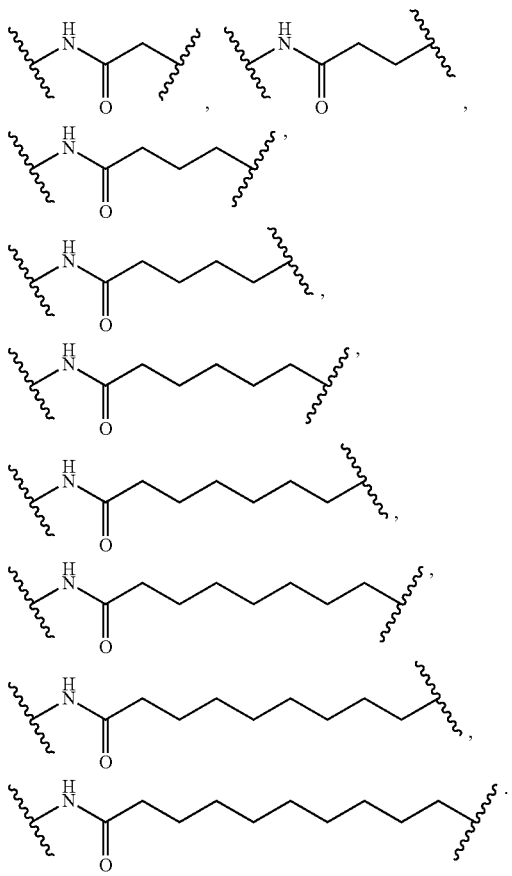

In certain embodiments, $L^2$ is of the formula:

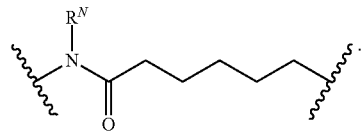

In certain embodiments, $L^2$ is of the formula:

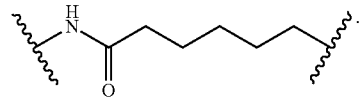 [SMILES: *CCCCCC(=O)N*]

In certain embodiments, $L^2$ is of the formula:

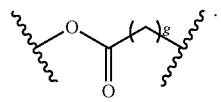

In certain embodiments, $L^3$ is a bond. In certain embodiments, $L^3$ is optionally substituted alkylene. In certain embodiments, $L^3$ is optionally substituted $C_{1-20}$ alkylene. In certain embodiments, $L^3$ is optionally substituted $C_{1-10}$ alkylene. In certain embodiments, $L^3$ is optionally substituted $C_{1-6}$ alkylene. In certain embodiments, $L^3$ is unsubstituted alkylene. In certain embodiments, $L^3$ is unsubstituted $C_{1-20}$ alkylene. In certain embodiments, $L^3$ is unsubstituted $C_{1-10}$ alkylene. In certain embodiments, $L^3$ is unsubstituted $C_{1-6}$ alkylene. In certain embodiments, $L^3$ is optionally substituted heteroalkylene. In certain embodiments, $L^3$ is optionally substituted $C_{1-20}$ heteroalkylene. In certain embodiments, $L^3$ is optionally substituted $C_{1-10}$ heteroalkylene. In certain embodiments, $L^3$ is optionally substituted $C_{1-6}$ heteroalkylene. For example, in certain embodiments, $L^3$ is of the formula:

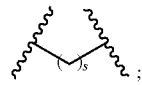

wherein s is as defined herein. In certain embodiments, $L^3$ is of one of the following formulae:

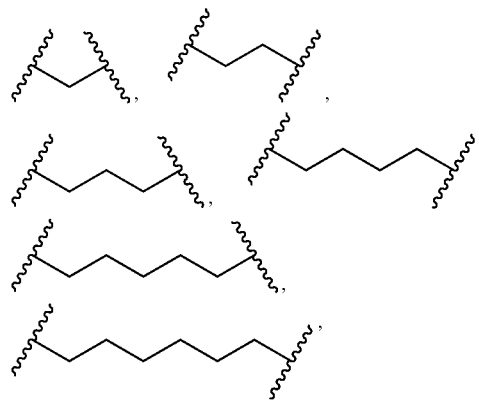

-continued

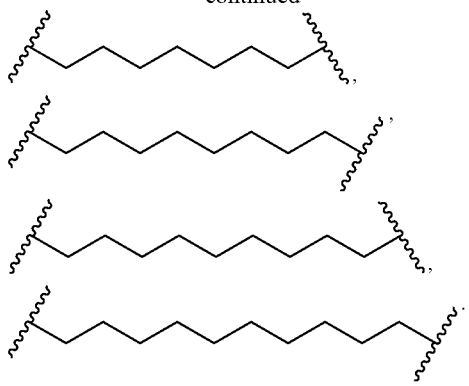

In certain embodiments, $L^3$ is of the following formula:

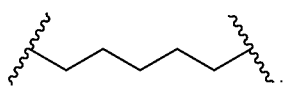 [SMILES: *CCCCC*]

In some embodiments, $L^T$ is of the following formula:

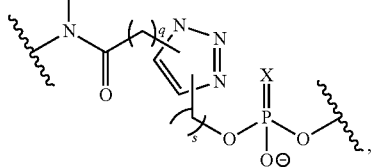

wherein:

$R^N$ is independently hydrogen, optionally substituted alkyl, optionally substituted acyl, or a nitrogen protecting group;

q is an integer from 0 to 20, inclusive; and s is an integer from 0 to 20, inclusive.

In some embodiments, $L^T$ is of the following formula:

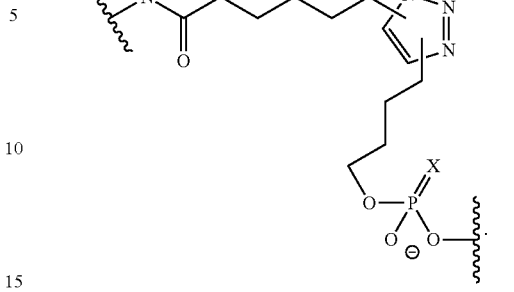

In some embodiments, $L^T$ is of the following formula:

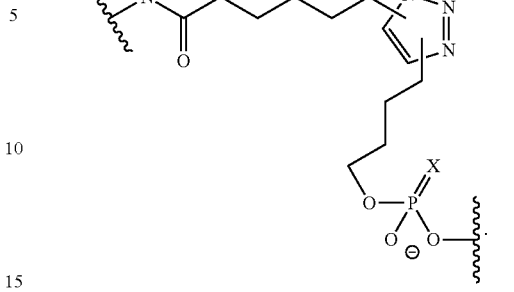

Other examples of linkers (e.g., for groups $L^A$, $L^B$, $L^C$, $L^1$, $L^2$, $L^3$, and $L^T$) contemplated include those disclosed in, e.g., U.S. Pat. Nos. 8,962,580; 8,828,956; 9,198,972; 9,181,549; and International Publication No. WO 2015/006740; International Publication No. WO 2013/166121; and International Publication No. WO 2014/172698; the entire contends of each of which is incorporated herein by reference.

For example, in certain embodiments, the group -$L^T$-T is of the following formulae:

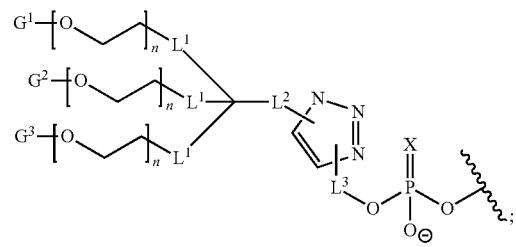

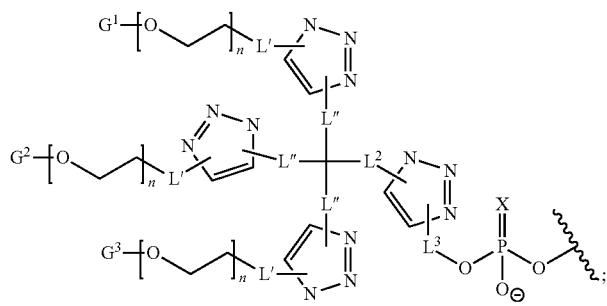

-continued
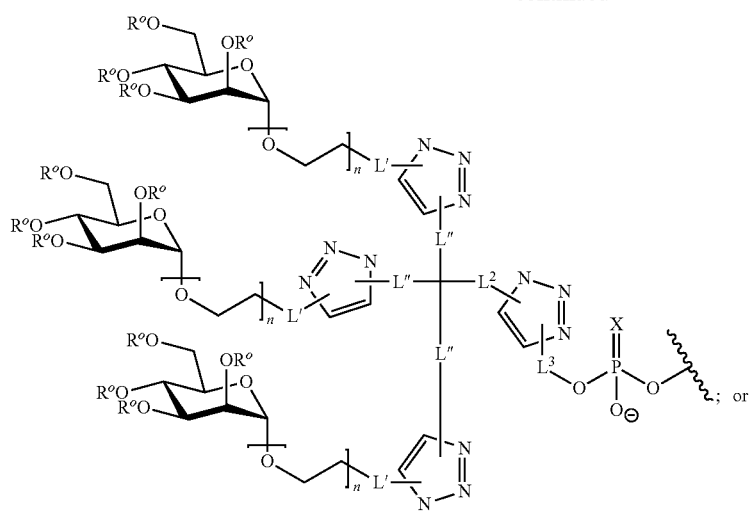
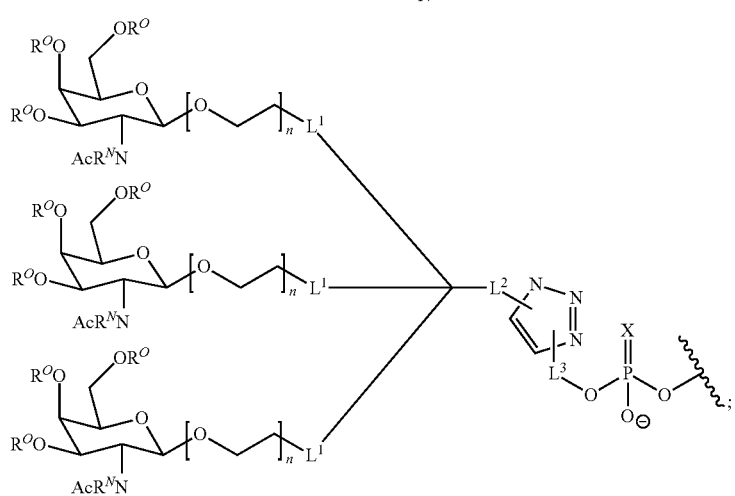
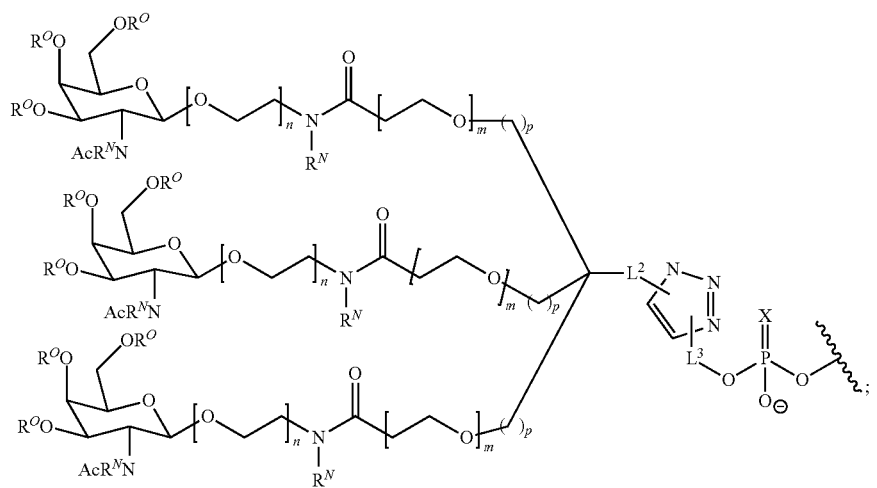

-continued
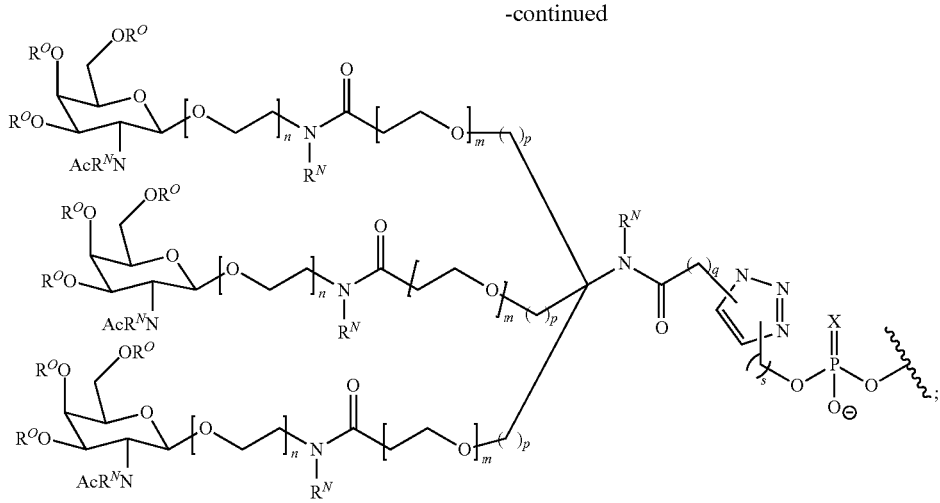
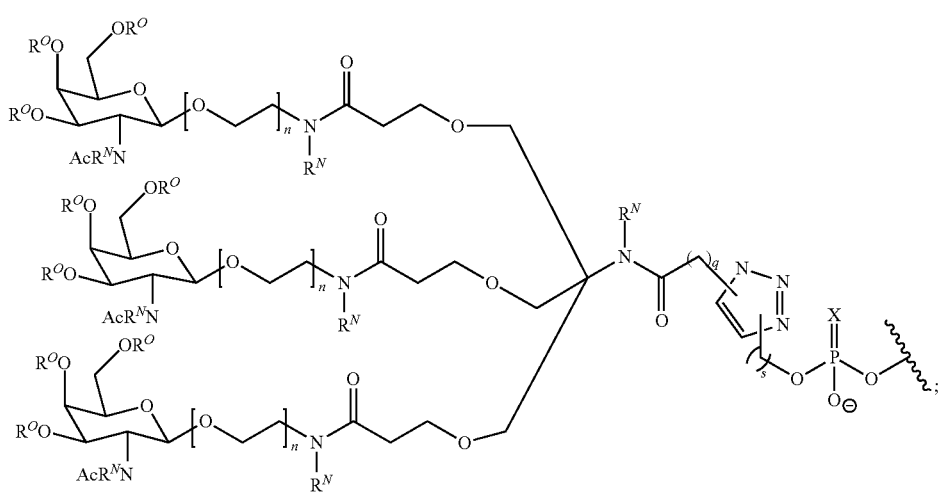
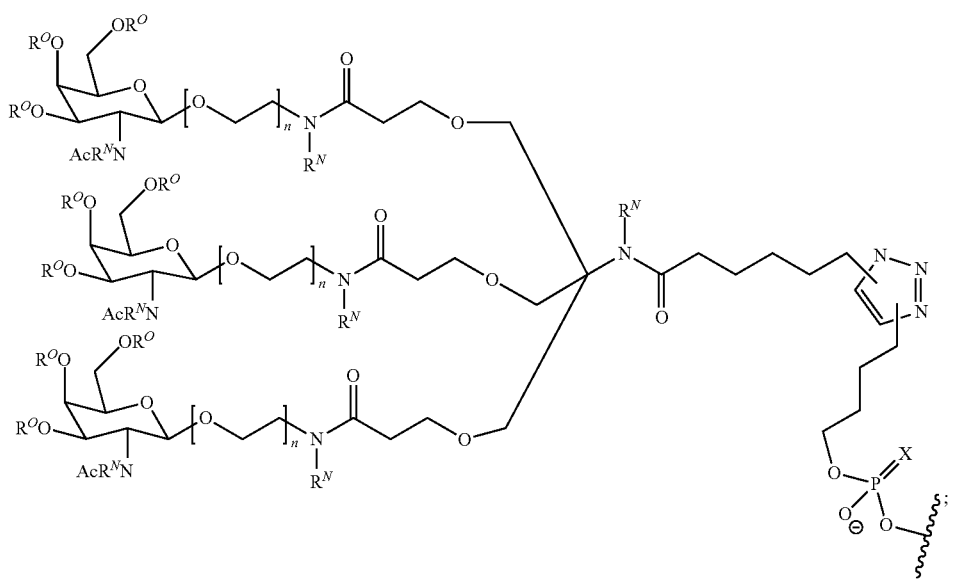

-continued

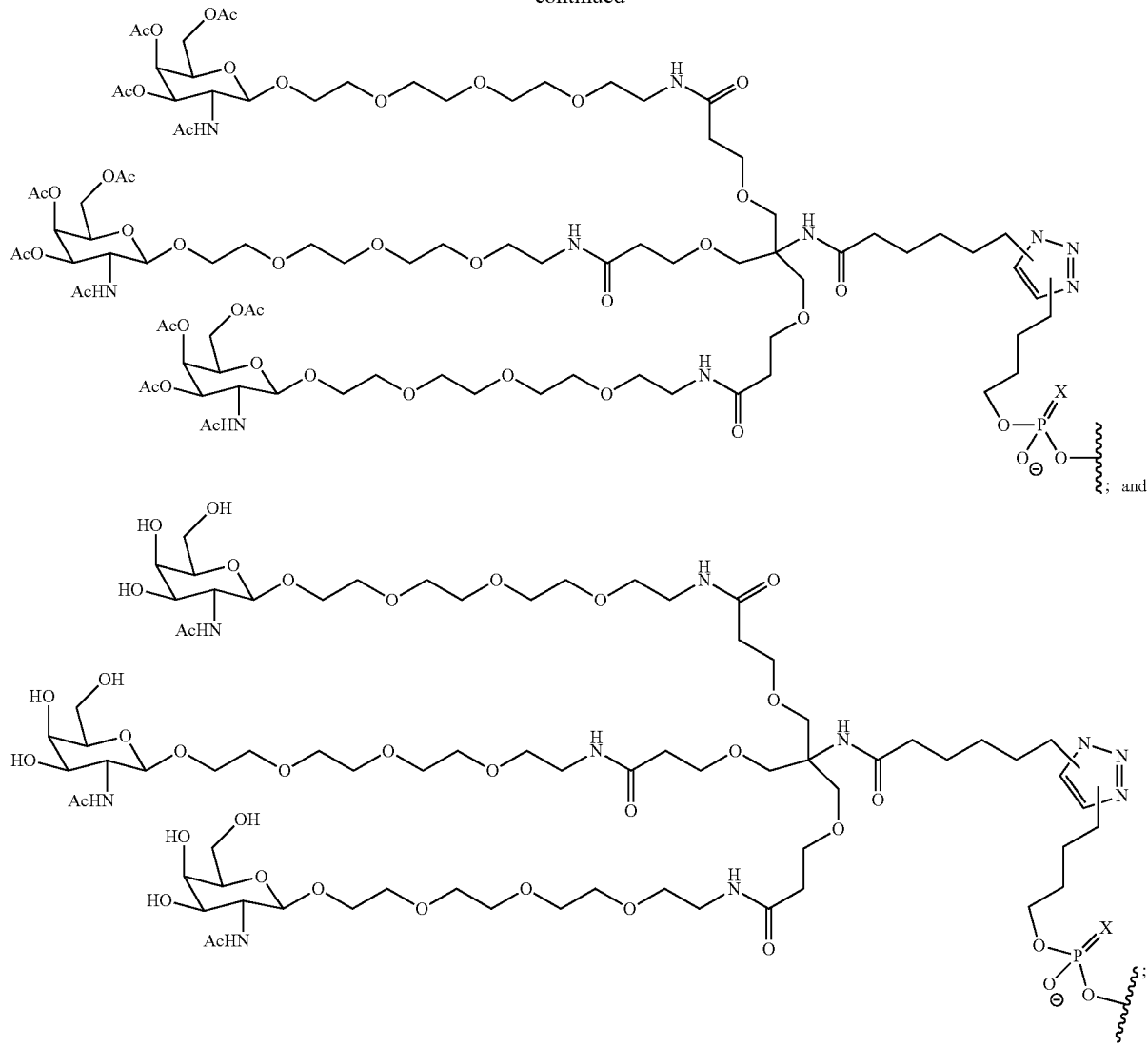

wherein $G^1$, $G^2$, $G^3$, $L^1$, $L^2$, $L^3$, L', L", $R^O$, $R^N$, X, m, n, p, q and s are as defined herein.

Oligonucleotides

In one aspect of the disclosure, oligonucleotides are provided, e.g., covalently linked to one or more targeting moieties as described herein, e.g., a GalNAc moiety as described herein. In some embodiments, oligonucleotides are provided for facilitating delivery of a nucleic acid (e.g., a synthetic mRNA) as described herein into a cell or tissue, such as a liver cell or liver tissue.

In some embodiments, oligonucleotides described herein are provided in a complex with, e.g., non-covalently associated with, a nucleic acid (e.g., a synthetic mRNA) as described herein. In some embodiments, the complex is outside of a cell. In some embodiments, the complex is inside of a cell. In some embodiments, the complex is represented by the following formula:

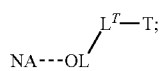

wherein:

NA is a nucleic acid as described herein;

OL is an oligonucleotide;

- - - - - represents one or more non-covalent bonds;

$L^T$ is a covalent bond or a linker moiety as described herein; and

T is a targeting moiety as described herein.

As described herein, the oligonucleotides are non-covalently associated to the nucleic acid via one or more non-covalent bonds (represented by - - - - -). In some embodiment, the oligonucleotides described herein are non-covalently associated with the nucleic acid via one or more Watson-Crick base pairing interactions. In some embodiments, the nucleic acid is hybridized to the oligonucleotide, e.g., under stringent hybridization conditions. In some embodiments, the oligonucleotides contain a region of complementarity that is complementary to a sequence a nucleic acid (e.g., a synthetic mRNA) as described herein. In some embodiments, the oligonucleotide contains a region of complementarity that is complementary to at least 5 (e.g., at least 5, at least 6, at least 7, at least 8, at least 9, at least 10, at least 11, at least 12, at least 13, at least 14, at least 15, at least 16, at least 17, at least 18, at least 19 or at least 20) contiguous nucleotides of the nucleic acid (e.g., the synthetic mRNA) as described herein.

The oligonucleotide may be single-stranded or double-stranded. Single-stranded oligonucleotides may include secondary structures, e.g., a loop or helix structure. In some embodiments, the oligonucleotide comprises at least one modified nucleotide or modified internucleoside linkage as described herein.

The oligonucleotide may have a sequence that does not contain guanosine nucleotide stretches (e.g., 3 or more, 4 or more, 5 or more, 6 or more consecutive guanosine nucleotides). In some embodiments, oligonucleotides having guanosine nucleotide stretches have increased non-specific binding and/or off-target effects, compared with oligonucleotides that do not have guanosine nucleotide stretches.

The oligonucleotide may have a sequence that has less than a threshold level of sequence identity with every sequence of nucleotides, of equivalent length, that map to a genomic position encompassing or in proximity to an off-target gene. For example, an oligonucleotide may be designed to ensure that it does not have a sequence that maps to genomic positions encompassing or in proximity with all known genes (e.g., all known protein coding genes) other than a sequence within the nucleic acid (e.g., the synthetic mRNA) as described herein). The threshold level of sequence identity may be 50%, 60%, 70%, 80%, 85%, 90%, 95%, 99% or 100% sequence identity.

The oligonucleotide may have a sequence that is has greater than 30% G-C content, greater than 40% G-C content, greater than 50% G-C content, greater than 60% G-C content, greater than 70% G-C content, or greater than 80% G-C content. The oligonucleotide may have a sequence that has up to 100% G-C content, up to 95% G-C content, up to 90% G-C content, or up to 80% G-C content. In some embodiments in which the oligonucleotide is 8 to nucleotides in length, all but 1, 2, 3, 4, or 5 of the nucleotides of the complementary sequence are cytosine or guanosine nucleotides. In some embodiments, the sequence to which the oligonucleotide is complementary comprises no more than 3 nucleotides selected from adenine and uracil.

In some embodiments, the region of complementarity of the oligonucleotide is complementary with 8 to 15, 8 to 30, 8 to 40, or 10 to 50, or 5 to 50, or 5 to 40, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of a nucleic acid (e.g., a synthetic mRNA) as described herein. In some embodiments, the region of complementarity is complementary with at least 5, at least 6, at least 7, at least 8, at least 9, at least 10, at least 11, at least 12, at least 13, at least 14, or at least 15 consecutive nucleotides of a nucleic acid (e.g., a synthetic mRNA) as described herein, optionally wherein the oligonucleotide is 8 to 30 nucleotides in length.

Complementary, as the term is used in the art, refers to the capacity for precise pairing between two nucleotides. For example, if a nucleotide at a certain position of an oligonucleotide is capable of hydrogen bonding with a nucleotide at the same position of a target sequence as described herein, then the oligonucleotide and the target sequence are considered to be complementary to each other at that position. The oligonucleotide and target sequence are complementary to each other when a sufficient number of corresponding positions in each molecule are occupied by nucleotides that can hydrogen bond with each other through their bases. Thus, "complementary" is a term which is used to indicate a sufficient degree of complementarity or precise pairing such that stable and specific binding occurs between the oligonucleotide and target sequence. For example, if a base at one position of an oligonucleotide is capable of hydrogen bonding with a base at the corresponding position of target sequence, then the bases are considered to be complementary to each other at that position. 100% complementarity is not required.

The oligonucleotide may be at least 70% complementary to (optionally one of at least 75%, 80%, 85%, 90%, 91%, 92%, 93%, 94%, 95%, 96%, 97%, 98%, 99% or 100% complementary to) the consecutive nucleotides of a target sequence as described herein. In some embodiments the oligonucleotide may contain 1, 2 or 3 base mismatches compared to the portion of the consecutive nucleotides of the target sequence. In some embodiments the oligonucleotide may have up to 3 mismatches over 15 bases, or up to 2 mismatches over 10 bases.

It is understood in the art that a complementary nucleotide sequence need not be 100% complementary to that of its target to be specifically hybridizable or specific for a target molecule. In some embodiments, a complementary nucleic acid sequence for purposes of the present disclosure is specifically hybridizable or specific for the target sequence when binding of the complementary nucleic acid sequence to a target sequence interferes with the normal function of the target by causing a loss of activity and/or expression and there is a sufficient degree of complementarity to avoid non-specific binding of the complementary nucleic acid sequence to non-target sequences under conditions in which avoidance of non-specific binding is desired, e.g., under physiological conditions in the case of in vivo assays or therapeutic treatment, and in the case of in vitro assays, under conditions in which the assays are performed under suitable conditions of stringency.

In some embodiments, the oligonucleotide is up to 7, up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27, up to 28, up to 29, up to 30, up to 35, up to 40, up to 45, or up to 50 nucleotides in length. In some embodiments, the oligonucleotide is 5 to 50, 6 to 50, 7 to 50, 8 to 50, 9 to 50, 10 to 50, 12 to 50, 5 to 30, 6 to 30, 7 to 30, 8 to 30, 9 to 30, 10 to 30, 12 to 30, 5 to 20, 6 to 20, 7 to 20, 8 to 20, 9 to 20, 10 to 20, 12 to 20, 5 to 15, 6 to 15, 7 to 15, 8 to 15, 9 to 15, 10 to 15 or 12 to 15 nucleotides in length. In some embodiments, the oligonucleotide is 8 to 30 or 8 to 20 nucleotides in length.

Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

In some embodiments, any one or more thymidine (T) nucleotides (or modified nucleotide thereof) or uridine (U) nucleotides (or a modified nucleotide thereof) in a sequence provided herein, including a sequence provided in the sequence listing, may be replaced with any other nucleotide suitable for base pairing (e.g., via a Watson-Crick base pair) with an adenosine nucleotide. In some embodiments, any one or more thymidine (T) nucleotides (or modified nucleotide thereof) or uridine (U) nucleotides (or a modified nucleotide thereof) in a sequence provided herein, including a sequence provided in the sequence listing, may be suitably replaced with a different pyrimidine nucleotide or vice versa. In some embodiments, any one or more thymidine (T) nucleotides (or modified nucleotide thereof) in a sequence provided herein, including a sequence provided in the sequence listing, may be suitably replaced with a uridine (U) nucleotide (or a modified nucleotide thereof) or vice versa.

In some embodiments, GC content of the oligonucleotide is preferably between about 30-60%. Contiguous runs of three or more Gs or Cs may not be preferable in some embodiments. Accordingly, in some embodiments, the oligonucleotide does not comprise a stretch of three or more guanosine nucleotides.

Oligonucleotide Structure and Modifications

The oligonucleotides described herein (e.g., covalently linked to a targeting moiety such as a GalNAc moiety) may be modified, e.g., comprise a modified sugar moiety, a modified internucleoside linkage, a modified nucleotide and/or combinations thereof. In addition, the oligonucleotides may exhibit one or more of the following properties: do not mediate alternative splicing; are not immune stimulatory; are nuclease resistant; have improved cell uptake compared to unmodified oligonucleotides; are not toxic to cells or mammals; or have improved endosomal exit. The nucleic acids described herein (e.g., synthetic mRNAs) may also be modified, e.g., comprise a modified sugar moiety, a modified internucleoside linkage, a modified nucleotide and/or combinations thereof.

Any of the oligonucleotides disclosed herein may be linked to one or more other oligonucleotides disclosed herein by a linker, e.g., a cleavable linker.

Oligonucleotides and nucleic acids as described herein can be stabilized against nucleolytic degradation such as by the incorporation of a modification, e.g., a nucleotide modification. For example, nucleic acid sequences of the disclosure may include a phosphorothioate at least the first, second, or third internucleoside linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-0 atom and the 4'-C atom.

Any of the modified chemistries or formats of oligonucleotides described herein can be combined with each other, and that one, two, three, four, five, or more different types of modifications can be included within the same molecule.

In some embodiments, an oligonucleotide or nucleic acid as described herein may comprise one or more modified nucleotides (also referred to herein as nucleotide analogs). In some embodiments, the oligonucleotide may comprise at least one ribonucleotide, at least one deoxyribonucleotide, and/or at least one bridged nucleotide. In some embodiments, the oligonucleotide or nucleic acid may comprise a bridged nucleotide, such as a locked nucleic acid (LNA) nucleotide, a constrained ethyl (cEt) nucleotide, or an ethylene bridged nucleic acid (ENA) nucleotide. Examples of such nucleotides are disclosed herein and known in the art. In some embodiments, the oligonucleotide comprises a nucleotide analog disclosed in one of the following United States patent or patent application Publications: U.S. Pat. Nos. 7,399,845, 7,741,457, 8,022,193, 7,569,686, 7,335, 765, 7,314,923, 7,335,765, and 7,816,333, US 2011/0009471, the entire contents of each of which are incorporated herein by reference for all purposes. The oligonucleotide may have one or more 2' O-methyl nucleotides. The oligonucleotide may consist entirely of 2' O-methyl nucleotides.

In some embodiments, the oligonucleotide or nucleic acid has one or more nucleotide analogues. For example, the oligonucleotide may have at least one nucleotide analogue that results in an increase in $T_m$ of the oligonucleotide in a range of 1° C., 2° C., 3° C., 4° C., or 5° C. compared with an oligonucleotide that does not have the at least one nucleotide analogue. The oligonucleotide may have a plurality of nucleotide analogues that results in a total increase in $T_m$ of the oligonucleotide in a range of 2° C., 3° C., 4° C., 5° C., 6° C., 7° C., 8° C., 9° C., 10° C., 15° C., 20° C., 25° C., 30° C., 35° C., 40° C., 45° C. or more compared with an oligonucleotide that does not have the nucleotide analogue.

The oligonucleotide may be of up to 50 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the oligonucleotide are nucleotide analogues. The oligonucleotide may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide are nucleotide analogues.

The oligonucleotide may be of 8 to 15 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the oligonucleotide are nucleotide analogues. Optionally, the oligonucleotides may have every nucleotide except 1, 2, 3, 4, 5, 6, 7, 8, 9, or 10 nucleotides modified.

The oligonucleotide or nucleic acid may consist entirely of bridged nucleotides (e.g., LNA nucleotides, cEt nucleotides, ENA nucleotides). The oligonucleotide or nucleic acid may comprise alternating deoxyribonucleotides and 2'-fluoro-deoxyribonucleotides. The oligonucleotide or nucleic acid may comprise alternating deoxyribonucleotides and 2'-O-methyl nucleotides. The oligonucleotide or nucleic acid may comprise alternating deoxyribonucleotides and ENA nucleotide analogues. The oligonucleotide may comprise alternating deoxyribonucleotides and LNA nucleotides. The oligonucleotide or nucleic acid may comprise alternating LNA nucleotides and 2'-O-methyl nucleotides. The oligonucleotide or nucleic acid may have a 5' nucleotide that is a bridged nucleotide (e.g., a LNA nucleotide, cEt nucleotide, ENA nucleotide). The oligonucleotide or nucleic acid may have a 5' nucleotide that is a deoxyribonucleotide.

The oligonucleotide or nucleic acid may comprise deoxyribonucleotides flanked by at least one bridged nucleotide (e.g., a LNA nucleotide, cEt nucleotide, ENA nucleotide) on each of the 5' and 3' ends of the deoxyribonucleotides. The oligonucleotide may comprise deoxyribonucleotides flanked by 1, 2, 3, 4, 5, 6, 7, 8 or more bridged nucleotides (e.g., LNA nucleotides, cEt nucleotides, ENA nucleotides) on each of the 5' and 3' ends of the deoxyribonucleotides. The 3' position of the oligonucleotide or nucleic acid may have a 3' hydroxyl group. The 3' position of the oligonucleotide or nucleic acid may have a 3' thiophosphate.

The oligonucleotide or nucleic acid may be conjugated with a label. For example, the oligonucleotide may be conjugated with a biotin moiety, cholesterol, Vitamin A, folate, sigma receptor ligands, aptamers, peptides, such as CPP, hydrophobic molecules, such as lipids, ASGPR or dynamic polyconjugates and variants thereof at its 5' or 3' end.

In some embodiments, the oligonucleotide or nucleic acid comprises one or more modifications comprising: a modified sugar moiety, and/or a modified internucleoside linkage, and/or a modified nucleotide and/or combinations thereof. It is not necessary for all positions in a given oligonucleotide or nucleic acid to be uniformly modified, and in fact more than one of the modifications described herein may be incorporated in a single oligonucleotide or nucleic acid or even at within a single nucleoside within an oligonucleotide or nucleic acid.

In some embodiments, the oligonucleotides or nucleic acids are chimeric oligonucleotides that contain two or more chemically distinct regions, each made up of at least one nucleotide. These oligonucleotides or nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric oligonucleotides or nucleic acids of the disclosure may be formed as composite structures of two or more oligonucleotides, modified oligonucleotides, oligonucleosides and/or oligonucleotide mimetics as described above. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the oligonucleotide or nucleic acid comprises at least one nucleotide modified at the 2' position of the sugar, preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher $T_m$ (i.e., higher target binding affinity) than 2'-deoxyoligonucleotides against a given target.

A number of nucleotide modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides or nucleic acids include those comprising modified backbones, for example, modified internucleoside linkages such as phosphorothioates, phosphotriesters, methyl phosphonates, short chain alkyl or cycloalkyl intersugar linkages or short chain heteroatomic or heterocyclic intersugar linkages. In some embodiments, oligonucleotides or nucleic acids may have phosphorothioate backbones; heteroatom backbones, such as methylene(methylimino) or MMI backbones; amide backbones (see De Mesmaeker et al. Ace. Chem. Res. 1995, 28:366-374); morpholino backbones (see Summerton and Weller, U.S. Pat. No. 5,034,506); or peptide nucleic acid (PNA) backbones (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

In some embodiments, the oligonucleotide is an oligonucleotide mimetic. Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues. Arabinonucleosides are stereoisomers of ribonucleosides, differing only in the configuration at the 2'-position of the sugar ring. In some embodiments, a 2'-arabino modification is 2'-F arabino. In some embodiments, the modified oligonucleotide is 2'-fluoro-D-arabinonucleic acid (FANA) (as described in, for example, Lon et al., Biochem., 41:3457-3467, 2002 and Min et al., Bioorg. Med. Chem. Lett., 12:2651-2654, 2002; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide.

PCT Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Patent Publication No. WO 2005/042777, Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties). Preferred ENAs include, but are not limited to, 2'-O,4'-C-ethylene-bridged nucleic acids.

Examples of LNAs are described in WO/2008/043753 and include compounds of the following general formula.

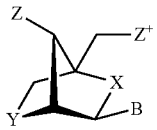

where X and Y are independently selected among the groups —O—, —S—, —N(H)—, N(R)—, —CH$_2$— or —CH— (if part of a double bond), —CH$_2$—O—, —CH$_2$—S—, —CH$_2$—N(H)—, —CH$_2$—N(R)—, —CH$_2$—CH$_2$— or —CH$_2$—CH— (if part of a double bond), —CH═CH—, where R is selected from hydrogen and C$_{1-4}$-alkyl; Z and Z* are independently selected among an internucleoside linkage, a terminal group or a protecting group; B constitutes a natural or non-natural nucleotide base moiety; and the asymmetric groups may be found in either orientation.

In some embodiments, the LNA used in the oligonucleotides or nucleic acids described herein comprises at least one LNA unit according any of the formulas

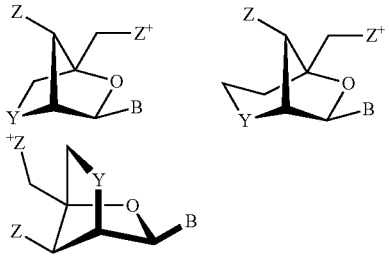

wherein Y is —O—, —O—, —NH—, or N(R$^H$); Z and Z* are independently selected among an internucleoside linkage, a terminal group or a protecting group; B constitutes a natural or non-natural nucleotide base moiety, and RH is selected from hydrogen and C$_{1-4}$-alkyl.

In some embodiments, the Locked Nucleic Acid (LNA) used in the oligonucleotides or nucleic acids described herein comprises at least one Locked Nucleic Acid (LNA) unit according any of the formulas shown in Scheme 2 of PCT/DK2006/000512.

In some embodiments, the LNA used an oligonucleotide or nucleic acid as described herein comprises internucleoside linkages selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, where R$^H$ is selected from hydrogen and C$_{1-4}$-alkyl.

Specifically preferred LNA units are shown below:

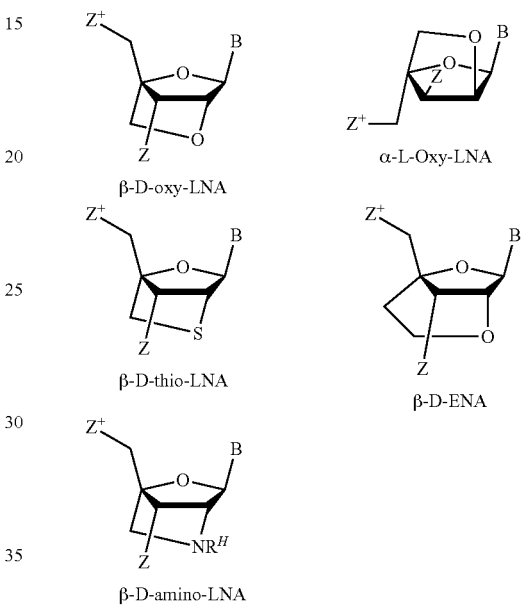

The term "thio-LNA" comprises a locked nucleotide in which at least one of X or Y in the general formula above is selected from S or —CH$_2$—S—. Thio-LNA can be in both beta-D and alpha-L-configuration.

The term "amino-LNA" comprises a locked nucleotide in which at least one of X or Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which at least one of X or Y in the general formula above represents —O— or —CH$_2$—O—. Oxy-LNA can be in both beta-D and alpha-L-configuration.

The term "ena-LNA" comprises a locked nucleotide in which Y in the general formula above is —CH$_2$—O— (where the oxygen atom of —CH$_2$—O— is attached to the 2'-position relative to the base B).

LNAs are described in additional detail herein.

One or more substituted sugar moieties can also be included, e.g., one of the following at the 2' position: OH, SH, SCH$_3$, F, OCN, OCH$_3$OCH$_3$, OCH$_3$O(CH$_2$)n CH$_3$, O(CH$_2$)n NH$_2$ or O(CH$_2$)n CH$_3$ where n is from 1 to about 10; C$_1$ to C$_{10}$ lower alkyl, alkoxyalkoxy, substituted lower alkyl, alkaryl or aralkyl; Cl; Br; CN; CF$_3$; OCF$_3$; O—, S—, or N-alkyl; O—, S—, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$CH$_2$OCH$_3$, also known as 2'-O-(2-methoxyethyl)](Martin et al, Helv. Chim. Acta, 1995, 78, 486). Other preferred modifications include 2'-methoxy (2'-O—CH$_3$), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides and nucleic acids described herein can also include, additionally or alternatively, nucleobase (often referred to in the art simply as "base") modifications or substitutions. In some embodiments, an oligonucleotide described herein includes at least one nucleobase that is not an unmodified or natural nucleobase. As used herein, "unmodified" or "natural" nucleobases include adenine (A), guanine (G), thymine (T), cytosine (C) and uracil (U). Modified nucleobases include, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-77; and Gebeyehu, G., et al. Nucl. Acids Res., 15:4513 (1987)). A "universal" base known in the art, e.g., inosine, can also be included. 5-Me-C substitutions have been shown to increase nucleic acid duplex stability by 0.6-1.2° C. (Sanghvi, in Crooke, and Lebleu, eds., Antisense Research and Applications, CRC Press, Boca Raton, 1993, pp. 276-278) and may be used as base substitutions.

In some embodiments, both a sugar and an internucleoside linkage, i.e., the backbone, of the nucleotide units are replaced with modified groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Oligonucleotides and nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in "The Concise Encyclopedia of Polymer Science And Engineering", pages 858-859, Kroschwitz, ed. John Wiley & Sons, 1990; those disclosed by Englisch et al., Angewandle Chemie, International Edition, 1991, 30, page 613, and those disclosed by Sanghvi, Chapter 15, Antisense Research and Applications," pages 289-302, Crooke, and Lebleu, eds., CRC Press, 1993. Certain of these nucleobases are particularly useful for increasing the binding affinity of the oligonucleotides described herein. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, et al., eds, "Antisense Research and Applications," CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175,273; 5,367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the oligonucleotides or nucleic acids are chemically linked to one or more moieties or conjugates that enhance the activity, cellular distribution, or cellular uptake of the oligonucleotide. For example, one or more oligonucleotides, of the same or different types, can be conjugated to each other; or oligonucleotides can be conjugated to targeting moieties with enhanced specificity for a cell type or tissue type. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference. Additional targeting moieties are discussed in more detail herein.

These moieties or conjugates can include conjugate groups covalently bound to functional groups such as primary or secondary hydroxyl groups. Conjugate groups of the disclosure include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this disclosure, include groups that improve uptake, enhance resistance to degradation, and/or strengthen sequence-specific hybridization with the target nucleic acid. Groups that enhance the pharmacokinetic properties, in the context of this disclosure, include groups that improve uptake, distribution, metabolism or excretion of the compounds of the present disclosure. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some embodiments, oligonucleotide or nucleic acid modification includes modification of the 5' or 3' end of the oligonucleotide or nucleic acid. In some embodiments, the 3' end of the oligonucleotide or nucleic acid comprises a hydroxyl group or a thiophosphate. It should be appreciated that additional molecules (e.g. a biotin moiety or a fluorophor) can be conjugated to the 5' or 3' end of the oligonucleotide or nucleic acid. In some embodiments, the oligonucleotide or nucleic acid comprises a biotin moiety conjugated to the 5' nucleotide.

In some embodiments, the oligonucleotide or nucleic acid comprises locked nucleic acids (LNA), ENA modified nucleotides, 2'-O-methyl nucleotides, or 2'-fluoro-deoxyribonucleotides. In some embodiments, the oligonucleotide comprises alternating deoxyribonucleotides and 2'-fluoro-deoxyribonucleotides. In some embodiments, the oligonucleotide or nucleic acid comprises alternating deoxyribonucleotides and 2'-O-methyl nucleotides. In some embodiments, the oligonucleotide or nucleic acid comprises alternating deoxyribonucleotides and ENA modified nucleotides. In some embodiments, the oligonucleotide or nucleic acid comprises alternating deoxyribonucleotides and locked nucleic acid nucleotides. In some embodiments, the oligonucleotide or nucleic acid comprises alternating locked nucleic acid nucleotides and 2'-O-methyl nucleotides. In some embodiments, the oligonucleotide or nucleic acid comprises locked nucleic acid nucleotides flanked by 2'-O-methyl nucleotides on the 5' and/or 3' end.

In some embodiments, the 5' nucleotide of the oligonucleotide or nucleic acid is a deoxyribonucleotide. In some embodiments, the 5' nucleotide of the oligonucleotide or nucleic acid is a locked nucleic acid nucleotide. In some embodiments, the nucleotides of the oligonucleotide or nucleic acid comprise deoxyribonucleotides flanked by at least one locked nucleic acid nucleotide on each of the 5' and 3' ends of the deoxyribonucleotides. In some embodiments, the nucleotide at the 3' position of the oligonucleotide or nucleic acid has a 3' hydroxyl group or a 3' thiophosphate.

In some embodiments, the oligonucleotide or nucleic acid comprises phosphorothioate internucleoside linkages. In some embodiments, the oligonucleotide or nucleic acid comprises phosphorothioate internucleoside linkages between at least two nucleotides. In some embodiments, the oligonucleotide or nucleic acid comprises phosphorothioate internucleoside linkages between all nucleotides.

It should be appreciated that the oligonucleotide or nucleic acid can have any combination of modifications as described herein.

Oligonucleotide Types

In some aspects, oligonucleotides described herein may be of a specific type or chemistry pattern such as a mixmer, a single stranded RNA, a single stranded DNA, an aptamer, or an oligonucleotide mimetic. In some embodiment, oligonucleotides described herein are not gapmers, siRNAs, ribozymes or microRNAs, or any other type of oligonucleotide that results in degradation of the target nucleic acid once delivered to a cell or tissue.

In some embodiments, an oligonucleotide described herein may be a mixmer or comprise a mixmer sequence pattern. The term 'mixmer' refers to oligonucleotides which comprise both naturally and non-naturally occurring nucleotides or comprise two different types of non-naturally occurring nucleotides. Mixmers are generally known in the art to have a higher binding affinity than unmodified oligonucleotides and may be used to specifically bind a target molecule, e.g., to block a binding site on the target molecule. Generally, mixmers do not recruit an RNAse to the target molecule and thus do not promote cleavage of the target molecule.

In some embodiments, the mixmer comprises or consists of a repeating pattern of nucleotide analogues and naturally occurring nucleotides, or one type of nucleotide analogue and a second type of nucleotide analogue. However, it is to be understood that the mixmer need not comprise a repeating pattern and may instead comprise any arrangement of nucleotide analogues and naturally occurring nucleotides or any arrangement of one type of nucleotide analogue and a second type of nucleotide analogue. It is to be understood that a pattern, in general, refers to a pattern of modifications or lack thereof, and not to a pattern of A, T, C, G, or U nucleotides. The repeating pattern, may, for instance be every second or every third nucleotide is a nucleotide analogue, such as LNA, and the remaining nucleotides are naturally occurring nucleotides, such as DNA, or are a 2' substituted nucleotide analogue such as 2'-O-methyl, 2'MOE or 2' fluoro analogues, or any other nucleotide analogues described herein. It is recognized that the repeating pattern of nucleotide analogues, such as LNA units, or 2'-O-methyl, 2'MOE or 2' fluoro analogues, may be combined with nucleotide analogues at fixed positions—e.g. at the 5' or 3' termini.

In some embodiments, the mixmer does not comprise a region of more than 5, more than 4, more than 3, or more than 2 consecutive naturally occurring nucleotides, such as DNA nucleotides. In some embodiments, the mixmer comprises at least a region consisting of at least two consecutive nucleotide analogues, such as at least two consecutive LNAs. In some embodiments, the mixmer comprises at least a region consisting of at least three consecutive nucleotide analogue units, such as at least three consecutive LNAs.

In some embodiments, the mixmer does not comprise a region of more than 7, more than 6, more than 5, more than 4, more than 3, or more than 2 consecutive nucleotide analogues, such as LNAs. It is to be understood that the LNA units may be replaced with other nucleotide analogues, such as those referred to herein.

In some embodiments, the mixmer contains a modified nucleotide, e.g., an LNA, at the 5' end. In some embodiments, the mixmer contains a modified nucleotide, e.g., an LNA, at the first two positions, counting from the 5' end.

In some embodiments, the mixmer is incapable of recruiting RNAseH. Oligonucleotides that are incapable of recruiting RNAseH are well known in the literature, in example see WO2007/112754, WO2007/112753, or PCT/DK2008/000344. Mixmers may be designed to comprise a mixture of affinity enhancing nucleotide analogues, such as in non-limiting example LNA nucleotides and 2'-O-methyl nucleotides. In some embodiments, the mixmer comprises modified internucleoside linkages (e.g., phosphorothioate internucleoside linkages or other linkages) between at least two, at least three, at least four, at least five or more nucleotides.

In some embodiments, a mixmer is 4 to 40 nucleotides (e.g., 4 to 40, 4 to 35, 4 to 30, 4 to 25, 4 to 20, 4 to 15, 4 to 10, 5 to 40, 5 to 35, 5 to 30, 5 to 25, 5 to 20, 5 to 15, or 5 to 10), in length having the general formula:

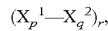

$$(X_p^1 - X_q^2)_r,$$

wherein each instance of $X^4$ is a modified or unmodified nucleotide described herein (e.g., a modified or unmodified ribonucleotide described herein), wherein each instance of $X^5$ is a deoxyribonucleotide, wherein p and q are independently 0 or 1, reflecting the number of instances of $X^1$ and $X^2$, respectively, wherein at least one of $X^1$ and $X^2$ is present in each instance of the unit, $(X_p^1 - X_q^2)$, wherein r is an integer from 2 to 20 reflecting the number of instances of the unit, $(X_p^1 - X_q^2)$, linked together through internucleotide linkages, wherein the protecting oligonucleotide or region does not contain a sequence of more than 5 consecutive deoxyribonucleotides, and wherein the symbol "-" denotes an internucleotide linkage.

A mixmer may be produced using any method known in the art or described herein. Representative U.S. patents, U.S. patent publications, and PCT publications that teach the preparation of mixmers include U.S. patent publication Nos. US2006/0128646, US2009/0209748, US2009/0298916, US2011/0077288, and US2012/0322851, and U.S. Pat. No. 7,687,617.

In some embodiments, the oligonucleotide is an oligonucleotide mimetic, such as a morpholino-based oligomeric compound, a cyclohexenyl nucleic acid oligonucleotide mimetics, or peptide nucleic acid (PNA) compound. In some embodiments, the oligonucleotide is a morpholino. Morpholinos are described, e.g., in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Producing Candidate Oligonucleotides

In some embodiments, methods are provided for producing candidate oligonucleotides that may be useful for facilitating delivery of nucleic acid as described herein. Generally, the oligonucleotides contain a region of complementarity (e.g., at least 5 nucleotides) that is complementary to a target sequence within a nucleic acid (e.g., a synthetic mRNA) as described herein.

In some embodiments, the oligonucleotides are designed by determining a region of a target sequence; producing an oligonucleotide that has a region of complementarity that is complementary with a plurality of (e.g., at least 5) contiguous nucleotides of the region of the target sequence; and determining whether associating the oligonucleotide with a nucleic acid (e.g., a synthetic mRNA) as described herein facilitates or enhances delivery of the nucleic acid to a cell or tissue, e.g., a liver cell or liver tissue.

In some embodiments, methods are provided for obtaining one or more oligonucleotides for facilitating delivery of a nucleic acid (e.g., a synthetic mRNA) as described herein that further involve producing a plurality of different oligonucleotides, in which each oligonucleotide has a region of complementarity that is complementary with a plurality of (e.g., at least 5) contiguous nucleotides in one or more target sequences in the nucleic acid (e.g., a synthetic mRNA); covalently linking a targeting moiety (e.g., a GalNAc moiety) to the oligonucleotide and subjecting each of the different oligonucleotides to an assay that assesses whether use of one or more oligonucleotides from the plurality facilitates or enhances delivery of a nucleic acid (e.g., synthetic mRNA) when the one or more oligonucleotides are associated with the nucleic acid; and obtaining one or more oligonucleotides that facilitate or enhance delivery of the nucleic acid in the assay.

Methods for Delivery to Subjects

Other aspects of the disclosure relate to methods of treating a disease or condition in a subject (e.g. a human) by administering a complex, composition or pharmaceutical preparation comprising an oligonucleotide and a nucleic acid (e.g., a synthetic mRNA) as described herein to the subject. In some embodiments, the disease or condition is a neurological condition, autoimmune disease, inflammatory disease, liver disease, proliferative disease, ocular condition, cardiovascular disease, metabolic condition, or hematological disease.

Other aspects of the disclosure relate to method of modulating (e.g., increasing or decreasing) gene expression in a subject (e.g. a human) by administering a complex, composition or pharmaceutical preparation comprising an oligonucleotide and a nucleic acid (e.g., a synthetic mRNA) as described herein to the subject. In some embodiments, methods comprise administering to a subject (e.g. a human) a complex, composition or pharmaceutical preparation comprising an oligonucleotide and a nucleic acid (e.g., a synthetic mRNA) as described herein to increase mRNA and/or protein levels of a target gene in the subject. In some embodiments, the target gene is a gene encoding a protein that is endogenously found in the subject and/or endogenously found in a healthy subject. In some embodiments, the target gene is synthetic and encodes a protein that is not endogenously found in the subject (e.g., a fusion protein or other synthetic protein). In some embodiments, the increase in mRNA and/or protein levels is at least 5%, 10%, 20%, 30%, 40%, 50%, 60%, 70%, 80%, 90%, 100%, 200%, or more, higher than the amount of a mRNA and/or protein in the subject before administering.

In some embodiments, the methods involve treating a disease associated with decreased levels of expression or activity of a target gene in a subject, the method comprising administering a complex, composition or pharmaceutical preparation comprising an oligonucleotide and a nucleic acid (e.g., a synthetic mRNA) as described herein. In some embodiments, the disease is ornithine transcarbamylase (OTC) deficiency and the method comprises administering a complex, composition or pharmaceutical preparation comprising an oligonucleotide as described herein and a synthetic mRNA that encodes a OTC protein.

A subject can include a non-human mammal, e.g. mouse, rat, guinea pig, rabbit, cat, dog, goat, cow, or horse. In preferred embodiments, a subject is a human. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). Oligonucleotides and other nucleic acids such as synthetic mRNAs have been employed as therapeutic moieties in the treatment of disease states in animals, including humans. Oligonucleotides and other nucleic acids such as synthetic mRNAs can be useful therapeutic modalities that can be configured to be useful in treatment regimens for the treatment of cells, tissues and animals, especially humans.

Route of Delivery

The oligonucleotides and compositions described herein can be delivered to a subject by a variety of routes. Exemplary routes include: intrathecal, intraneural, intracerebral, intramuscular, oral, intravenous, intradermal, topical, rectal, parenteral, anal, intravaginal, intranasal, pulmonary, or ocular. In some embodiments, oligonucleotides and compositions described herein are delivered subcutaneously to a subject as described herein. The term "therapeutically effective amount" is the amount of active agent(s) (e.g., oligonucleotide and a nucleic acid as described herein) present in the composition that is needed to provide the desired level of gene expression in a cell or to provide a treatment effect in the subject to be treated, e.g., treatment of OTC deficiency. The term "physiologically effective amount" is that amount delivered to a subject to give the desired palliative or curative effect. The term "pharmaceutically acceptable carrier" means that the carrier can be administered to a subject with no significant adverse toxicological effects to the subject.

The oligonucleotides and nucleic acids and related complexes as described herein can be incorporated into pharmaceutical compositions (also referred to herein as a pharmaceutical preparation) suitable for administration. The terms "preparation," "composition" and "formulation" are used interchangeably herein. Such compositions typically include one or more species of oligonucleotide, one or more species of nucleic acid, and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present disclosure may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration. The route and site of administration may be chosen to enhance targeting.

Parenteral administration includes intravenous drip, subcutaneous, intraperitoneal or intramuscular injection, intrathecal or intraventricular administration. In some embodiments, parental administration involves administration directly to the site of disease.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

Pulmonary delivery compositions can be delivered by inhalation by the patient of a dispersion so that the composition, preferably oligonucleotides, within the dispersion can reach the lung where it can be readily absorbed through the alveolar region directly into blood circulation. Pulmonary delivery can be effective both for systemic delivery and for localized delivery to treat diseases of the lungs.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Suitable pH adjusters or buffers include organic salts prepared from organic acids and bases, such as sodium citrate, sodium ascorbate, and the like; sodium citrate is preferred. Pulmonary administration of a micellar oligonucleotide formulation may be achieved through metered dose spray devices with propellants such as tetrafluoroethane, heptafluoroethane, dimethylfluoropropane, tetrafluoropropane, butane, isobutane, dimethyl ether and other non-CFC and CFC propellants.

Exemplary devices include devices which are introduced into the vasculature, e.g., devices inserted into the lumen of a vascular tissue, or which devices themselves form a part of the vasculature, including stents, catheters, heart valves, and other vascular devices. These devices, e.g., catheters or stents, can be placed in the vasculature of the lung, heart, or leg.

In some embodiments, an oligonucleotide and nucleic acid as described herein (e.g., in a complex) are delivered naked or unpackaged. In some embodiments, an oligonucleotide and nucleic acid as described herein (e.g., in a complex) are delivered with a carrier. Exemplary carriers include polymer based carriers, such as polyethyleneimine (PEI) and multi-domain-block polymers, lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, dry powders, poly(D-arginine), nanodendrimers, starch-based delivery systems, micelles, emulsions, sol-gels, niosomes, plasmids, viruses, calcium phosphate nucleotides, aptamers, peptides, peptide conjugates, small-molecule targeted conjugates, and other vectorial tags. Also contemplated is the use of bionanocapsules and other viral capsid proteins assemblies as a suitable carrier. (Hum. Gene Ther. 2008 September; 19(9):887-95).

In some embodiments, an oligonucleotide and nucleic acid as described herein (e.g., in a complex) is formulated with a nanoparticle, such as a lipid nanoparticle. In some embodiments, the oligonucleotide is contained within or attached to a nanoparticle. In some embodiments, the lipid nanoparticle includes: (a) one or more cationic lipids, (b) one or more non-cationic lipids, (c) one or more conjugated lipids that inhibits aggregation of particles, or a combination thereof. Exemplary nanoparticles suitable for use with oligonucleotides are disclosed in PCT application number PCT/US2016/058842.

Dosage

In one aspect, the disclosure features a method of administering an oligonucleotide and nucleic acid as described herein (e.g., in a complex or composition) to a cell or a subject. In some embodiments, the cell is in vivo, such as a liver cell in vivo. In some embodiments, the cell is in vitro, such as a liver cell in vitro. In some embodiments, the cell is ex vivo, such as an ex vivo liver cell.

For oligonucleotides, the defined amount delivered can be an amount effective to facilitate or enhance delivery of a nucleic acid (e.g., a synthetic mRNA) as described herein into a cell or a tissue, such as a liver cell or tissue. For a nucleic acid (e.g., a synthetic mRNA) as described herein, the defined amount delivered can be an amount effective to result in a biological effect in a cell or tissue, such as increasing levels of an mRNA and/or protein in a cell. For a composition as described herein, e.g., comprising a nucleic acid as described herein and an oligonucleotide as described herein, the defined amount delivered can be an amount to modulate target gene expression in a cell or subject or to treat or prevent a disease or condition is a subject, e.g., a disease or condition associated with or caused by a decreased level of expression of a target gene in a subject, such as OTC deficiency.

In some embodiments, the unit dose is administered or delivered daily. In some embodiments, less frequently than once a day, e.g., less than every 2, 4, 8 or 30 days. In some embodiments, a unit dose is administered once per month, once per two months, once per three months or once per four months. In another embodiment, the unit dose is not administered or delivered with a frequency (e.g., not a regular frequency). For example, the unit dose may be administered or delivered a single time. In some embodiments, the unit dose is administered or delivered more than once a day, e.g., once an hour, two hours, four hours, eight hours, twelve hours, etc. Further, the treatment regimen may last for a period of time which will vary depending upon the nature of the particular disease, its severity and the overall condition of the patient. Following treatment, the subject can be monitored for changes in his condition and for alleviation of the symptoms of the disease state. The dosage may either be increased in the event the subject does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

Certain factors may influence the dosage required to effectively treat a subject, including but not limited to the severity of the disease or condition, previous treatments, the general health and/or age of the subject, and other diseases present. It will also be appreciated that the effective dosage may increase or decrease over the course of a particular treatment.

Optimum dosages may vary depending on the relative potency of individual compounds, and can generally be estimated based on EC50s found to be effective in in vitro and in vivo animal models. In one embodiment, the administration of a composition is parenteral, e.g. intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral, ocular, intraneuronal, intrathecal, or intracerebral. Administration can be provided by the subject or by another person, e.g., a health care provider.

Kits

In certain aspects of the disclosure, kits are provided, comprising one or more containers housing a composition, complex, oligonucleotide and/or nucleic acid (e.g., synthetic mRNA) as described herein. In some embodiments, the composition is a pharmaceutical composition comprising an oligonucleotide and/or a nucleic acid (e.g., synthetic mRNA) as described herein and a pharmaceutically acceptable carrier. In some embodiments, the individual components of the pharmaceutical composition may be provided in one container. Alternatively, it may be desirable to provide the components of the pharmaceutical composition separately in two or more containers, e.g., one container for oligonucleotides, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

Chemical Definitions

Definitions of specific functional groups and chemical terms are described in more detail below.

Moieties described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, NY, 1962); and Wilen, S. H., *Tables of Resolving Agents and Optical Resolutions*, p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers. Unless otherwise stated, structures depicted herein are also meant to include compounds that differ only in the presence of one or more isotopically enriched atoms.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F).

The term "haloalkyl" is a substituted alkyl group, wherein one or more of the hydrogen atoms are independently replaced by a halogen, e.g., fluoro, bromo, chloro, or iodo. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain.

The term "alkenyl" refers to a radical of a straight-chain or branched hydrocarbon group having from 2 to 10 carbon atoms and one or more carbon-carbon double bonds (e.g., 1, 2, 3, or 4 double bonds). Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl").

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system.

In some embodiments, "carbocyclyl" is a monocyclic, saturated carbocyclyl group having from 3 to 14 ring carbon atoms ("$C_{3-14}$ cycloalkyl").

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl").

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl").

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl").

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted.

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group. An "amine" group can be an amino or substituted amino group.

The term "sulfinyl" refers to the group —S(=O)$R^{aa}$, wherein $R^{aa}$ is as defined herein.

The term "acyl" refers to a group having the general formula —C(=O)$R^{X1}$, —C(=O)O$R^{X1}$, —C(=O)—O—C(=O)$R^{X1}$, —C(=O)S$R^{X1}$, —C(=O)N($R^{X1}$)$_2$, —C(=S)$R^{X1}$, —C(=S)N($R^{X1}$)$_2$, and —C(=S)S($R^{X1}$), —C(=N$R^{X1}$)$R^{X1}$, —C(=N$R^{X1}$)O$R^{X1}$, —C(=N$R^{X1}$)S$R^{X1}$, and —C(=N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas.

The term "carbonyl" refers a group wherein the carbon directly attached to the parent molecule is sp$^2$ hybridized, and is substituted with an oxygen, nitrogen or sulfur atom.

Nitrogen atoms can be substituted or unsubstituted as valency permits, and include primary, secondary, tertiary, and quaternary nitrogen atoms.

Whereas the compounds and compositions described herein are represented with formulae depicting a formal negative charge, it is understood that said compounds and compositions further comprises a suitable cationic counterion such that the net charge of compound or composition is zero. Suitable cationic counterions are known in the art and include, for example, hydronium (H$_3$O$^+$), sodium, potassium, calcium, magnesium, ammonium and the like.

In certain embodiments, the substituent present on the nitrogen atom is an nitrogen protecting group (also referred to herein as an "amino protecting group"). Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Nitrogen protecting groups include, but are not limited to, amide, carbamate, and sulfonamide groups. A nitrogen protecting group may be an acyl group, as defined herein. In certain embodiments, the substituent present on an oxygen atom is an oxygen protecting group (also referred to herein as an "hydroxyl protecting group"). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. A hydroxyl protecting group may be an acyl group, as defined herein. As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

The invention is not intended to be limited in any manner by the above exemplary listing of substituents.

The present invention is further illustrated by the following Examples, which in no way should be construed as further limiting.

EXAMPLES

Example 1: Synthesis of N-Acetylgalactosamine (GalNAc)-Conjugated Oligonucleotides Synthesis of Trivalent GalNAc-Conjugated RaNA-Oligonucleotides

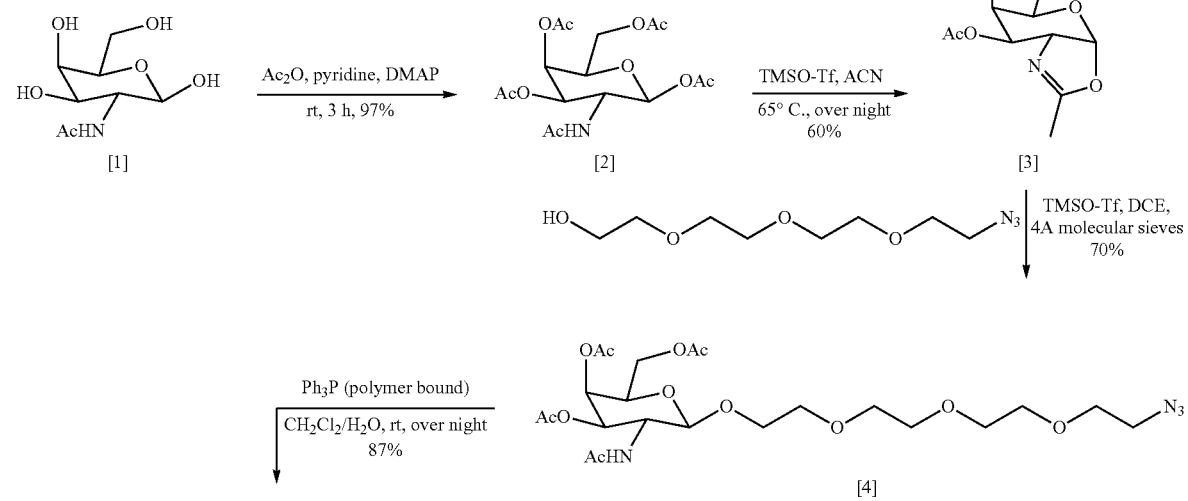

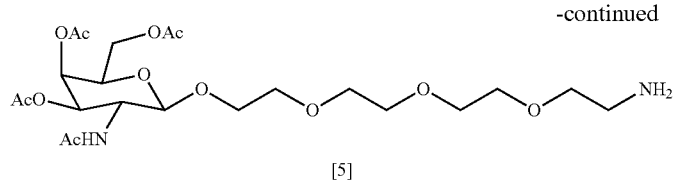

[5]

Synthesis of Acetylated GalNAc [2]

See, e.g., Guo, et. al. *Bioconjug. Chem.* 2006, 17, 1537-1544. GalNAc (10 g, 45.2 mmol) was dissolved in pyridine (100 mL). DMAP (1.4 g, 11.3 mmol) was added in it. Acetic anhydride (46.2 mL, 452 mmol) was added into the reaction mixture and stirred for next three hours. Reaction was completed within three hours based on TLC. After completion of reaction the crude mixture was evaporated off to dryness and purified via column chromatography (0-100% Ethyl acetate in Pet ether). The product comes at 100% Ethyl acetate. Pure product (17 g, 97%) was isolated as white foam and characterized based on Mass analysis. Results: ESI-MS analysis: Calculated $C_{16}H_{23}NO_{10}$. $Na^+$, $[M+Na^+]$=412.13, Observed=412.12.

Synthesis of Oxazoline [3]

See, e.g., Guo, et. al. *Bioconjug. Chem.* 2006, 17, 1537-1544; Manoharan, et.al. *J. Am. Chem. Soc.* 2014, 136, 16958-16961. Compound 2 (17 g, 43.7 mmol) was dissolved in anhydrous acetonitrile (100 mL). 4 Å molecular sieves were added in to the reaction mixture to keep it under complete anhydrous condition. Reaction mixture was cooled to zero degree and TMSOTf (11.84 mL, 65.5 mmol) was added in it. Reaction was then slowly warmed up to room temperature and then heated to 65° C. over night. After completion of reaction, triethylamine (~17 mL) was added to quench the reaction. Molecular sieves were filtered off and the reaction mixture was evaporated off to dryness. It was then diluted with ethyl acetate (~250 mL). Organic layer was washed with sodium bicarbonate (3×100 mL) and with brine solution (2×100 mL). Organic layer was dried over anhydrous sodium sulfate and evaporated off to obtain a crude product (12.6 g) as brown color foam. MS analysis confirmed the formation of desired oxazoline derivative 3. The crude mixture was taken into the next step without further purification. Results: ESI-MS analysis: Calculated $C_{14}H_{19}NO_8$, $[M+H^+]$=329.10, Observed=329.0.

Synthesis of [4]

See, e.g., Guo, et. al. *Bioconjug. Chem.* 2006, 17, 1537-1544; Manoharan, et.al. *J. Am. Chem. Soc.* 2014, 136, 16958-16961. Compound 3 (9.0 g, 27.3 mol) was co-evaporated with 1,2-dichloroethane (3×50 mL) and then re-dissolved in to the same solvent (250 mL). Reaction mixture was then stirred with 4 Å molecular sieves (2 g) for 5 min at room temperature. Azido-dPEG$_4$-OH (6.59 g, 30.1 mmol) was added and stirring was continued for 30 min. TMS-triflate (2.5 mL, 13.7 mmol) was added drop-wise under constant stirring over 10 min. Stirring was continued over night at 45° C. followed by quenching with saturated NaHCO$_3$ solution (100 mL). The organic layer was separated, diluted with dichloromethane 200 mL, and washed with water (2×100 mL) and brine (2×100 mL) solution. Finally, the organic layer was dried over anhydrous Na$_2$SO$_4$, and evaporated to dryness under reduced pressure. The crude product was purified via column chromatography (1-2% methanol in dichloromethane). Pure product 4 (10.5 g, 70%) was isolated as light yellow oil and characterized based on Mass and $^1$HNMR analysis. Results: ESI-MS analysis: Calculated $C_{22}H_{36}N_4O_{12}$. $Na^+$, $[M+Na^+]$=571.22, Observed=571.20.

Synthesis of [5]

To a stirred solution of compound 4 (2.3 g, 41.9 mmol) in dichloromethane (50 mL), polymer bound triphenylphosphine (6.60 g, 83.9 mmol, loading 3 mmol/g) was added at room temperature and stirred for 2 h. Water (2.3 mL, 126 mmol) was added into the reaction mixture and continued for another 3 h at room temperature. After completion of reaction the crude mixture was filtered off and evaporated to complete dryness under high vacuum to obtain compound 5 (1.9 g, 87%) as a pale yellow sticky solid. Compound 5 was taken to the next step almost immediately without further purification. Compound 5 was characterized based on mass analysis. Results: ESI-MS analysis: Calculated $C_{22}H_{39}N_2O_{12}$, $[M+H^+]$=523.25, Observed=523.20.

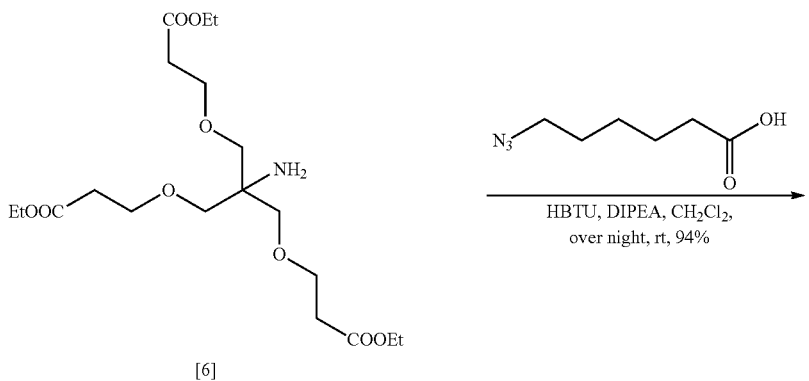

[6]

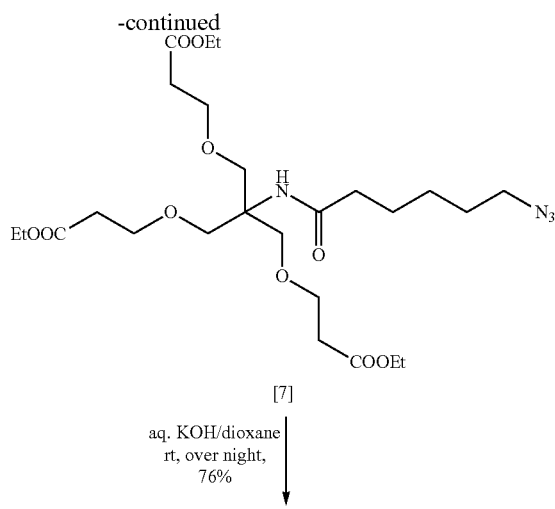

[7]

aq. KOH/dioxane
rt, over night,
76%

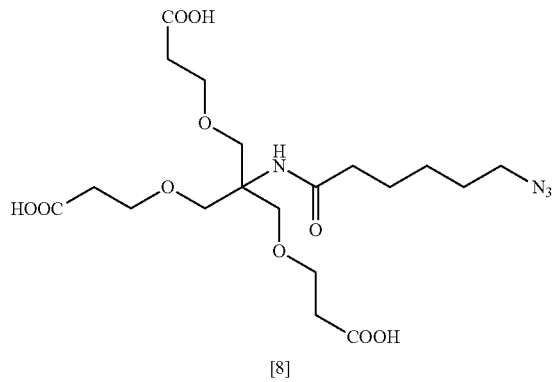

[8]

Synthesis of [7]

See, e.g., Biessen, et. al. *J. Med. Chem.* 1999, 42, 609-618. HBTU (7.95 g, 7.0 mmol) was added to a mixture of azido hexanoicacid (3.0 g, 19.1 mmol) and compound 6 (8.82 g, 7.0 mmol) in anhydrous dichloromethane (150 mL) under argon atmosphere at room temperature. DIPEA (13.2 mL, 25.5 mmol) was added in to the reaction mixture slowly and dropwise. Reaction was completed within six hours based on TLC. After the completion of reaction, crude mixture was evaporated off and diluted with ethylacetate (200 mL). Organic layer was washed with water (2×50 mL), brine solution (2×50 mL) and then dried over anhydrous sodium sulphate. Organic layer was further evaporated to dryness and purified via column chromatography (0-100% Ethyl acetate in Pet ether). The product comes at 30-50% ethyl acetate. Pure product 7 (10 g, 94%) was isolated as a colorless liquid and characterized based on NMR and Mass analysis. Results: ESI-MS analysis: Calculated $C_{25}H_{44}N_4O_{10}$. $Na^+$, $[M+Na^+]$=583.30, Observed=583.30.

Synthesis of [8]

See, e.g., Biessen, et. al. *J. Med. Chem.* 1999, 42, 609-618. Compound 7 (3.4 g, 6.07 mmol) was dissolved in a mixture (3:1) of dioxane (150 mL) and water (50 mL) at room temperature. Aqueous sodium hydroxide (4M, 12 mL) was added into the reaction mixture and continued overnight at same temperature. Reaction mixture was neutralized and acidified further with excess acetic acid and extracted with ethyl acetate (5×100 mL). Combined organic layer was dried over sodium sulfate and evaporated to dryness to obtain compound 8 (2.2 g, 76%) as a colorless oil. Formation of compound 8 was confirmed based on MS analysis. Results: ESI-MS analysis: Calculated $C_{19}H_{31}N_4O_{10}$, [M−H]=475.20, Observed=475.10

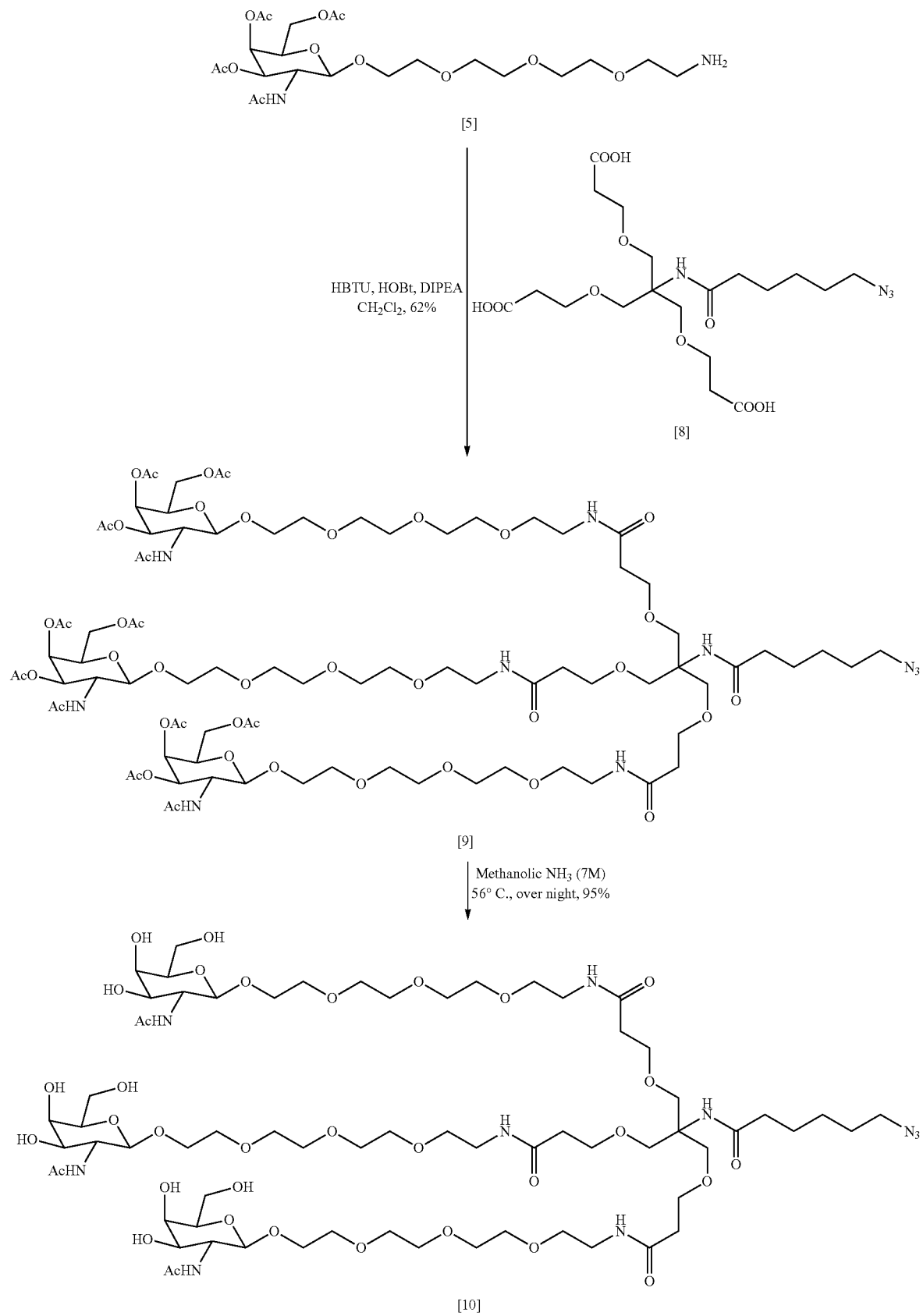

Synthesis of [9]

See, e.g., Manoharan, et.al. *J. Am. Chem. Soc.* 2014, 136, 16958-16961. To a solution of compound 8 (0.5 g, 1.05 mmol) and 5 (2.74 g, 5.25 mmol) in DMF (30 mL) were added HOBt (0.57 g, 4.20 mmol) and HBTU (1.99 g, 5.25 mmol) followed by slow addition of DIEA (1.83 mL, 10.5 mmol). The reaction was stirred overnight at room temperature and diluted with water. The mixture was extracted with ethyl acetate (2×100 mL). The water phase was separated, extracted with DCM (4×100 mL); and the combined organic layers were washed consecutively with saturated $NaHCO_3$ (2×50 mL), water (2×50 mL), and brine (50 mL). After drying over anhydrous $Na_2SO_4$, the solvent was evaporated under reduced pressure, and the residue was purified by silica gel chromatography (eluent: 10-15% MeOH in DCM) to obtain the compound 9 as a pale yellow foam (1.3 g, 62%). Isolation of pure trivalent GalNAc compound 9 was confirmed based on MS and NMR analysis. Results: ESI-MS analysis: Calculated $C_{85}H_{140}N_{10}O_{43} \cdot Na^+$, $[M+Na^+]$=2011.89, Observed=2011.60.

Synthesis of [10]

Compound 9 (1.3 g, 0.65 mmol) was dissolved in methanolic ammonia (7M, 50 mL) in a sealed vial and left over night inside the oven at 56° C. Reaction mixture was then evaporated to dryness and washed with ether (3×10 mL) and left on a high vacuum pump to obtain pale yellow sticky solid compound 10 (1.1 g, 95%). Formation of pure compound 10 was confirmed based on mass and NMR analysis. Results: ESI-MS analysis: Calculated $C_{67}H_{122}N_{10}O_{34}Na^+$, $[M+Na^+]$=1633.80, Observed=1633.60. $^1$H NMR (DMSO-$d_6$): δ 7.91-7.94 (m, 2H), 7.59-7.61 (m, 2H), 7.27 (s, 3H), 6.67 (s, 3H), 4.49-4.60 (m, 7H), 4.26-4.28 (m, 2H), 3.16-3.79 (m, 65H), 2.27-2.30 (m, 3H), 2.06-2.08 (m, 2H), 1.74-1.79 (m, 14H), 1.44-1.52 (m, 2H), 1.22-1.29 (m, 2H).

Synthesis of Trivalent GalNAc Conjugated Oligonucleotides (at the 5'-End of a Fully Phosphothioated Oligonucleotides)

General Protocol

Figure 12:
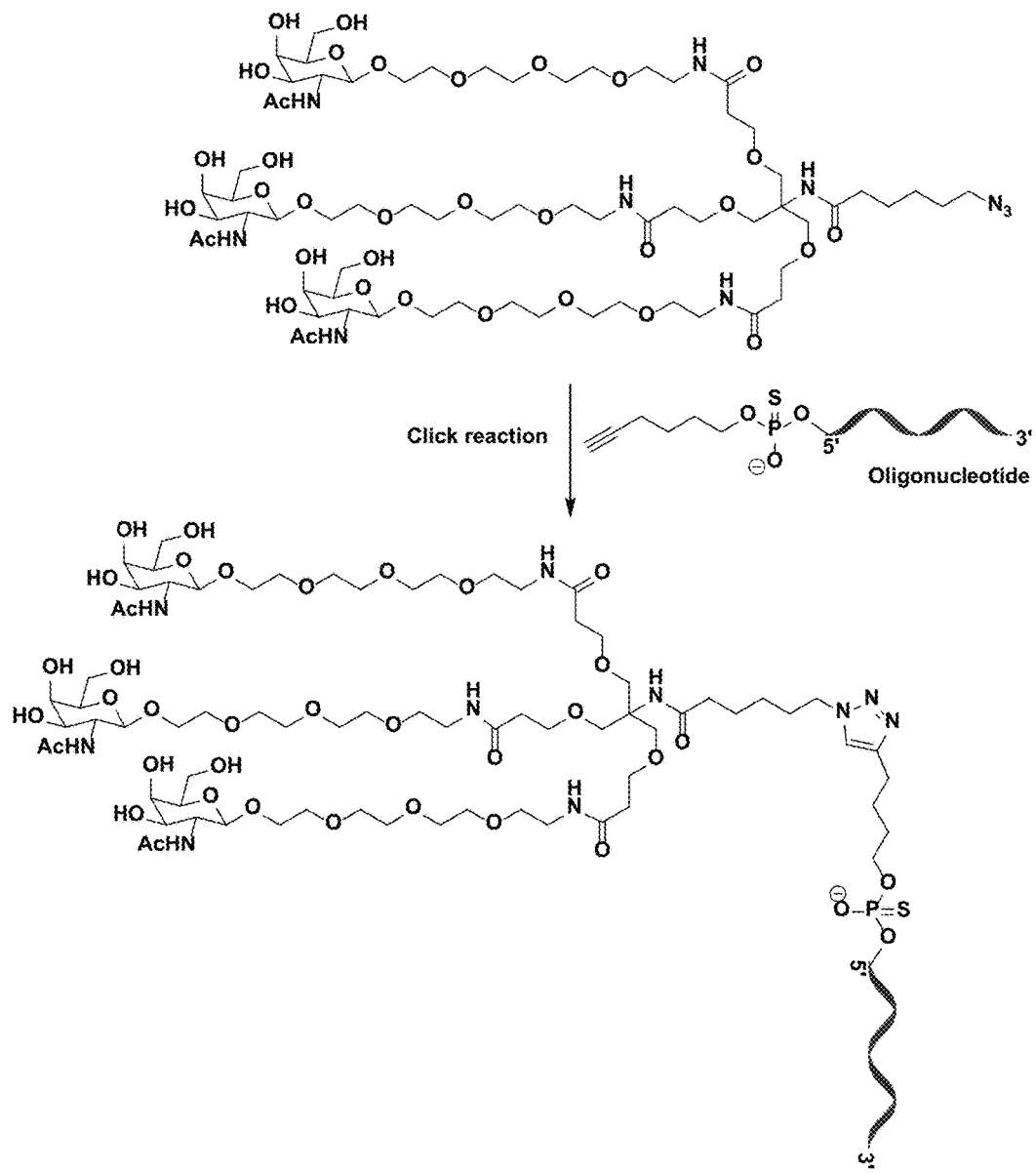

For a general scheme, see FIG. 12.

5'-alkyne modified fully phosphothioated oligo nucleotides were synthesized using AKTA oligopilot 100 on a 245 μM scale following standard solid phase oligo synthesis protocol. 5-hexyl-1-yl-cyanoethyl amidite was purchased from Glen Research Corporation, USA and was incorporated on to the 5'-end of the oligonucleotides. Oligonucleotides were cleaved from the solid support using 30% aq. ammonium hydroxide (45 mL) at 56° C. overnight inside the oven. Crude oligonucleotide was purified via Hi Prep Q HP 16/10 column [with a solvent gradient 10-100% of eluent B, where, eluent A: 10 mM aq. NaOH and eluent B: aq. NaCl (2.5 M)+NaOH (10 mM)] and then desalted (via Sephadex G25) on an AKTA pure system. Finally, the mass and purity of purified oligonucleotides were identified using Agilent 6130 Quadrupole LC/MS system. 5'-alkyne functionalized oligos were reacted with Trivalent GalNAc azides (GalNAc$_3$—N$_3$; e.g., compound 10) following click reaction conditions. See, e.g., Manoharan, et.al. *Org. let.* 2010, 12, 5410-5413; Manoharan, et.al. *ACS Chem. Biol.* 2015, 10, 1181-1187. Finally, trivalent GalNAc-conjugated oligos were purified, desalted using AKTA pure system and characterized by LCMS analysis.

Figure 10A:
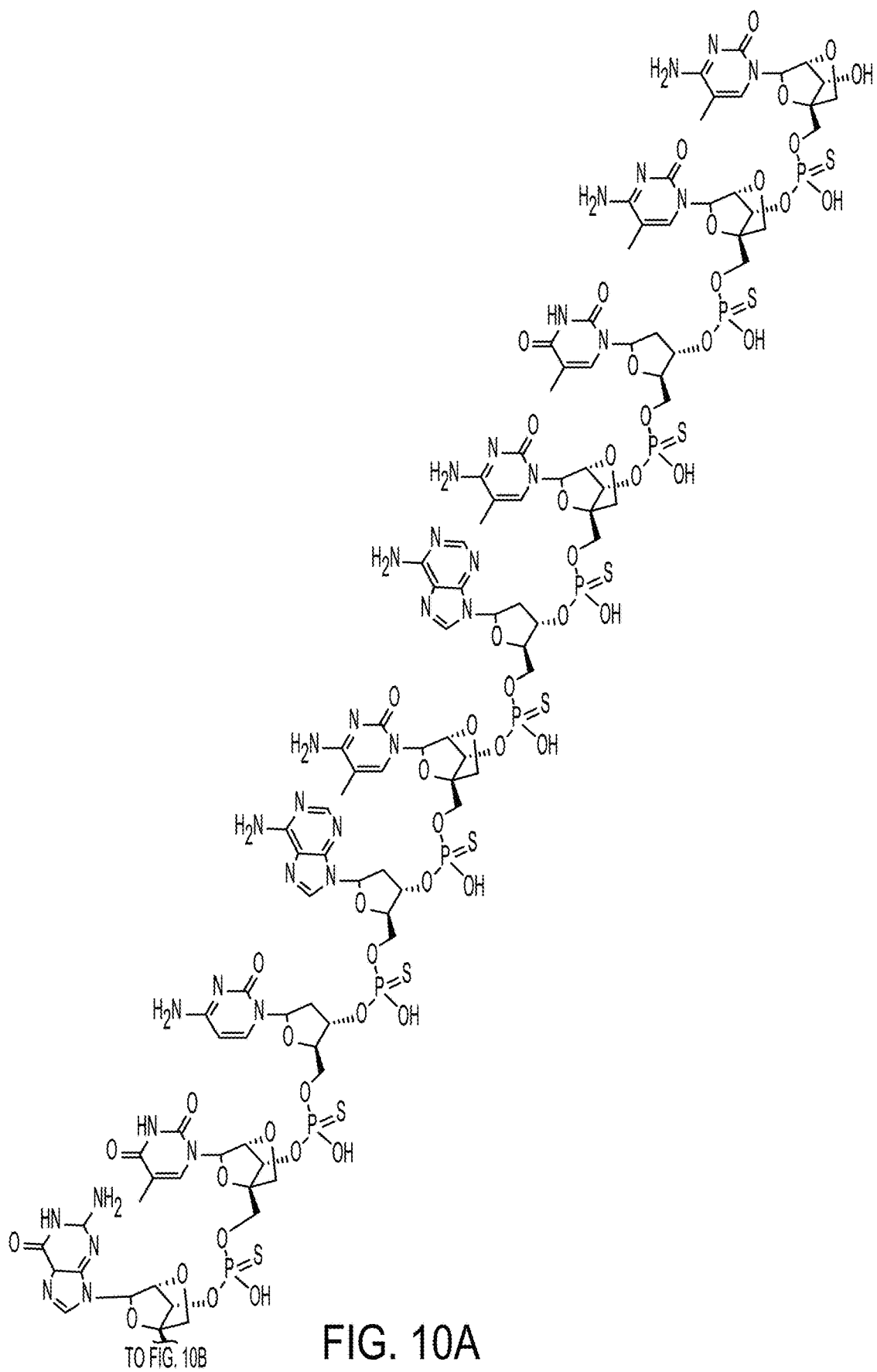
FIGS. 10A-10C show the structure of an exemplary GalNac-conjugated oligonucleotide containing the nucleotide sequence CCATTGTCACACTCC (SEQ ID NO: 1), which is designed to be complementary to a synthetic binding site to include in the synthetic mRNA 3' UTR.
Figure 10B:
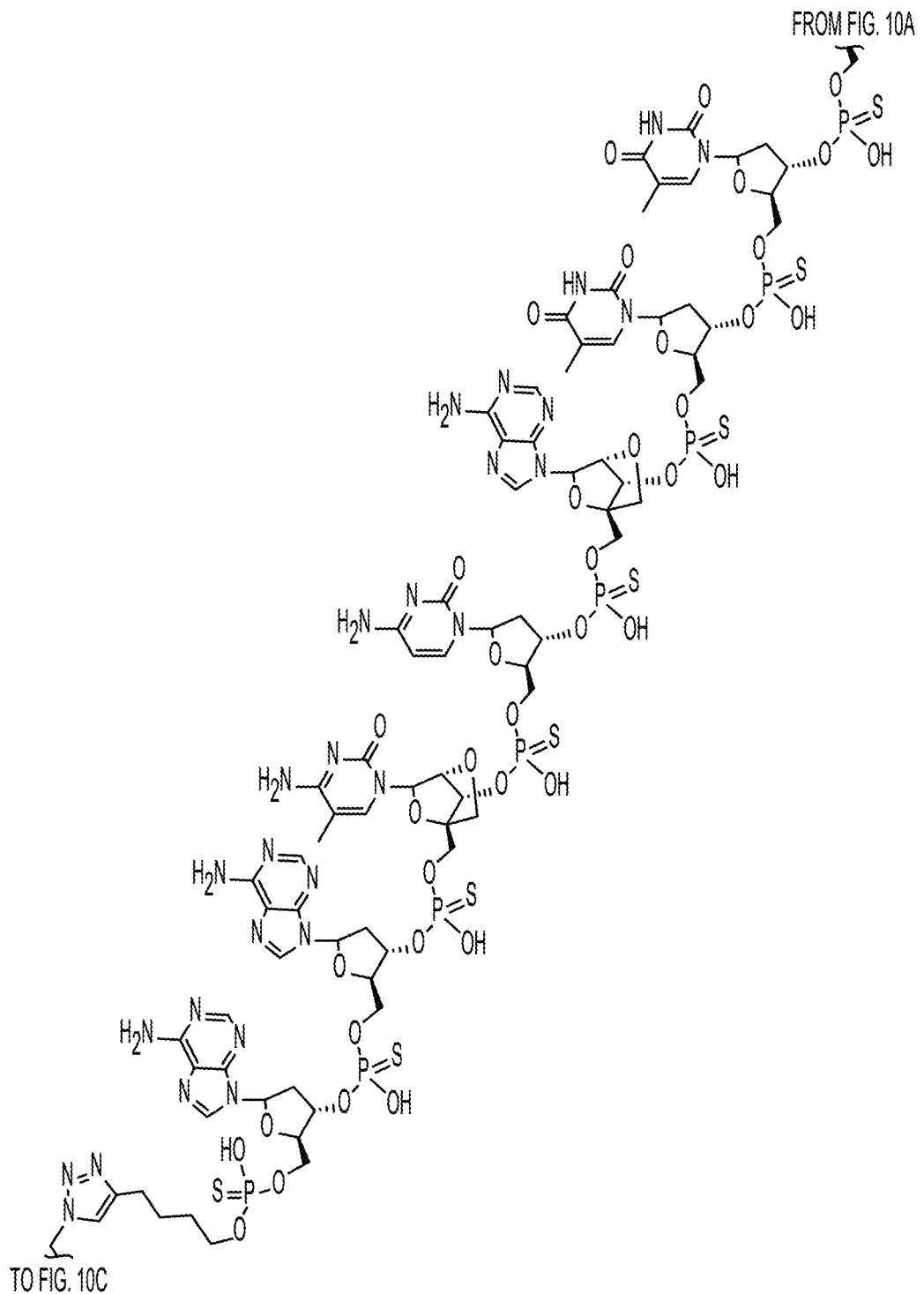
Figure 10C:
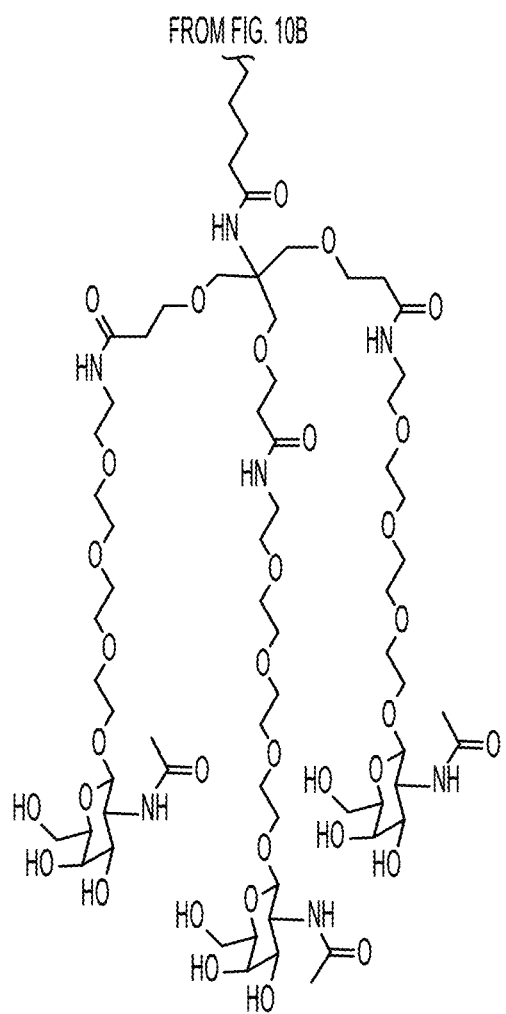

Example 2: GalNAc Conjugation Increases Uptake of Oligonucleotides in the Liver and Decreases Kidney Excretion Methods Oligonucleotide Design A single-stranded anti-miR122 oligonucleotide was designed to bind to and sterically inhibit miR122, a microRNA expressed in the liver that is involved in regulation of genes such as CD320 and AldoA and in the regulation of cholesterol levels. The sequence of the oligonucleotide was CCATTGTCACACTCC (SEQ ID NO: 1) with the following modification pattern: lnamCs;dCs;lnaAs; dTs;dTs;lnaGs;lnaTs;dCs;dAs;lnamCs;dAs;lnamCs;dTs; lnamCs;lnamC. The key for the modifications are shown in Table 1 below. The oligonucleotide was then conjugated to a trivalent GalNAc moiety as described in Example 1. The structure of the oligonucleotide conjugated to the GalNAc moiety is shown in FIGS. 10A-10C and a zoomed-in view of the GalNAc moiety attached to an oligonucleotide is shown in FIG. 12. An unconjugated version of the same oligonucleotide was used as a control in the below experiments.

TABLE 1

A listing of nucleotides and nucleotide modifications

| Symbol | Feature Description |
|---|---|
| dAs | adenosine DNA w/3' phosphorothioate |
| dCs | cytosine DNA w/3' phosphorothioate |
| dGs | guanosine DNA w/3' phosphorothioate |
| dTs | thymidine DNA w/3' phosphorothioate |
| lnaAs | adenosine LNA w/3' phosphorothioate |
| lnamCs | 5-methyl cytosine LNA w/3' phosphorothioate |
| lnaGs | guanosine LNA w/3' phosphorothioate |
| lnaTs | thymidine LNA w/3' phosphorothioate |
| lnaA | adenosine LNA |
| lnamC | 5-methyl cytosine LNA |
| lnaG | guanosine LNA |
| lnaT | thymidine LNA |
| omeAs | 2'-O-methyl adenosine nucleotide w/3' phosphorothioate |
| omeCs | 2'-O-methyl cytosine nucleotide w/3' phosphorothioate |
| omeGs | 2'-O-methyl guanosine nucleotide w/3' phosphorothioate |
| omeUs | 2'-O-methyl thymidine nucleotide w/3' phosphorothioate |
| omeA | 2'-O-methyl adenosine nucleotide |
| omeC | 2'-O-methyl cytosine nucleotide |
| omeG | 2'-O-methyl guanosine nucleotide |
| omeU | 2'-O-methyl uracil nucleotide |

In Vivo Delivery of Oligonucleotides 0.3 mg/kg, 1 mg/kg, 3 mg/kg, or 10 mg/kg of GalNAc-conjugated anti-miR122 oligonucleotide or unconjugated anti-miR122 oligonucleotide or an equivalent control volume of PBS was delivered subcutaneously to 8 week old male C57BL6 mice. The mice were then euthanized at day 6 after administration and both liver and kidney tissue was harvested from each animal.

Tissue Concentration

Mouse liver and kidney blank tissues were weighed, homogenized and digested by proteinase K, RNase and DNase at a tissue to nuclease buffer ratio of one to four. This digested matrix blank was used to build a calibration standard. Tissue study samples were digested the same way as the blank matrix, then extracted by phenol, chloroform and dried down and then re-extracted by solid phase extraction (SPE). Ions at m/z of 2459.4696, 1654.4873 and 1684.4877 were monitored for the GalNAc-conjugated anti-miR122 oligonucleotide, the unconjugated anti-miR122 oligonucleotide, and a control oligonucleotide analogue respectively on Agilent TOF 6230 mass-spectrometer. A reverse phase chromatographic condition was developed on a Thermo DNAPac RP column and the eluates from the SPE were analyzed by LC/MS instrumentation. The calibration standard curve ranged from 0.5 to 50.0 ug/g (0.1 to 10 ug/mL in homogenized matrix) in both matrices and a linear regression curve fitting model was used. The oligonucleotide analogue was utilized as internal standard for quantitation of the two oligonucleotides.

Expression Analysis

Levels of AldoA and CD320 mRNA were measured in liver tissue using qPCR. Briefly, a small piece (<100 mg) of liver from the left medial lobe of each animal was individually transferred into 0.7 mL Qiazol lysis reagent (Qiagen) for ALDOA and CD320 gene expression analysis. RNA was extracted from liver samples by a miReasy 96-kit (Qiagen) according to the manufacturer's instructions. RNA (400 ng total) was reverse transcribed using a high-capacity cDNA reverse transcription kit (Cat. 4368813, Life Technologies Inc.) according to the manufacturer's instructions at a total volume of 20 μL. cDNA was diluted 1 to 4 with water, and 2 μL were used for qPCR (in duplicate) with the TaqMan Universal Master Mix II, no UNG (Cat. 4440040, Life Technologies) using the Viia7 system (Life Technologies). Primer/probe sets specific for ALDOA and CD320 (Integrated DNA Technologies) were used in the qPCR. Gene expression analysis was performed as follows: The Ct (Cycle threshold) value output was translated to fold change using a standard delta-delta Ct method; that is, values were normalized to the house-keeping gene, GAPDH, and baseline (fold change=1) was set to expression from saline-treated animals using the mean of all saline-treated animals.

For total cholesterol measurements, serum was obtained by centrifuging whole blood samples collected in BD Microtainer Serum Separator tubes (Ref #365978, Becton, Dickinson and Company) for 10 minutes at 2000×g. The serum was then analyzed on a Vet Axcel Clinical Chemistry Analyzer (Alfa Wasserman Diagnostic Technologies LLC.) using Cholesterol kit (#SA1010).

Results

Figure 1B:
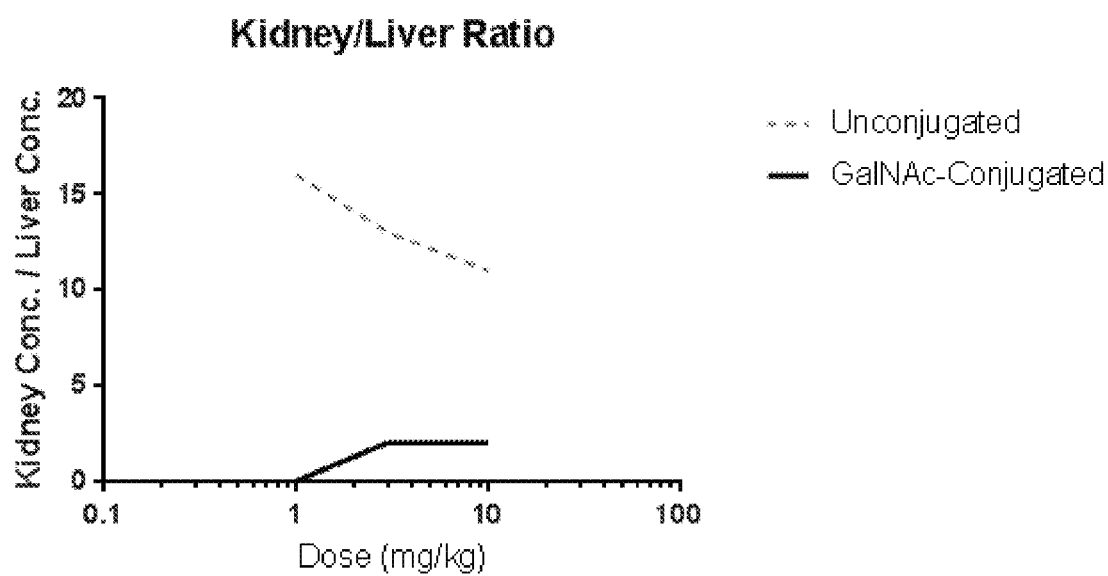
FIG. 1B is a graph showing the ratio of the kidney to liver concentration over different doses of an either unconjugated or conjugated to a GalNAc moiety.
Figure 2A:
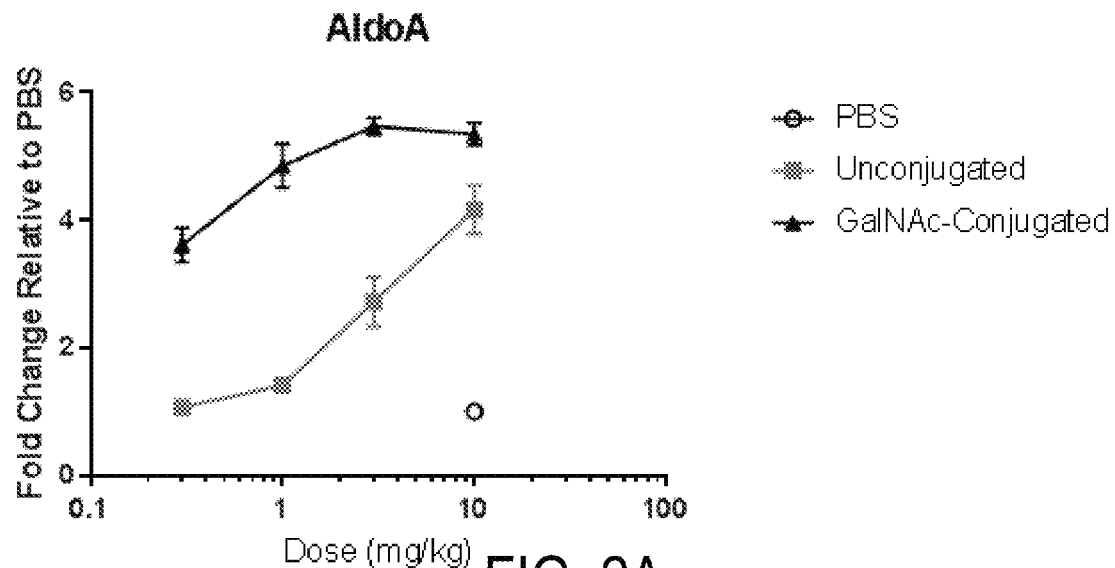
FIG. 2A is a graph showing the levels of AldoA mRNA in liver tissue from animals treated with an oligonucleotide either unconjugated or conjugated to a GalNAc moiety or with phosphate-buffered saline (PBS). Each data point represents data taken from four mice.
Figure 2B:
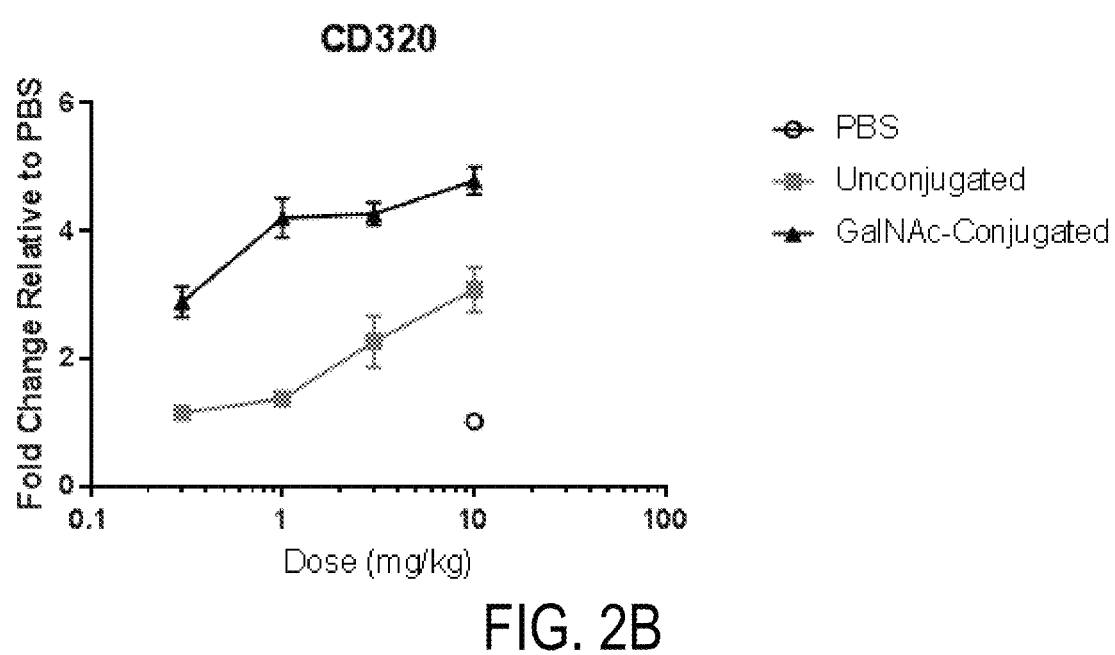
FIG. 2B is a graph showing the levels of CD320 mRNA in liver tissue from animals treated with an oligonucleotide either unconjugated or conjugated to a GalNAc moiety or with phosphate-buffered saline (PBS). Each data point represents data taken from four mice.
Figure 2C:
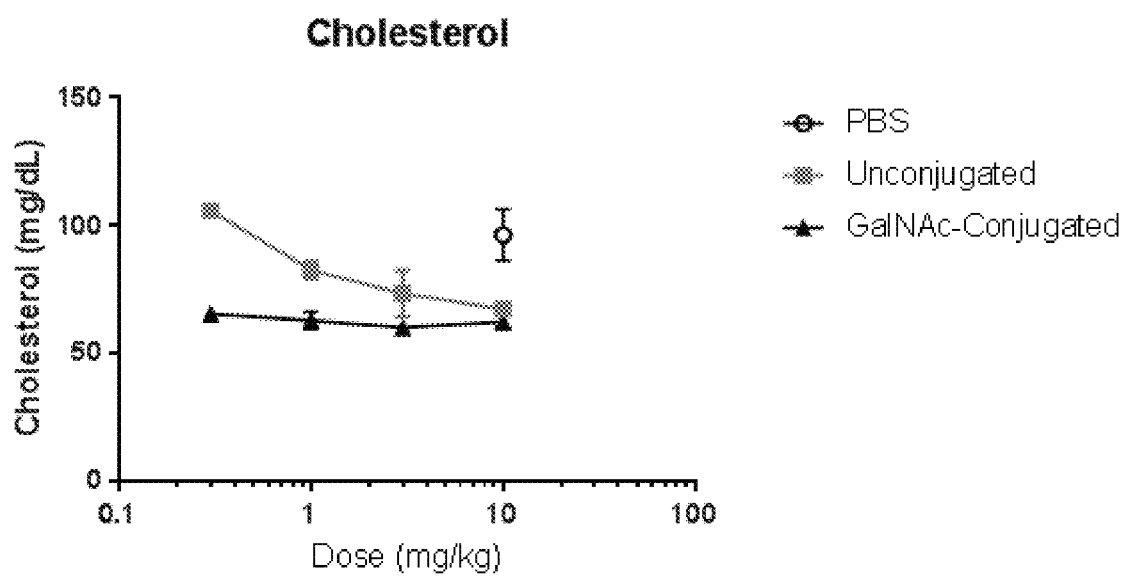
FIG. 2C is a graph showing the levels of cholesterol in animals treated with an oligonucleotide either unconjugated or conjugated to a GalNAc moiety or with phosphate-buffered saline (PBS). Each data point represents data taken from four mice.

A GalNAc-conjugated anti-miR122 oligonucleotide was assessed for the ability of the GalNAc moiety to increase uptake in liver in vivo as well as increase the in vivo activity of the oligonucleotide. Delivery in vivo of the GalNAc-conjugated version of the anti-miR122 oligonucleotide resulted in both increased liver uptake and decreased kidney excretion compared to the unconjugated version of the same oligonucleotide (FIGS. 1A and 1B). Additionally, levels of AldoA and CD320 mRNA, both of which are normally downregulated by miR122, increased more rapidly and to a greater extent with the GalNAc-conjugated oligonucleotide (FIGS. 2A and 2B). Levels of serum cholesterol, which decrease upon miR122 inhibition, were robustly lowered upon in vivo delivery of the GalNAc-conjugated version of the anti-miR122 oligonucleotide compared to the unconjugated version (FIG. 2C). In general, an about 10 to 30-fold enhancement in potency was observed with GalNAc-conjugation. These results demonstrate that GalNAc-conjugation increases liver uptake and activity of oligonucleotides.

Figure 3:
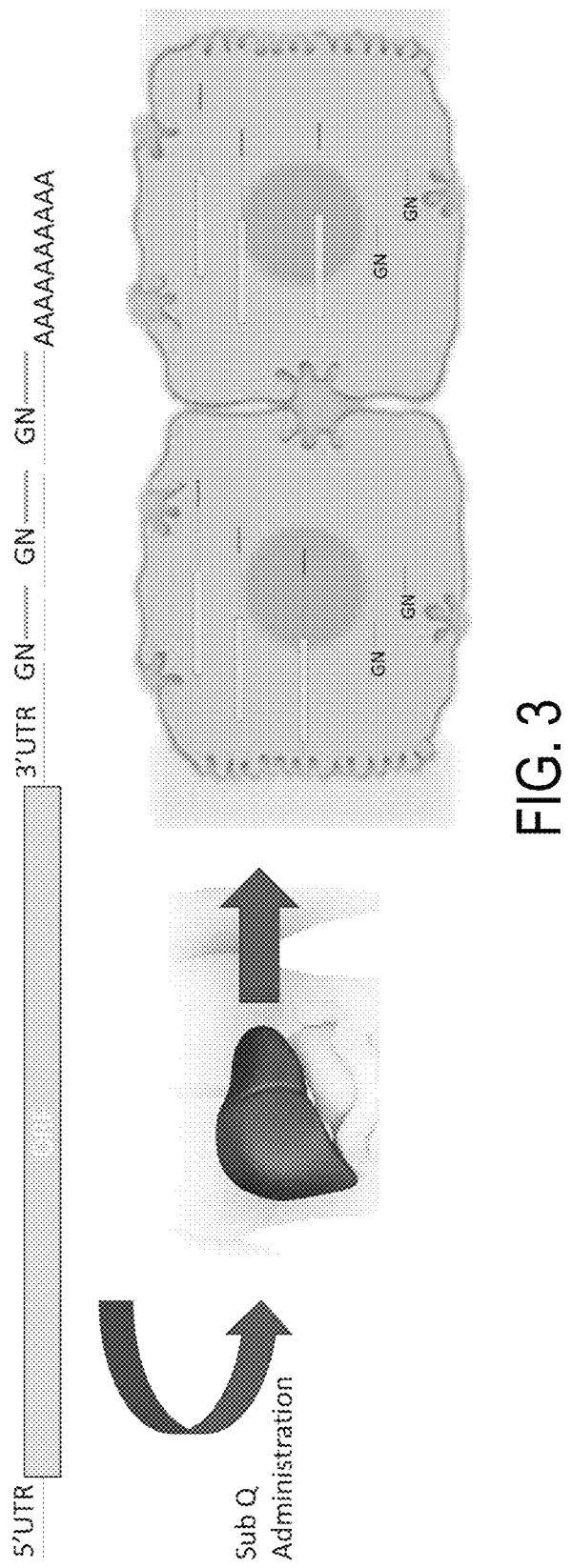
FIG. 3 is a schematic showing an exemplary synthetic mRNA with multiple GalNAc-conjugated oligonucleotides binding a modified 3'UTR that contains multiple binding sites for the oligonucleotides and delivery of the synthetic mRNA by subcutaneous administration with the goal being increased delivery of the synthetic mRNA to the liver.

Example 3: Use of GalNAc-Conjugated Oligonucleotides as Carrier Molecules for Synthetic mRNAs Without wishing to be bound by theory, it was hypothesized that GalNAc-conjugated oligonucleotides complementary to sequences on a modified or unmodified 3' UTR of a synthetic mRNA may act as carrier molecules for delivery of the synthetic mRNA to liver cells (FIG. 3). Upon uptake into hepatocytes, it was hypothesized that the payload synthetic mRNA would be released for translation (FIG. 3).

The OTC (ornithine transcarbamylase) mRNA was chosen as a model mRNA for testing because OTC activity in the liver is important for urea cycle function. Urea cycle disorders include OTC deficiency, which has an incidence of about 1 in 63,000 births in the United States and a mortality rate of about 11% (see, e.g., Summar et al. The incidence of urea cycle disorders. Mol. Genet. Metab. 2013). Loss of enzyme activity involved in the urea cycle, like OTC activity, results in build-up of ammonia, which can become highly toxic to the central nervous system, eventually leading to cerebral edema and neurological damage (see, e.g., Caldovic et al. Genotype-Phenotype Correlations in Ornithine Transcarbamylase Deficiency: A Mutation Update J. Genet. Genom. 2015).

The human ornithine transcarbamylase enzyme is expressed by the OTC gene in the liver and forms a homotrimer. There are at least 417 disease-causing mutations in the OTC gene that have been identified to date (see, e.g., Caldovic et al. Genotype-Phenotype Correlations in Ornithine Transcarbamylase Deficiency: A Mutation Update J. Genet. Genom. 2015). These disease-causing mutations include loss-of-function mutations, amino acid replacement mutations, and intronic mutations, which can result in a decrease or complete loss of OTC function in the liver and lead to OTC deficiency. OTC deficiency is an x-lined disease that occurs in two forms, a neonatal form, which affects approximately 30% of individuals and a delayed onset form which effects approximately 70% of individuals. The neonatal form is severe, occurs primarily in males, and has a ~24% mortality rate. The neonatal form is characterized by extremely low or a complete loss of OTC enzymatic activity. The current treatment for the neonatal form is liver transplantation, which if done before six months of age is typically curative. The delayed onset form is generally milder, with onset of hyperammonemia dependent on stress triggers. The delayed onset form is typically characterized by retention of at least some OTC enzymatic activity.

Figure 4:
FIG. 4 is a schematic of an exemplary strategy for generation of synthetic 3'UTR targeting oligonucleotide sequences and 3'UTRs containing binding sites for the identified oligonucleotides.

In order to address OTC deficiency, synthetic mRNA sequences containing coding sequences for human OTC are designed with binding sites within the 3'UTR for binding to GalNAc-conjugated oligonucleotides. Binding sites may be present within a naturally-occurring 3'UTR, such as the human OTC 3'UTR, or may be designed and included within a synthetic UTR sequence. For example, tiling may be used to identify binding sites present in the human OTC 3' UTR that are acceptable or optimal for oligonucleotide design (FIG. 4). In some instances, for example, oligonucleotides are designed to avoid microRNA seed sequences. As another example, a synthetic UTR sequence may be designed to include binding sites, including multiple copies of the same binding site, for GalNAc-conjugated oligonucleotides (FIG. 4). In some instances, for the synthetic UTR sequence, it may be advantageous to use binding sites that are not naturally present or are infrequently present in human mRNA 3' UTRs to avoid non-specific binding of the GalNAc-conjugated oligonucleotides to endogenous mRNAs. Use of a synthetic UTR sequence may also be advantageous, e.g., because it may be paired with other mRNAs and reduce the need to design new GalNAc-conjugated oligonucleotides for other mRNAs.

Figure 8A:
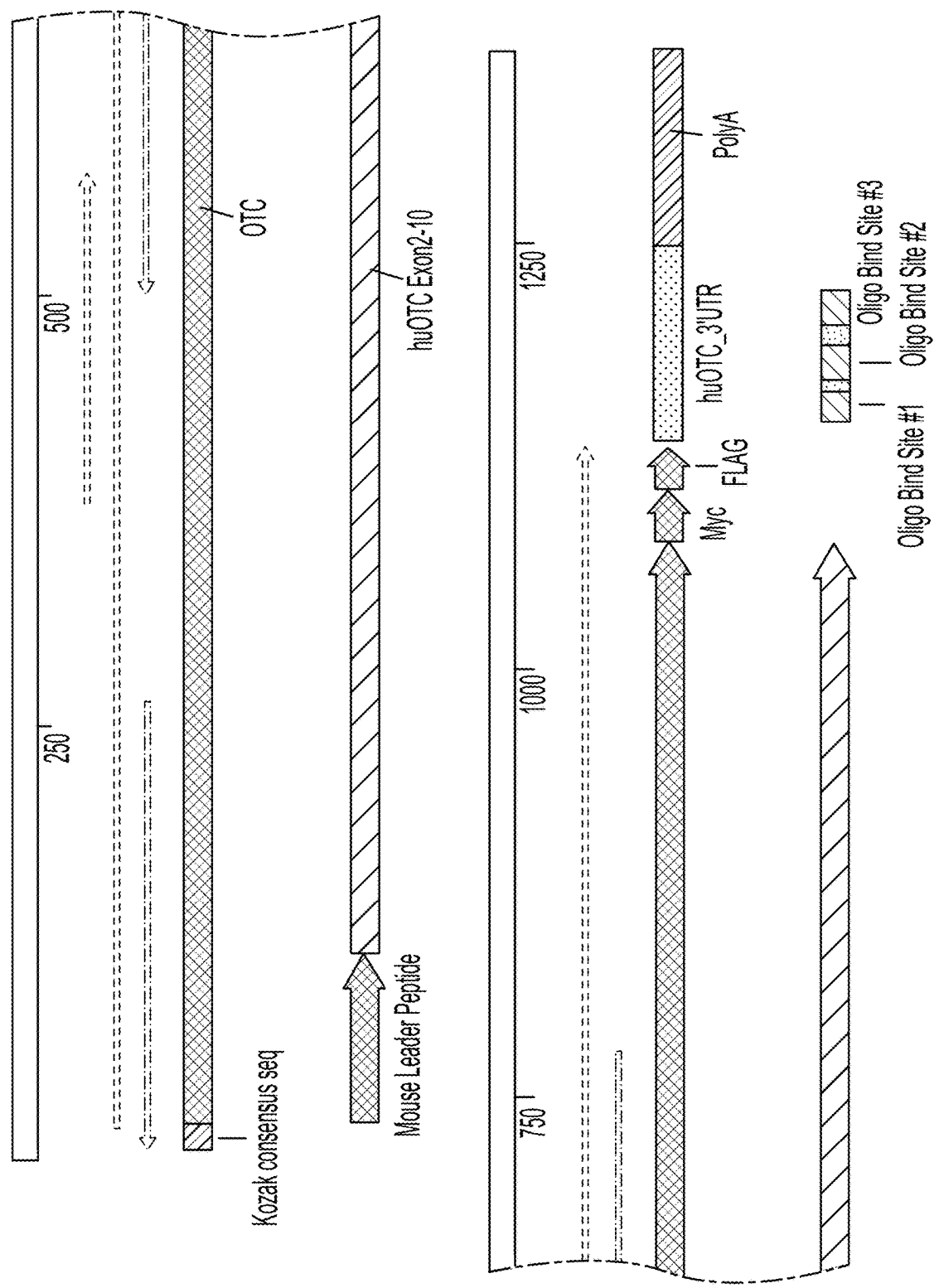
FIGS. 8A and 8B are a schematic of an exemplary synthetic mRNA containing either a human OTC ORF or containing an ORF with a mouse leader peptide and human OTC exons 2-10, either way followed by a human OTC 3'UTR. The sites for binding to a GalNAc-conjugated oligonucleotide are identified within the sequence of the human OTC 3'UTR by a 3' UTR end-targeting-oligo (ETO) screen. No synthetic sequences are added to the 3'UTR in this version of the synthetic mRNA.
Figure 8B:
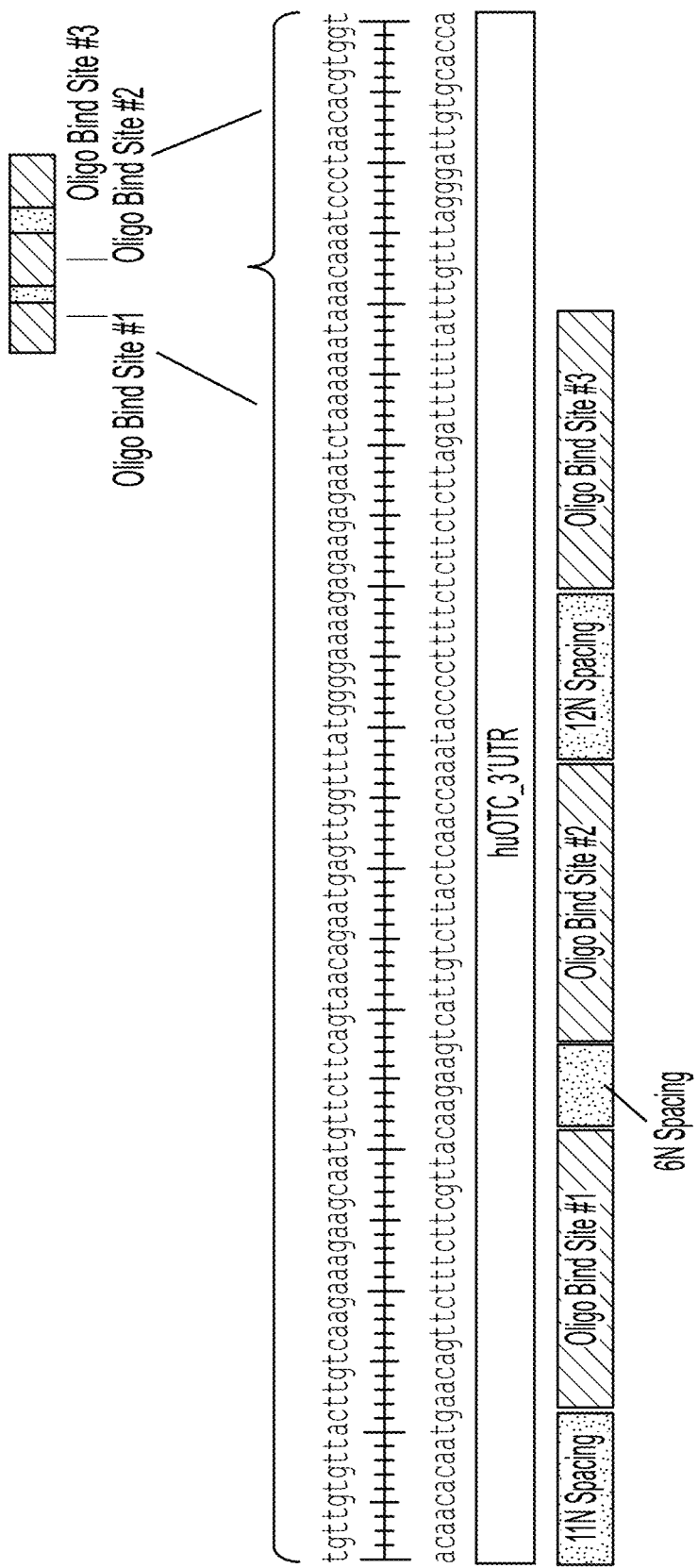
Figure 9A:
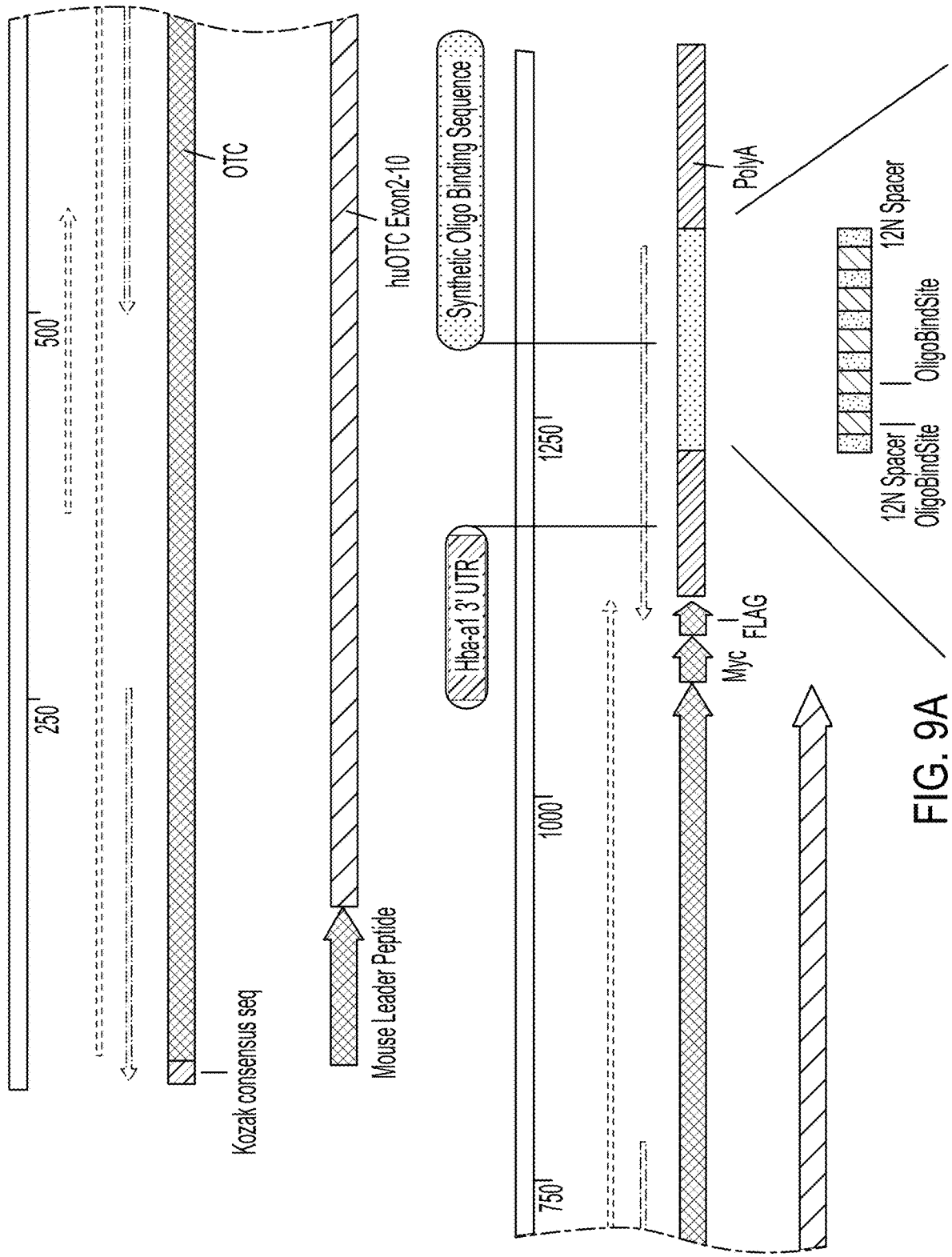
Figure 9C:
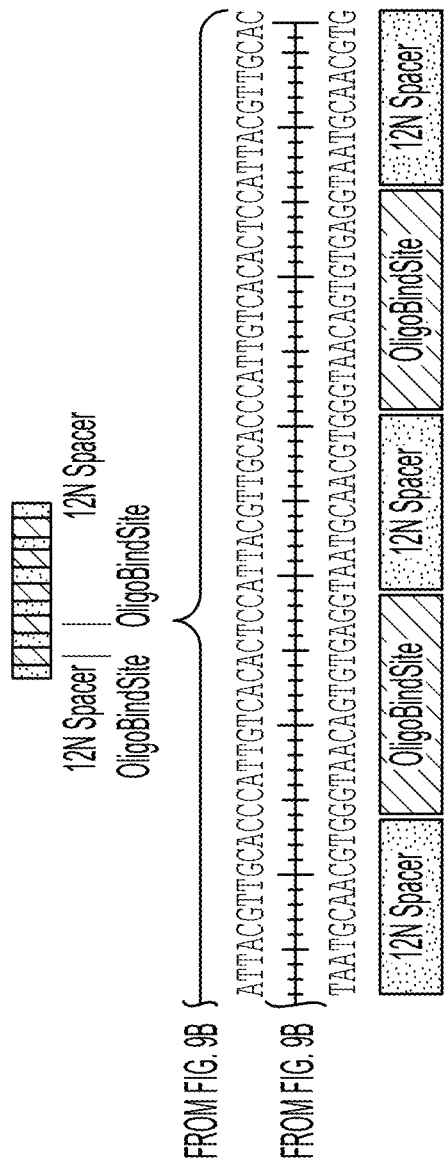

Example 4: Synthetic OTC mRNA Construct with Naturally-Occurring UTR Sequence for Binding to GalNAc-Conjugated Oligonucleotides A synthetic OTC mRNA sequence was designed to include a Kozak consensus sequence, a mouse leader peptide, human OTC exons 2 to 10 and the human OTC 3'UTR (FIGS. 8A and 8B). The sequence and features of the mRNA are shown below (any T in the below sequence may be replaced with a U). The mouse leader peptide sequence was included to enhance transport to mitochondria in mice for animal testing. The mouse leader peptide sequence may be replaced with a human sequence (e.g., human OTC exon 1) for use in human cells or subjects (FIGS. 8A and 8B).

| FEATURES | Location/Qualifier |
| --- | --- |
| 5'UTR | 1 . . . 14<br>/note="Kozak consensus seq" |
| mat_peptide | 15 . . . 1076<br>/note="OTC" |
| exon | 15 . . . 116<br>/note="Mouse Leader Peptide" |
| exon | 117 . . . 1076<br>/note="huOTC Exon2-10" |
| CDS | 1077 . . . 1106<br>/codon_start=1<br>/product="Myc (human c-Myc oncogene) epitope tag"<br>/note="Myc"<br>/translation="EQKLISEEDL" |
| CDS | 1107 . . . 1130<br>/codon_start=1<br>/product="FLAG(R) epitope tag, followed by an Enterokinase cleavage site<br>/note="FLAG"<br>/translation="DYKDDDDK" |
| misc_feature | 1134 . . . 1243<br>/note="huOTC_3'UTR" |
| misc_feature | 1145 . . . 1164<br>/note="Oligo Bind Site #1" |
| misc_feature | 1165 . . . 1170<br>/note="6N Spacing" |
| misc_feature | 1171 . . . 1190<br>/note="Oligo Bind Site #2" |
| misc_feature | 1191 . . . 1202<br>/note="12N Spacing" |
| misc_feature | 1203 . . . 1222<br>/note="Oligo Bind Site #3" |
| polyA_site | 1244 . . . 1363<br>/note="PolyA" |

(SEQ ID NO: 8)

```
  1 gccgccgcga tcgcatgctg agcaacctga ggatcctgct gaacaacgcc gccctgagga
 61 agggccacac cagcgtggtg aggcacttct ggtgcggcaa gcccgtgcag agccaggtgc
121 agctgaaggg ccgtgacctt ctcactctaa aaactttac cggagaagaa attaaatata
181 tgctatggct atcagcagat ctgaaattta ggataaaaca gaaggagag tatttgcctt
241 tattgcaagg gaagtcctta ggcatgattt ttgagaaaag aagtactcga acaagattgt
301 ctacagaaac aggctttgca cttctgggag gacatccttg ttttcttacc acacaagata
361 ttcatttggg tgtgaatgaa agtctcacgg acacggcccg tgtattgtct agcatggcag
421 atgcagtatt ggctcgagtg tataaacaat cagatttgga caccttgct aaagaagcat
481 ccatcccaat tatcaatggg ctgtcagatt tgtaccatcc tatccagatc ctggctgatt
541 acctcacgct ccaggaacac tatagctctc tgaaggtct taccctcagc tggatcgggg
601 atgggaacaa tatcctgcac tccatcatga tgagcgcagc gaaattcgga atgcacctc
```

-continued

```
 661 aggcagctac tccaaagggt tatgagccgg atgctagtgt aaccaagttg gcagagcagt
 721 atgccaaaga gaatggtacc aagctgttgc tgacaaatga tccattggaa gcagcgcatg
 781 gaggcaatgt attaattaca gacacttgga taagcatggg acaagaagag gagaagaaaa
 841 agcggctcca ggctttccaa ggttaccagg ttacaatgaa gactgctaaa gttgctgcct
 901 ctgactggac atttttacac tgcttgccca gaaagccaga agaagtggat gatgaagtct
 961 tttattctcc tcgatcacta gtgttcccag aggcagaaaa cagaaagtgg acaatcatgg
1021 ctgtcatggt gtccctgctg acagattact cacctcagct ccagaagcct aaatttgagc
1081 agaaactcat ctcagaagag gatctggatt acaaggatga cgacgataag taatgttgtg
1141 ttacttgtca agaaagaagc aatgttcttc agtaacagaa tgagttggtt tatggggaaa
1201 agagaagaga atctaaaaaa taaacaaatc cctaacacgt ggtaaaaaaa aaaaaaaaa
1261 aaaaaaaaaa aaaaaaaaaa aaaaaaaaaa aaaaaaaaaa aaaaaaaaaa aaaaaaaaaa
1321 aaaaaaaaaa aaaaaaaaaa aaaaaaaaaa aaaaaaaaaa aaa
```

Three oligonucleotide binding sites were chosen within the 3'UTR sequence and single-stranded oligonucleotide sequences were designed to bind to those sites. The sites were chosen based on an in silico analysis of the 3'UTR and the oligonucleotides were designed to avoid microRNA seed sequences present in the 3'UTR. Oligonucleotide sequences for binding to these sites are shown below and are conjugated to GalNAc. The key for abbreviations of the chemistry of each oligonucleotide are provided in Table 1.

Oligo Sequences for Targeting Binding Site #1:

| Name | Base sequence | Oligonucleotide chemistry pattern |
| --- | --- | --- |
| Oligo 41 | CATTGCTTCTTTCTTG ACAA (SEQ ID NO: 9) | omeCs;lnaAs;lnaTs;dTs;lnaGs;dCs;lnaTs;dTs;lnamCs; dTs;lnaTs;dTs;lnamCs;dTs;lnaTs;dGs;lnaAs;dCs;lnaAs; omeA |
| Oligo 42 | CATUGCTUCUTUCUT GACAA (SEQ ID NO: 10) | omeCs;lnaAs;lnaTs;omeUs;lnaGs;omeCs;lnaTs;omeUs; lnaCs;omeUs;lnaTs;omeUs;lnamCs;omeUs;lnaTs;omeGs; lnaAs;omeCs;lnaAs;omeA |

Oligo Sequences or Targeting Binding Site 3

| Name | Base sequence | Oligonucleotide chemistry pattern |
| --- | --- | --- |
| Oligo 43 | AACCAACTCATTCTGT TACU (SEQ ID NO: 11) | omeAs;lnaAs;lnamCs;dCs;lnaAs;dAs;lnaCs;dTs;lnaCs; dAs;lnaTs;dTs;lnaCs;dTs;lnaGs;dTs;lnaTs;dAs;lnamCs; omeU |
| Oligo 44 | AACCAACUCAUUCUG UTACU (SEQ ID NO: 12) | omeAs;lnaAs;lnamCs;omeCs;lnaAs;omeAs;lnamCs; omeUs;lnamCs;omeAs;lnaTs;omeUs;lnamCs;omeUs; lnaGs;omeUs;lnaTs;omeAs;lnamCs;omeU |

| Name | Base sequence | Oligonucleotide chemistry pattern |
| --- | --- | --- |
| Oligo 45 | UATTTTTTAGATTCTC TTCU (SEQ ID NO: 13) | omeUs;lnaAs;lnaTs;dTs;lnaTs;dTs;lnaTs;dTs;lnaAs;dGs; lnaAs;dTs;lnaTs;dCs;lnaTs;dCs;lnaTs;dTs;lnamCs; omeU |
| Oligo 46 | UAUUUUUUAGAUUCU CUUCU (SEQ ID NO: 14) | omeUs;lnaAs;lnaTs;omeUs;lnaTs;omeUs;lnaTs;omeUs; lnaAs;omeGs;lnaAs;omeUs;lnaTs;omeCs;lnaTs;omeCs; lnaTs;omeUs;lnamCs;omeU |

Example 5: Synthetic OTC mRNA Construct with Synthetic UTR Sequence for Binding to GalNAc-Conjugated Oligonucleotides A synthetic OTC mRNA sequence was designed to include a Kozak consensus sequence, a mouse leader peptide, human OTC exons 2 to 10, the Hba-a1 3'UTR, and a synthetic UTR sequence with oligonucleotide binding sites (FIGS. 7, 9A and 9B-9C). The sequence and features of the mRNA are shown below (any T in the below sequence may be replaced with a U). The mouse leader peptide sequence was included to enhance transport to mitochondria in mice for animal testing. The mouse leader peptide sequence may be replaced with a human sequence (e.g., human OTC exon 1) for use in human cells or subjects (FIGS. 7, 9A and 9B-9C).

| FEATURES | Location/Qualifiers |
| --- | --- |
| 5'UTR | 1 . . . 14<br>/note="Kozak consensus seq" |
| mat_peptide | 15 . . . 1076<br>/note="OTC" |
| exon | 15 . . . 116<br>/note="Mouse Leader Peptide" |
| exon | 117 . . . 1076<br>/note="huOTC Exon2-10" |
| CDS | 1077 . . . 1106<br>/codon start=1<br>/product="Myc (human c-Myc oncogene) epitope tag"<br>/note="Myc"<br>/translation="EQKLISEEDL" |
| CDS | 1107 . . . 1130<br>/codon start=1<br>/product="FLAG(R) epitope tag, followed by an enterokinase cleavage site<br>/note="FLAG"<br>/translation="DYKDDDDK" |
| misc_feature | 1134 . . . 1226<br>/note="Hba-a1 3'UTR" |
| polyA_site | 1374 . . . 1493<br>/note="PolyA" |
| repeat_unit | 1239 . . . 1253<br>/note="Oligo Binding Site" |
| repeat_unit | 1266 . . . 1280<br>/note="Oligo Binding Site" |
| repeat_unit | 1293 . . . 1307<br>/note="Oligo Binding Site" |
| repeat_unit | 1320 . . . 1334<br>/note="Oligo Binding Site" |
| repeat_unit | 1347 . . . 1361<br>/note="Oligo Binding Site" |
| misc_feature | 1227 . . . 1238<br>/note="12 spacer" |
| misc_feature | 1254 . . . 1265<br>/note="12 spacer" |
| misc_feature | 1281 . . . 1292<br>/note="12 spacer" |
| misc_feature | 1308 . . . 1319<br>/note="12 spacer" | misc_feature 1335 . . . 1346
/note="12 spacer"

misc_feature 1362 . . . 1373
/note="12 spacer"

ORIGIN (SEQ ID NO: 15)

```
   1 gccgccgcga tcgcatgctg agcaacctga ggatcctgct gaacaacgcc gccctgagga 61 agggccacac cagcgtggtg aggcacttct ggtgcggcaa gcccgtgcag agccaggtgc 121 agctgaaggg ccgtgacctt ctcactctaa aaaactttac cggagaagaa attaaatata 181 tgctatggct atcagcagat ctgaaattta ggataaaaca gaaaggagag tatttgcctt 241 tattgcaagg gaagtcctta ggcatgattt ttgagaaaag aagtactcga caagattgt 301 ctacagaaac aggctttgca cttctgggag acatccttg ttttcttacc acacaagata 361 ttcatttggg tgtgaatgaa agtctcacgg acacggcccg tgtattgtct agcatggcag 421 atgcagtatt ggctcgagtg tataaacaat cagatttgga caccttgct aaagaagcat 481 ccatcccaat tatcaatggg ctgtcagatt tgtaccatcc tatccagatc ctggctgatt 541 acctcacgct ccaggaacac tatagctctc tgaaaggtct taccctcagc tggatcgggg 601 atgggaacaa tatcctgcac tccatcatga tgagcgcagc gaaattcgga atgcaccttc 661 aggcagctac tccaaagggt tatgagccgg atgctagtgt aaccaagttg gcagagcagt 721 atgccaaaga gaatggtacc aagctgttgc tgacaaatga tccattggaa gcagcgcatg 781 gaggcaatgt attaattaca gacacttgga taagcatggg acaagaagag gagaagaaaa 841 agcggctcca ggctttccaa ggttaccagg ttacaatgaa gactgctaaa gttgctgcct 901 ctgactggac attttacac tgcttgccca gaaagccaga agaagtggat gatgaagtct 961 tttattctcc tcgatcacta gtgttcccag aggcagaaaa cagaaagtgg acaatcatgg 1021 ctgtcatggt gtccctgctg acagattact cacctcagct ccagaagcct aaatttgagc 1081 agaaactcat ctcagaagag gatctggatt acaaggatga cgacgataag taagctgcct 1141 tctgcgggc ttgccttctg gccatgccct tcttctctcc cttgcacctg tacctcttgg 1201 tctttgaata aagcctgagt aggaagATTA CGTTGCACGG AGTGTGACAA TGGATTACGT

1261 TGCACGGAGT GTGACAATGG ATTACGTTGC ACGGAGTGTG ACAATGGATT ACGTTGCACG

1321 GAGTGTGACA ATGGATTACG TTGCACGGAG TGTGACAATG GATTACGTTG CACaaaaaaa 1381 aaaaaaaaaa aaaaaaaaaa aaaaaaaaaa aaaaaaaaaa aaaaaaaaaa aaaaaaaaaa 1441 aaaaaaaaaa aaaaaaaaaa aaaaaaaaaa aaaaaaaaaa aaaaaaaaaa aaa
```

A portion of the miR-122 sequence (a portion of the sequence of the microRNA not of a miR-122 binding site as would normally be found in naturally-occurring UTRs) was used as the GalNAc-conjugated oligonucleotide binding site in the synthetic UTR. The binding site was repeated 5 times with a 12 nucleotide spacer between each binding site. A single-stranded anti-miR122 oligonucleotide was designed to bind to the site. The sequence of the oligonucleotide is shown below. The oligonucleotide was conjugated to a GalNAc moiety as described in Example 1 (FIGS. 10A-10C). The key for abbreviations of the chemistry of the oligonucleotide is provided in Table 1.

Oligo Sequence for miR-122 Sequence-Containing Binding Site

| Name | Base sequence | Oligonucleotide chemistry pattern |
|---|---|---|
| Oligo 28 | CCATTGTCACACTCC (SEQ ID NO: 16) | lnamCs;dCs;lnaAs;dTs;dTs; lnaGs;lnaTs;dCs;dAs;lnamCs; dAs;lnamCs;dTs;lnamCs;lnamC |

Example 6: Assessment of Spacing and Number of Oligonucleotide Binding Sites in Synthetic mRNA Constructs The spacing of the binding sites within a synthetic 3'UTR is assessed for GalNAc-conjugated oligonucleotide binding efficacy and accessibility. The spacer sequence is designed to have a GC content of less than 40, a melting temperature ($T_m$) of less than 60 degrees Celsius, and minimal RNA structure as predicted from an RNA folding algorithm (minimum free energy). The RNA folding algorithm was RNAfold (University of Vienna, rna.tbi.univie.ac.at/cgi-bin/RNAWebSuite/RNAfold.cgi).

Figure 6:
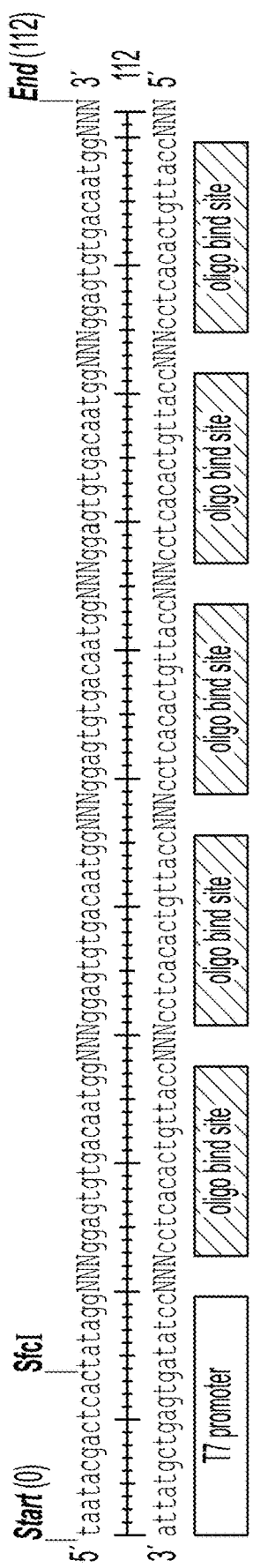
FIG. 6 is a schematic of a construct for generating a 3'UTR sequence using in vitro translation for assessment of binding efficiency and accessibility of multiple GalNAc-conjugated oligonucleotides to a candidate 3'UTR.
Figure 7:
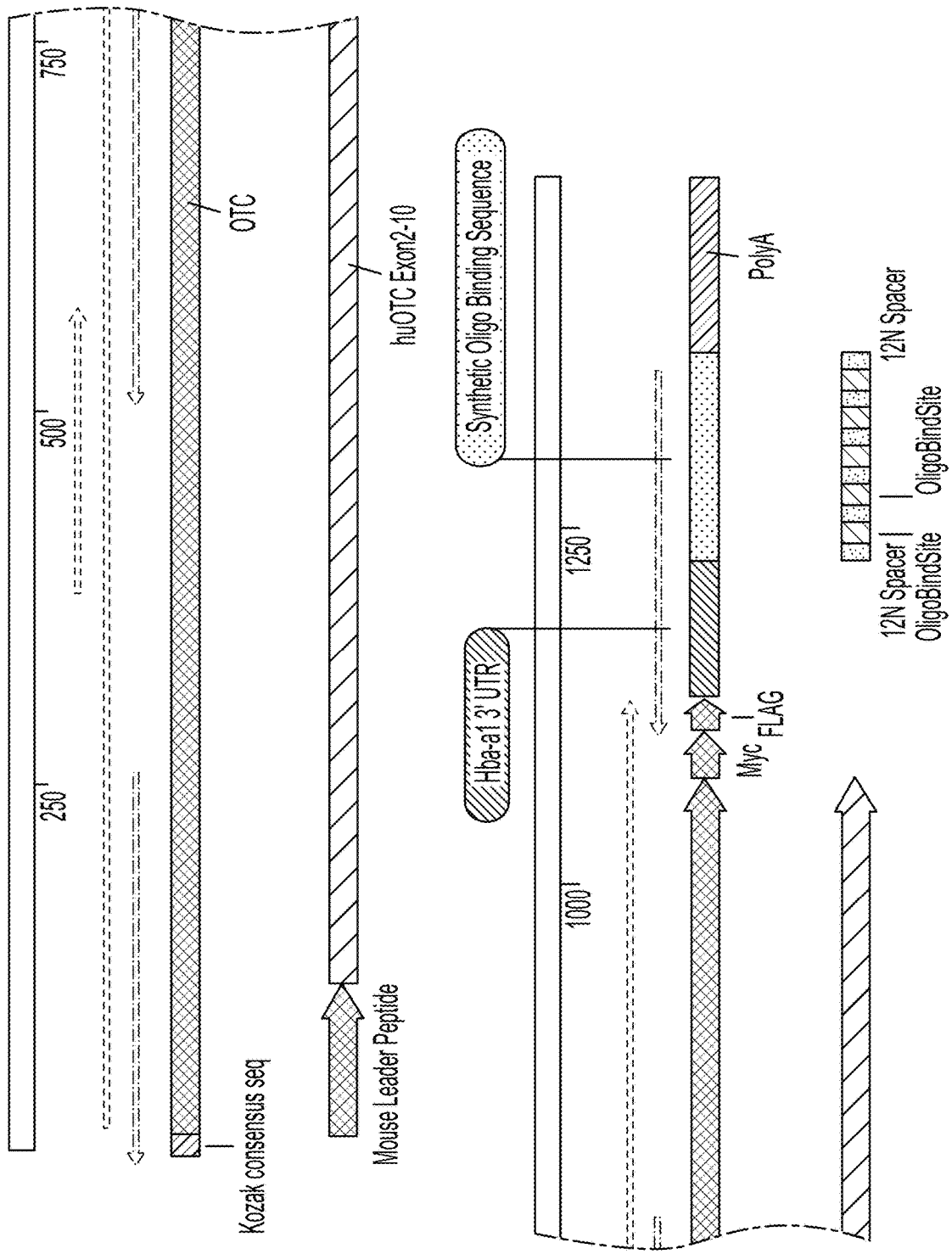
FIG. 7 is a schematic of an exemplary synthetic mRNA containing either a human OTC ORF or containing an ORF with a mouse leader peptide and human OTC exons 2-10, either way followed by a synthetic UTR that contains a Hba-a1 3'UTR and a synthetic UTR sequence for binding to a GalNAc-conjugated oligonucleotide with an exemplary arrangement of alternating 12 nucleotide spacers and oligonucleotide binding sites shown.

An in vitro translation system is used to generate the 3'UTR containing five copies of a GalNAc-conjugated oligonucleotide binding site, with varying spacer lengths (3, 6, 12, or 24 nucleotide lengths per spacer) between each binding site (FIG. 6). Each 3'UTR spacer variant is contacted with different concentrations of GalNAc-conjugated oligonucleotide under annealing or non-annealing conditions and is analyzed by RNA gel analysis to assess binding efficiency as indicated by the magnitude of the shift of the 3'UTR in the presence of the GalNAc-conjugated oligonucleotide.

Spacer lengths identified as having sufficient binding efficiency by RNA gel shift are then tested with a varying numbers of GalNAc-conjugated oligonucleotide binding sites to determine binding efficiency of different numbers of binding sites. An in vitro translation system is used to generate the 3'UTR containing 1, 3, 5 or 7 copies of a GalNAc-conjugated oligonucleotide binding site with the spacer lengths. Each 3'UTR binding site variant is contacted with different concentrations of GalNAc-conjugated oligonucleotide under annealing or non-annealing conditions and is analyzed by RNA gel analysis to assess binding efficiency as indicated by the magnitude of the shift of the 3'UTR in the presence of the GalNAc-conjugated oligonucleotide.

Example 7: In Vitro Testing of Synthetic OTC mRNA Constructs

Synthetic OTC mRNA constructs such as those described in Examples 4 and 5 are assessed for their ability to express OTC protein in vitro. Constructs containing synthetic UTRs such as those described in Example 5 are compared to constructs lacking the synthetic UTR (FIGS. 5A and 5B). Protein expression may be measured, e.g., using a cell-free translation systems such as rabbit reticulocyte lysates, wheat germ extracts, E. coli lysates or insect cell lysates or using cells such as Hepa1-6 cells or primary human hepatocytes. OTC protein levels from cells may be measured, e.g., by Sandwich ELISA using antibodies specific for human OTC which may include a capture antibody and a detection antibody-HRP conjugate. Assay plates may be coated with the capture antibody, after which cell lysates may be added be added to plates, followed by the detection antibody, and a signal may then be developed with TMB substrate, and colorimetric absorbance may be measured by a microplate plate reader.

Example 8: In Vivo Testing of Synthetic OTC mRNA Constructs

Figure 11:
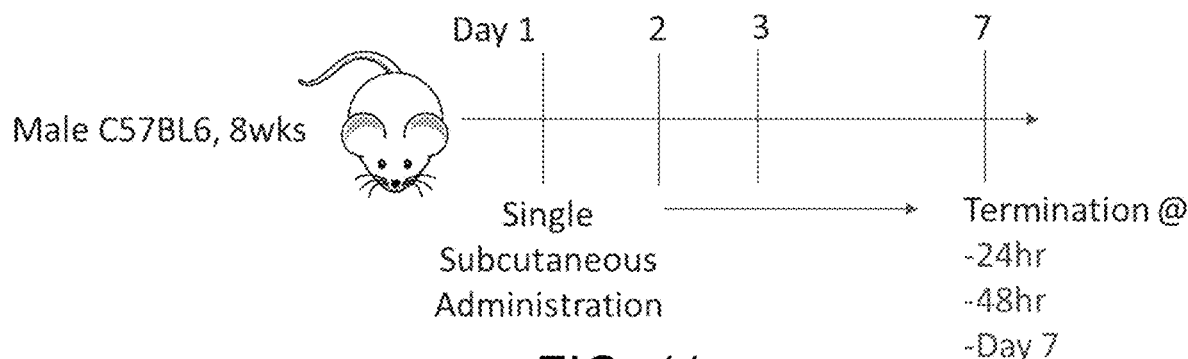
FIG. 11 is a diagram of an exemplary experiment utilizing mice in which 8 week old male C57BL6 mice are given a single subcutaneous administration of the synthetic mRNA complexed with the GalNAc-conjugated oligonucleotides or a control on day 1 and liver delivery of the synthetic mRNA is assessed at 24 hours, 48 hours and 7 days after administration.

Synthetic OTC mRNA constructs such as those described in Examples 4 and 5 are assessed for their ability to express OTC protein in the liver in vivo. Wild-type C57Bl/6 mice are given a single subcutaneous injection of the synthetic OTC mRNA constructs (either with or without GalNAc-conjugated oligonucleotides bound to the 3'UTR of the construct). The mice are euthanized at day 2, day 3 or day 7 post injection and the amount of synthetic mRNA present and the level of OTC protein is measured in the liver tissue of each mouse (FIG. 11). OTC protein levels from liver tissues may be measured, e.g., by Sandwich ELISA using antibodies specific for human OTC which may include a capture antibody and a detection antibody-HRP conjugate. Assay plates may be coated with the capture antibody, after which cell lysates may be added be added to plates, followed by the detection antibody, and a signal may then be developed with TMB substrate, and colorimetric absorbance may be measured by a microplate plate reader.

Without further elaboration, it is believed that one skilled in the art can, based on the description provided herein, utilize the present invention to its fullest extent. The specific embodiments are, therefore, to be construed as merely illustrative, and not limitative of the remainder of the disclosure in any way whatsoever. All publications cited herein are incorporated by reference for the purposes or subject matter referenced herein.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein.

In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A composition comprising:
   (a) a single-stranded oligonucleotide of 5 to 50 nucleotides in length covalently linked to a targeting moiety; and
   (b) a synthetic RNA comprising at least one binding region that is complementary to a contiguous stretch of at least 5 nucleotides of the oligonucleotide, wherein the single-stranded oligonucleotide is non-covalently associated with the synthetic RNA through the at least one binding region in the synthetic RNA; and
   wherein the targeting moiety comprises one or more one or more sugar moieties and has of one of the following formulae:

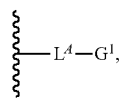 , 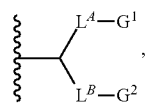 ,

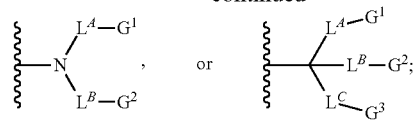

wherein:
   each instance of $L^A$, $L^B$, and $L^C$ is independently either absent or is a linker selected from the group consisting of substituted alkylene, substituted alkenylene, substituted alkynylene, substituted heteroalkylene, substituted heteroalkenylene, substituted heteroalkynylene, substituted acylene, substituted carbocyclylene, substituted heterocyclylene, substituted arylene, substituted heteroarylene, and combinations thereof; and
   each instance of $G^1$, $G^2$, and $G^3$ is independently a ligand.

2. The composition of claim 1, wherein the synthetic RNA comprises at least two copies of the binding region.

3. The composition of claim 2, wherein the copies of the binding region are separated from one another by a spacer region comprising at least one nucleotide.

4. The composition of claim 1, wherein the oligonucleotide comprises at least one modified internucleoside linkage.

5. The composition of claim 1, wherein the oligonucleotide comprises at least one modified nucleotide.

6. The composition of claim 1, wherein the targeting moiety comprises one or more ligands selected from a sugar moiety, a folate moiety, and a cell-penetrating peptide.

7. The composition of claim 1, wherein the targeting moiety comprises one or more N-acetylgalactosamine ligands.

8. The composition of claim 1, wherein each instance of $L^A$, $L^B$, and $L^C$ independently comprises a triazole diradical.

9. The composition of claim 1, wherein each instance of $G^1$, $G^2$, and $G^3$ is independently a ligand selected from a sugar moiety, a folate moiety, or a cell-penetrating peptide.

10. The composition of claim 1, wherein the targeting moiety comprises a group of the formula:

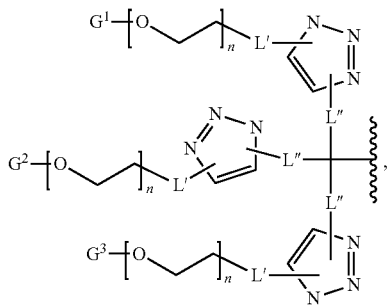

wherein:
each instance of L' and L" is independently a bond that is substituted alkylene or substituted heteroalkylene;
each instance of $G^1$, $G^2$, and $G^3$ is independently a sugar moiety, a folate moiety, or a cell-penetrating peptide; and
n is an integer from 1 to 10, inclusive.

11. The composition of claim 1, wherein the targeting moiety comprises a group of the following formula:

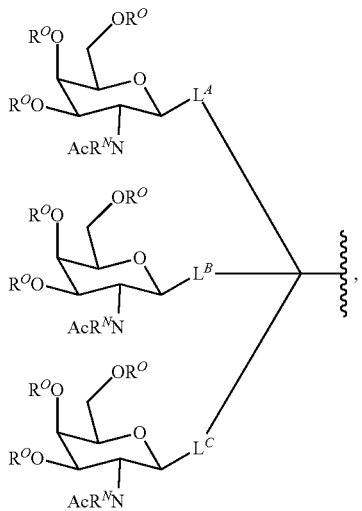

wherein:
each instance of $R^N$ is independently hydrogen, substituted alkyl, substituted acyl, or a nitrogen protecting group; and
each instance of $R^O$ is independently hydrogen, substituted alkyl, substituted acyl, or an oxygen protecting group.

12. The composition of claim 1, wherein the synthetic RNA comprises at least one modified nucleotide and/or modified internucleotide linkage.

13. A method of delivering a synthetic RNA to a cell, the method comprising delivering the composition of claim 1 to the cell.

14. A pharmaceutical preparation comprising a complex, wherein the complex comprises:
a single-stranded nucleic acid non-covalently associated with an oligonucleotide;
wherein the single-stranded nucleic acid is at least 50 to 10,000 nucleotides longer than the oligonucleotide; and
wherein the oligonucleotide is covalently linked to one or more targeting moieties, wherein the one or more targeting moieties is of one of the following formulae:

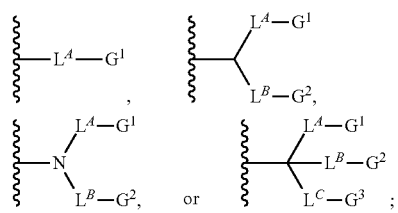

wherein:
each instance of $L^A$, $L^B$, and $L^C$ is independently either absent or is a linker selected from the group consisting of substituted alkylene, substituted alkenylene, substituted alkynylene, substituted heteroalkylene, substituted heteroalkenylene, substituted heteroalkynylene, substituted acylene, substituted carbocyclylene, substituted heterocyclylene, substituted arylene, substituted heteroarylene, and combinations thereof; and
each instance of $G^1$, $G^2$, and $G^3$ is independently a ligand.

15. The pharmaceutical preparation of claim 14, wherein the complex is of the following formula:

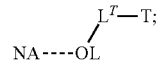

wherein:
NA is a single-stranded nucleic acid;
OL is an oligonucleotide;
----- represents one or more non-covalent bonds;
$L^T$ is a covalent bond or a linker moiety; and
T is a targeting moiety;
wherein the single-stranded nucleic acid is 50 to 10,000 nucleotides longer than the oligonucleotide.

16. The pharmaceutical preparation of claim 14, wherein the single-stranded nucleic acid is hybridized to the oligonucleotide.

17. The pharmaceutical preparation of claim 14, wherein the targeting moiety comprises one or more ligands selected from a sugar moiety, a folate moiety, and a cell-penetrating peptide.

18. The composition of claim 1, wherein the synthetic RNA is a synthetic mRNA that comprises at least one modified nucleotide and/or modified internucleotide linkage.

19. The composition of claim 18, wherein the synthetic mRNA comprises a 3' untranslated region (3'UTR).

20. The composition of claim 19, wherein the 3'UTR comprises one or more binding sites for binding to the single-stranded oligonucleotide.

21. The composition of claim 19, wherein the binding sites are not naturally present in human mRNA 3'UTRs.

* * * * *

SEQUENCE LISTING

```
<160> NUMBER OF SEQ ID NOS: 22

<210> SEQ ID NO 1
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 1
ccattgtcac actcc                                                        15

<210> SEQ ID NO 2
<211> LENGTH: 10
<212> TYPE: PRT
<213> ORGANISM: Artificial Sequence
```

```
<220> FEATURE:
<223> OTHER INFORMATION: Synthetic polypeptide

<400> SEQUENCE: 2

Lys Phe Phe Lys Phe Phe Lys Phe Phe Lys
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 4

Gly Arg Lys Lys Lys Arg Arg Gln Arg Arg Arg Tyr Lys
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 5

Arg Xaa Arg Arg Xaa Arg Arg Xaa Arg Arg Xaa Arg Xaa Asx
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (13)..(13)
<223> OTHER INFORMATION: Xaa can be any naturally occurring amino acid
```

```
<400> SEQUENCE: 6

Arg Phe Arg Arg Phe Arg Arg Phe Arg Arg Phe Arg Xaa Asx
1               5                   10

<210> SEQ ID NO 7
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 7
cgatcattca aa                                                          12

<210> SEQ ID NO 8
<211> LENGTH: 1363
<212> TYPE: DNA
<213> ORGANISM: Artificial Sequence
<220> FEATURE:
<223> OTHER INFORMATION: Synthetic polynucleotide

<400> SEQUENCE: 8
gccgccgcga tcgcatgctg agcaacctga ggatcctgct gaacaacgcc gccctgagga      60
agggccacac cagcgtggtg aggcacttct ggtgcggcaa gcccgtgcag agccaggtgc     120
agctgaaggg ccgtgacctt ctcactctaa aaactttac cggagaagaa attaaatata     180
tgctatggct atcagcagat ctgaaattta ggataaaaca gaaggagag tatttgcctt     240
tattgcaagg gaagtcctta ggcatgattt tgagaaaag aagtactcga caagattgt      300
ctacagaaac aggctttgca cttctgggag acatccttg ttttcttacc acacaagata     360
ttcatttggg tgtgaatgaa agtctcacgg cacggcccg tgtattgtct agcatggcag     420
atgcagtatt ggctcgagtg tataaacaat cagatttgga caccttgct aaagaagcat     480
ccatcccaat tatcaatggg ctgtcagatt tgtaccatcc tatccagatc ctggctgatt     540
acctcacgct ccaggaacac tatagctctc tgaaaggtct taccctcagc tggatcgggg     600
atgggaacaa tatcctgcac tccatcatga tgagcgcagc gaaattcgga atgcaccttc     660
aggcagctac tccaaagggt tatgagccgg atgctagtgt aaccaagttg gcagagcagt     720
atgccaaaga gaatggtacc aagctgttgc tgacaaatga tccattggaa gcagcgcatg     780
gaggcaatgt attaattaca gacacttgga taagcatggg acaagaagag gagaagaaaa     840
agcggctcca ggctttccaa ggttaccagg ttacaatgaa gactgctaaa gttgctgcct     900
ctgactggac atttttacac tgcttgccca gaaagccaga agagtggat gatgaagtct     960
tttattctcc tcgatcacta gtgttcccag aggcagaaaa cagaaagtgg acaatcatgg    1020
ctgtcatggt gtccctgctg acagattact cacctcagct ccagaagcct aaatttgagc    1080
agaaactcat ctcagaagag gatctggatt acaaggatga cgacgataag taatgttgtg    1140
ttacttgtca agaagaagc aatgttcttc agtaacagaa tgagttggtt tatggggaaa    1200
agagaagaga atctaaaaaa taaacaaatc cctaacacgt ggtaaaaaa aaaaaaaaa    1260
aaaaaaaaaa aaaaaaaaaa aaaaaaaaaa aaaaaaaaa aaaaaaaaaa aaaaaaaaa    1320
aaaaaaaaaa aaaaaaaaaa aaaaaaaaaa aaaaaaaaa aaa                      1363

<210> SEQ ID NO 9
<211> LENGTH: 20
<212> TYPE: DNA
<213> ORGANISM: Artificial Sequence
<220> FEATURE:
```

```
<223> OTHER INFORMATION: Synthetic polynucleotide
<220> FEATURE:
<221> NAME/KEY: misc_feature
<222> LOCATION: (1)..(1)
<223> OTHER INFORMATION: 2'-O-methyl cytosine nucleotide w/3'
      phosphorothioate
<220> FEATURE:
<221> NAME/KEY: misc_feature
<222> LOCATION: (2)..(2)
<223> OTHER INFORMATION: adenosine LNA w/3' phosphorothioate
<220> FEATURE:
<221> NAME/KEY: misc_feature
<222> LOCATION: (3)..(3)
<223> OTHER INFORMATION: thymidine LNA w/3' phosphorothioate
<220> FEATURE:
<221> NAME/KEY: misc_feature
<222> LOCATION: (4)..(4)
<223> OTHER INFORMATION: thymidine DNA w/3' phosphorothioate
<220> FEATURE:
<221> NAME/KEY: misc_feature
<222> LOCATION: (5)..(5)
<223> OTHER INFORMATION: guanosine LNA w/3' phosphorothioate
<220> FEATURE:
<221> NAME/KEY: misc_feature
<222> LOCATION: (6)..(6)
<223> OTHER INFORMATION: cytosine DNA w/3' phosphorothioate
<220> FEATURE:
<221> NAME/KEY: misc_feature
<222> LOCATION: (7)..(7)
<223> OTHER INFORMATION: thymidine LNA w/3' phosphorothioate
<220> FEATURE:
<221> NAME/KEY: misc_feature
<222> LOCATION: (8)..(8)
<223> OTHER INFORMATION: thymidine DNA w/3' phosphorothioate
<220> FEATURE:
<221> NAME/KEY: misc_feature
<222> LOCATION: (9)..(9)
<223> OTHER INFORMATION: 5-methyl cytosine LNA w/3' phosphorothioate
<220> FEATURE:
<221> NAME/KEY: misc_feature
<222> LOCATION: (10)..(10)
<223> OTHER INFORMATION: thymidine DNA w/3' phosphorothioate
<220> FEATURE:
<221> NAME/KEY: misc_feature
<222> LOCATION: (11)..(11)
<223> OTHER INFORMATION: thymidine LNA w/3' phosphorothioate
<220> FEATURE:
<221> NAME/KEY: misc_feature
<222> LOCATION: (12)..(12)
<223> OTHER INFORMATION: thymidine DNA w/3' phosphorothioate
<220> FEATURE:
<221> NAME/KEY: misc_feature
<222> LOCATION: (13)..(13)
<223> OTHER INFORMATION: 5-methyl cytosine LNA w/3' phosphorothioate
<220> FEATURE:
<221> NAME/KEY: misc_feature
<222> LOCATION: (14)..(14)
<223> OTHER INFORMATION: thymidine DNA w/3' phosphorothioate
<220> FEATURE:
<221> NAME/KEY: misc_feature
<222> LOCATION: (15)..(15)
<223> OTHER INFORMATION: thymidine LNA w/3' phosphorothioate
<220> FEATURE:
<221> NAME/KEY: misc_feature
<222> LOCATION: (16)..(16)
<223> OTHER INFORMATION: guanosine DNA w/3' phosphorothioate
<220> FEATURE:
<221> NAME/KEY: misc_feature
<222> LOCATION: (17)..(17)
<223> OTHER INFORMATION: adenosine LNA w/3' phosphorothioate
<220> FEATURE:
<221> NAME/KEY: misc_feature
<222> LOCATION: (18)..(18)
<223> OTHER INFORMATION: cytosine DNA w/3' phosphorothioate
<220> FEATURE:
<221> NAME/KEY: misc_feature
<222> LOCATION: (19)..(19)
<223> OTHER INFORMATION: adenosine LNA
<220> FEATURE:
```

<221> NAME/KEY: misc_feature
<222> LOCATION: (20)..(20)
<223> OTHER INFORMATION: 2'-O-methyl adenosine nucleotide

<400> SEQUENCE: 9
cattgcttct ttcttgacaa                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 2'-O-methyl cytosine nucleotide w/3'
      phosphorothioate
<220> FEATURE:
<221> NAME/KEY: misc_feature
<222> LOCATION: (2)..(2)
<223> OTHER INFORMATION: adenosine LNA w/3' phosphorothioate
<220> FEATURE:
<221> NAME/KEY: misc_feature
<222> LOCATION: (3)..(3)
<223> OTHER INFORMATION: thymidine LNA w/3' phosphorothioate
<220> FEATURE:
<221> NAME/KEY: misc_feature
<222> LOCATION: (4)..(4)
<223> OTHER INFORMATION: 2'-O-methyl thymidine nucleotide w/3'
      phosphorothioate
<220> FEATURE:
<221> NAME/KEY: misc_feature
<222> LOCATION: (5)..(5)
<223> OTHER INFORMATION: guanosine LNA w/3' phosphorothioate
<220> FEATURE:
<221> NAME/KEY: misc_feature
<222> LOCATION: (6)..(6)
<223> OTHER INFORMATION: 2'-O-methyl cytosine nucleotide w/3'
      phosphorothioate
<220> FEATURE:
<221> NAME/KEY: misc_feature
<222> LOCATION: (7)..(7)
<223> OTHER INFORMATION: thymidine LNA w/3' phosphorothioate
<220> FEATURE:
<221> NAME/KEY: misc_feature
<222> LOCATION: (8)..(8)
<223> OTHER INFORMATION: 2?-O-methyl thymidine nucleotide w/3'
      phosphorothioate
<220> FEATURE:
<221> NAME/KEY: misc_feature
<222> LOCATION: (9)..(9)
<223> OTHER INFORMATION: cytosine LNA w/3' phosphorothioate
<220> FEATURE:
<221> NAME/KEY: misc_feature
<222> LOCATION: (10)..(10)
<223> OTHER INFORMATION: 2'-O-methyl thymidine nucleotide w/3'
      phosphorothioate
<220> FEATURE:
<221> NAME/KEY: misc_feature
<222> LOCATION: (11)..(11)
<223> OTHER INFORMATION: thymidine LNA w/3' phosphorothioate
<220> FEATURE:
<221> NAME/KEY: misc_feature
<222> LOCATION: (12)..(12)
<223> OTHER INFORMATION: 2'-O-methyl thymidine nucleotide w/3'
      phosphorothioate
<220> FEATURE:
<221> NAME/KEY: misc_feature
<222> LOCATION: (13)..(13)
<223> OTHER INFORMATION: 5-methyl cytosine LNA w/3' phosphorothioate
<220> FEATURE:
<221> NAME/KEY: misc_feature
<222> LOCATION: (14)..(14)
<223> OTHER INFORMATION: 2'-O-methyl thymidine nucleotide w/3'
      phosphorothioate
<220> FEATURE:

-continued

```
<221> NAME/KEY: misc_feature
<222> LOCATION: (15)..(15)
<223> OTHER INFORMATION: thymidine LNA w/3' phosphorothioate
<220> FEATURE:
<221> NAME/KEY: misc_feature
<222> LOCATION: (16)..(16)
<223> OTHER INFORMATION: 2'-O-methyl guanosine nucleotide w/3'
      phosphorothioate
<220> FEATURE:
<221> NAME/KEY: misc_feature
<222> LOCATION: (17)..(17)
<223> OTHER INFORMATION: adenosine LNA w/3' phosphorothioate
<220> FEATURE:
<221> NAME/KEY: misc_feature
<222> LOCATION: (18)..(18)
<223> OTHER INFORMATION: 2'-O-methyl cytosine nucleotide w/3'
      phosphorothioate
<220> FEATURE:
<221> NAME/KEY: misc_feature
<222> LOCATION: (19)..(19)
<223> OTHER INFORMATION: adenosine LNA w/3' phosphorothioate
<220> FEATURE:
<221> NAME/KEY: misc_feature
<222> LOCATION: (20)..(20)
<223> OTHER INFORMATION: 2'-O-methyl adenosine nucleotide

<400> SEQUENCE: 10
catugctucu tucutgacaa                                            20

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 2'-O-methyl adenosine nucleotide w/3'
      phosphorothioate
<220> FEATURE:
<221> NAME/KEY: misc_feature
<222> LOCATION: (2)..(2)
<223> OTHER INFORMATION: adenosine LNA w/3' phosphorothioate
<220> FEATURE:
<221> NAME/KEY: misc_feature
<222> LOCATION: (3)..(3)
<223> OTHER INFORMATION: 5-methyl cytosine LNA w/3' phosphorothioate
<220> FEATURE:
<221> NAME/KEY: misc_feature
<222> LOCATION: (4)..(4)
<223> OTHER INFORMATION: cytosine DNA w/3' phosphorothioate
<220> FEATURE:
<221> NAME/KEY: misc_feature
<222> LOCATION: (5)..(5)
<223> OTHER INFORMATION: adenosine LNA w/3' phosphorothioate
<220> FEATURE:
<221> NAME/KEY: misc_feature
<222> LOCATION: (6)..(6)
<223> OTHER INFORMATION: adenosine DNA w/3' phosphorothioate
<220> FEATURE:
<221> NAME/KEY: misc_feature
<222> LOCATION: (7)..(7)
<223> OTHER INFORMATION: cytosine LNA w/3' phosphorothioate
<220> FEATURE:
<221> NAME/KEY: misc_feature
<222> LOCATION: (8)..(8)
<223> OTHER INFORMATION: thymidine DNA w/3' phosphorothioate
<220> FEATURE:
<221> NAME/KEY: misc_feature
<222> LOCATION: (9)..(9)
<223> OTHER INFORMATION: cytosine LNA w/3' phosphorothioate
<220> FEATURE:
<221> NAME/KEY: misc_feature
<222> LOCATION: (10)..(10)
<223> OTHER INFORMATION: adenosine DNA w/3' phosphorothioate
<220> FEATURE:
```

-continued

```
<221> NAME/KEY: misc_feature
<222> LOCATION: (11)..(11)
<223> OTHER INFORMATION: thymidine LNA w/3' phosphorothioate
<220> FEATURE:
<221> NAME/KEY: misc_feature
<222> LOCATION: (12)..(12)
<223> OTHER INFORMATION: thymidine DNA w/3' phosphorothioate
<220> FEATURE:
<221> NAME/KEY: misc_feature
<222> LOCATION: (13)..(13)
<223> OTHER INFORMATION: cytosine LNA w/3' phosphorothioate
<220> FEATURE:
<221> NAME/KEY: misc_feature
<222> LOCATION: (14)..(14)
<223> OTHER INFORMATION: thymidine DNA w/3' phosphorothioate
<220> FEATURE:
<221> NAME/KEY: misc_feature
<222> LOCATION: (15)..(15)
<223> OTHER INFORMATION: guanosine LNA w/3' phosphorothioate
<220> FEATURE:
<221> NAME/KEY: misc_feature
<222> LOCATION: (16)..(16)
<223> OTHER INFORMATION: thymidine DNA w/3' phosphorothioate
<220> FEATURE:
<221> NAME/KEY: misc_feature
<222> LOCATION: (17)..(17)
<223> OTHER INFORMATION: thymidine LNA w/3' phosphorothioate
<220> FEATURE:
<221> NAME/KEY: misc_feature
<222> LOCATION: (18)..(18)
<223> OTHER INFORMATION: adenosine DNA w/3' phosphorothioate
<220> FEATURE:
<221> NAME/KEY: misc_feature
<222> LOCATION: (19)..(19)
<223> OTHER INFORMATION: 5-methyl cytosine LNA w/3' phosphorothioate
<220> FEATURE:
<221> NAME/KEY: misc_feature
<222> LOCATION: (20)..(20)
<223> OTHER INFORMATION: 2'-O-methyl uracil nucleotide

<400> SEQUENCE: 11
aaccaactca ttctgttacu                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 2'-O-methyl adenosine nucleotide w/3'
      phosphorothioate
<220> FEATURE:
<221> NAME/KEY: misc_feature
<222> LOCATION: (2)..(2)
<223> OTHER INFORMATION: adenosine LNA w/3' phosphorothioate
<220> FEATURE:
<221> NAME/KEY: misc_feature
<222> LOCATION: (3)..(3)
<223> OTHER INFORMATION: 5-methyl cytosine LNA w/3' phosphorothioate
<220> FEATURE:
<221> NAME/KEY: misc_feature
<222> LOCATION: (4)..(4)
<223> OTHER INFORMATION: 2'-O-methyl cytosine nucleotide w/3'
      phosphorothioate
<220> FEATURE:
<221> NAME/KEY: misc_feature
<222> LOCATION: (5)..(5)
<223> OTHER INFORMATION: adenosine LNA w/3' phosphorothioate
<220> FEATURE:
<221> NAME/KEY: misc_feature
<222> LOCATION: (6)..(6)
<223> OTHER INFORMATION: 2'-O-methyl adenosine nucleotide w/3'
      phosphorothioate
<220> FEATURE:
```

```
<221> NAME/KEY: misc_feature
<222> LOCATION: (7)..(7)
<223> OTHER INFORMATION: 5-methyl cytosine LNA w/3' phosphorothioate
<220> FEATURE:
<221> NAME/KEY: misc_feature
<222> LOCATION: (8)..(8)
<223> OTHER INFORMATION: 2'-O-methyl thymidine nucleotide w/3'
      phosphorothioate
<220> FEATURE:
<221> NAME/KEY: misc_feature
<222> LOCATION: (9)..(9)
<223> OTHER INFORMATION: 5-methyl cytosine LNA w/3' phosphorothioate
<220> FEATURE:
<221> NAME/KEY: misc_feature
<222> LOCATION: (10)..(10)
<223> OTHER INFORMATION: 2'-O-methyl adenosine nucleotide w/3'
      phosphorothioate
<220> FEATURE:
<221> NAME/KEY: misc_feature
<222> LOCATION: (11)..(11)
<223> OTHER INFORMATION: thymidine LNA w/3' phosphorothioate
<220> FEATURE:
<221> NAME/KEY: misc_feature
<222> LOCATION: (12)..(12)
<223> OTHER INFORMATION: 2'-O-methyl thymidine nucleotide w/3'
      phosphorothioate
<220> FEATURE:
<221> NAME/KEY: misc_feature
<222> LOCATION: (13)..(13)
<223> OTHER INFORMATION: 5-methyl cytosine LNA w/3' phosphorothioate
<220> FEATURE:
<221> NAME/KEY: misc_feature
<222> LOCATION: (14)..(14)
<223> OTHER INFORMATION: 2'-O-methyl thymidine nucleotide w/3'
      phosphorothioate
<220> FEATURE:
<221> NAME/KEY: misc_feature
<222> LOCATION: (15)..(15)
<223> OTHER INFORMATION: guanosine LNA w/3' phosphorothioate
<220> FEATURE:
<221> NAME/KEY: misc_feature
<222> LOCATION: (16)..(16)
<223> OTHER INFORMATION: 2'-O-methyl thymidine nucleotide w/3'
      phosphorothioate
<220> FEATURE:
<221> NAME/KEY: misc_feature
<222> LOCATION: (17)..(17)
<223> OTHER INFORMATION: thymidine LNA w/3' phosphorothioate
<220> FEATURE:
<221> NAME/KEY: misc_feature
<222> LOCATION: (18)..(18)
<223> OTHER INFORMATION: 2'-O-methyl adenosine nucleotide w/3'
      phosphorothioate
<220> FEATURE:
<221> NAME/KEY: misc_feature
<222> LOCATION: (19)..(19)
<223> OTHER INFORMATION: 2'-O-methyl cytosine nucleotide w/3'
      phosphorothioate
<220> FEATURE:
<221> NAME/KEY: misc_feature
<222> LOCATION: (20)..(20)
<223> OTHER INFORMATION: 2'-O-methyl uracil nucleotide

<400> SEQUENCE: 12
aaccaacuca tucugutacu                                                 20

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 2'-O-methyl thymidine nucleotide w/3'
      phosphorothioate
```

```
<220> FEATURE:
<221> NAME/KEY: misc_feature
<222> LOCATION: (2)..(2)
<223> OTHER INFORMATION: adenosine LNA w/3' phosphorothioate
<220> FEATURE:
<221> NAME/KEY: misc_feature
<222> LOCATION: (3)..(3)
<223> OTHER INFORMATION: thymidine LNA w/3' phosphorothioate
<220> FEATURE:
<221> NAME/KEY: misc_feature
<222> LOCATION: (4)..(4)
<223> OTHER INFORMATION: thymidine DNA w/3' phosphorothioate
<220> FEATURE:
<221> NAME/KEY: misc_feature
<222> LOCATION: (5)..(5)
<223> OTHER INFORMATION: thymidine LNA w/3' phosphorothioate
<220> FEATURE:
<221> NAME/KEY: misc_feature
<222> LOCATION: (6)..(6)
<223> OTHER INFORMATION: thymidine DNA w/3' phosphorothioate
<220> FEATURE:
<221> NAME/KEY: misc_feature
<222> LOCATION: (7)..(7)
<223> OTHER INFORMATION: thymidine LNA w/3' phosphorothioate
<220> FEATURE:
<221> NAME/KEY: misc_feature
<222> LOCATION: (8)..(8)
<223> OTHER INFORMATION: thymidine DNA w/3' phosphorothioate
<220> FEATURE:
<221> NAME/KEY: misc_feature
<222> LOCATION: (9)..(9)
<223> OTHER INFORMATION: adenosine LNA w/3' phosphorothioate
<220> FEATURE:
<221> NAME/KEY: misc_feature
<222> LOCATION: (10)..(10)
<223> OTHER INFORMATION: guanosine DNA w/3' phosphorothioate
<220> FEATURE:
<221> NAME/KEY: misc_feature
<222> LOCATION: (11)..(11)
<223> OTHER INFORMATION: adenosine LNA w/3' phosphorothioate
<220> FEATURE:
<221> NAME/KEY: misc_feature
<222> LOCATION: (12)..(12)
<223> OTHER INFORMATION: thymidine DNA w/3' phosphorothioate
<220> FEATURE:
<221> NAME/KEY: misc_feature
<222> LOCATION: (13)..(13)
<223> OTHER INFORMATION: thymidine LNA w/3' phosphorothioate
<220> FEATURE:
<221> NAME/KEY: misc_feature
<222> LOCATION: (14)..(14)
<223> OTHER INFORMATION: cytosine DNA w/3' phosphorothioate
<220> FEATURE:
<221> NAME/KEY: misc_feature
<222> LOCATION: (15)..(15)
<223> OTHER INFORMATION: thymidine LNA w/3' phosphorothioate
<220> FEATURE:
<221> NAME/KEY: misc_feature
<222> LOCATION: (16)..(16)
<223> OTHER INFORMATION: cytosine DNA w/3' phosphorothioate
<220> FEATURE:
<221> NAME/KEY: misc_feature
<222> LOCATION: (17)..(17)
<223> OTHER INFORMATION: thymidine LNA w/3' phosphorothioate
<220> FEATURE:
<221> NAME/KEY: misc_feature
<222> LOCATION: (18)..(18)
<223> OTHER INFORMATION: thymidine DNA w/3' phosphorothioate
<220> FEATURE:
<221> NAME/KEY: misc_feature
<222> LOCATION: (19)..(19)
<223> OTHER INFORMATION: 5-methyl cytosine LNA w/3' phosphorothioate
<220> FEATURE:
<221> NAME/KEY: misc_feature
<222> LOCATION: (20)..(20)
<223> OTHER INFORMATION: 2'-O-methyl uracil nucleotide

<400> SEQUENCE: 13
``` uatttttag attctcttcu 20

```
<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 2'-O-methyl thymidine nucleotide w/3'
      phosphorothioate
<220> FEATURE:
<221> NAME/KEY: misc_feature
<222> LOCATION: (2)..(2)
<223> OTHER INFORMATION: adenosine LNA w/3' phosphorothioate
<220> FEATURE:
<221> NAME/KEY: misc_feature
<222> LOCATION: (3)..(3)
<223> OTHER INFORMATION: thymidine LNA w/3' phosphorothioate
<220> FEATURE:
<221> NAME/KEY: misc_feature
<222> LOCATION: (4)..(4)
<223> OTHER INFORMATION: 2'-O-methyl thymidine nucleotide w/3'
      phosphorothioate
<220> FEATURE:
<221> NAME/KEY: misc_feature
<222> LOCATION: (5)..(5)
<223> OTHER INFORMATION: thymidine LNA w/3' phosphorothioate
<220> FEATURE:
<221> NAME/KEY: misc_feature
<222> LOCATION: (6)..(6)
<223> OTHER INFORMATION: 2'-O-methyl thymidine nucleotide w/3'
      phosphorothioate
<220> FEATURE:
<221> NAME/KEY: misc_feature
<222> LOCATION: (7)..(7)
<223> OTHER INFORMATION: thymidine LNA w/3' phosphorothioate
<220> FEATURE:
<221> NAME/KEY: misc_feature
<222> LOCATION: (8)..(8)
<223> OTHER INFORMATION: 2'-O-methyl uracil nucleotide
<220> FEATURE:
<221> NAME/KEY: misc_feature
<222> LOCATION: (9)..(9)
<223> OTHER INFORMATION: adenosine LNA w/3' phosphorothioate
<220> FEATURE:
<221> NAME/KEY: misc_feature
<222> LOCATION: (10)..(10)
<223> OTHER INFORMATION: 2'-O-methyl guanosine nucleotide w/3'
      phosphorothioate
<220> FEATURE:
<221> NAME/KEY: misc_feature
<222> LOCATION: (11)..(11)
<223> OTHER INFORMATION: adenosine LNA w/3' phosphorothioate
<220> FEATURE:
<221> NAME/KEY: misc_feature
<222> LOCATION: (12)..(12)
<223> OTHER INFORMATION: 2'-O-methyl thymidine nucleotide w/3'
      phosphorothioate
<220> FEATURE:
<221> NAME/KEY: misc_feature
<222> LOCATION: (13)..(13)
<223> OTHER INFORMATION: thymidine LNA w/3' phosphorothioate
<220> FEATURE:
<221> NAME/KEY: misc_feature
<222> LOCATION: (14)..(14)
<223> OTHER INFORMATION: 2'-O-methyl cytosine nucleotide w/3'
      phosphorothioate
<220> FEATURE:
<221> NAME/KEY: misc_feature
<222> LOCATION: (15)..(15)
<223> OTHER INFORMATION: thymidine LNA w/3' phosphorothioate
<220> FEATURE:
<221> NAME/KEY: misc_feature
<222> LOCATION: (16)..(16)
<223> OTHER INFORMATION: 2'-O-methyl cytosine nucleotide w/3'
```

```
      phosphorothioate
<220> FEATURE:
<221> NAME/KEY: misc_feature
<222> LOCATION: (17)..(17)
<223> OTHER INFORMATION: thymidine LNA w/3' phosphorothioate
<220> FEATURE:
<221> NAME/KEY: misc_feature
<222> LOCATION: (18)..(18)
<223> OTHER INFORMATION: 2'-O-methyl thymidine nucleotide w/3'
      phosphorothioate
<220> FEATURE:
<221> NAME/KEY: misc_feature
<222> LOCATION: (19)..(19)
<223> OTHER INFORMATION: 5-methyl cytosine LNA w/3' phosphorothioate
<220> FEATURE:
<221> NAME/KEY: misc_feature
<222> LOCATION: (20)..(20)
<223> OTHER INFORMATION: 2'-O-methyl uracil nucleotide

<400> SEQUENCE: 14
uatututuag autctctucu                                              20

<210> SEQ ID NO 15
<211> LENGTH: 1493
<212> TYPE: DNA
<213> ORGANISM: Artificial Sequence
<220> FEATURE:
<223> OTHER INFORMATION: Synthetic polynucleotide

<400> SEQUENCE: 15
gccgccgcga tcgcatgctg agcaacctga ggatcctgct gaacaacgcc gccctgagga    60
agggccacac cagcgtggtg aggcacttct ggtgcggcaa gcccgtgcag agccaggtgc   120
agctgaaggg ccgtgacctt ctcactctaa aaaactttac cggagaagaa attaaatata   180
tgctatggct atcagcagat ctgaaattta ggataaaaca gaaggagag tatttgcctt    240 tattgcaagg gaagtcctta ggcatgattt ttgagaaaag aagtactcga acaagattgt   300
ctacagaaac aggctttgca cttctgggag gacatccttg ttttcttacc acacaagata   360
ttcatttggg tgtgaatgaa agtctcacgg acacggcccg tgtattgtct agcatggcag   420
atgcagtatt ggctcgagtg tataaacaat cagatttgga cacccttgct aaagaagcat   480
ccatcccaat tatcaatggg ctgtcagatt tgtaccatcc tatccagatc ctggctgatt   540
acctcacgct ccaggaacac tatagctctc tgaaaggtct taccctcagc tggatcgggg   600
atgggaacaa tatcctgcac tccatcatga tgagcgcagc gaaattcgga atgcaccttc   660
aggcagctac tccaaagggt tatgagccgg atgctagtgt aaccaagttg gcagagcagt   720
atgccaaaga gaatggtacc aagctgttgc tgacaaatga tccattggaa gcagcgcatg   780
gaggcaatgt attaattaca gacacttgga taagcatggg acaagaagag gagaagaaaa   840
agcggctcca ggctttccaa ggttaccagg ttacaatgaa gactgctaaa gttgctgcct   900
ctgactggac attttacac tgcttgccca gaaagccaga agaagtggat gatgaagtct    960
tttattctcc tcgatcacta gtgttccag aggcagaaaa cagaaagtgg acaatcatgg   1020
ctgtcatggt gtccctgctg acagattact cacctcagct ccagaagcct aaatttgagc  1080
agaaactcat ctcagaagag gatctggatt acaaggatga cgacgataag taagctgcct  1140 tctgcgggc ttgccttctg gccatgccct tcttctctcc cttgcacctg tacctcttgg   1200
tctttgaata aagcctgagt aggaagatta cgttgcacgg agtgtgacaa tggattacgt  1260
tgcacggagt gtgacaatgg attacgttgc acggagtgtg acaatggatt acgttgcacg  1320
gagtgtgaca atgattacg ttgcacggag tgtgacaatg gattacgttg cacaaaaaaa   1380
```
aaaaaaaaaa aaaaaaaaaa aaaaaaaaaa aaaaaaaaaa aaaaaaaaaa aaaaaaaaaa    1440
aaaaaaaaaa aaaaaaaaaa aaaaaaaaaa aaaaaaaaaa aaaaaaaaaa aaa           1493

```
<210> SEQ ID NO 16
<211> LENGTH: 15
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 5-methyl cytosine LNA w/3' phosphorothioate
<220> FEATURE:
<221> NAME/KEY: misc_feature
<222> LOCATION: (2)..(2)
<223> OTHER INFORMATION: cytosine DNA w/3' phosphorothioate
<220> FEATURE:
<221> NAME/KEY: misc_feature
<222> LOCATION: (3)..(3)
<223> OTHER INFORMATION: adenosine LNA w/3' phosphorothioate
<220> FEATURE:
<221> NAME/KEY: misc_feature
<222> LOCATION: (4)..(4)
<223> OTHER INFORMATION: thymidine DNA w/3' phosphorothioate
<220> FEATURE:
<221> NAME/KEY: misc_feature
<222> LOCATION: (5)..(5)
<223> OTHER INFORMATION: thymidine DNA w/3' phosphorothioate
<220> FEATURE:
<221> NAME/KEY: misc_feature
<222> LOCATION: (6)..(6)
<223> OTHER INFORMATION: guanosine LNA w/3' phosphorothioate
<220> FEATURE:
<221> NAME/KEY: misc_feature
<222> LOCATION: (7)..(7)
<223> OTHER INFORMATION: thymidine LNA w/3' phosphorothioate
<220> FEATURE:
<221> NAME/KEY: misc_feature
<222> LOCATION: (8)..(8)
<223> OTHER INFORMATION: cytosine DNA w/3' phosphorothioate
<220> FEATURE:
<221> NAME/KEY: misc_feature
<222> LOCATION: (9)..(9)
<223> OTHER INFORMATION: adenosine DNA w/3' phosphorothioate
<220> FEATURE:
<221> NAME/KEY: misc_feature
<222> LOCATION: (10)..(10)
<223> OTHER INFORMATION: 5-methyl cytosine LNA w/3' phosphorothioate
<220> FEATURE:
<221> NAME/KEY: misc_feature
<222> LOCATION: (11)..(11)
<223> OTHER INFORMATION: adenosine DNA w/3' phosphorothioate
<220> FEATURE:
<221> NAME/KEY: misc_feature
<222> LOCATION: (12)..(12)
<223> OTHER INFORMATION: 5-methyl cytosine LNA w/3' phosphorothioate
<220> FEATURE:
<221> NAME/KEY: misc_feature
<222> LOCATION: (13)..(13)
<223> OTHER INFORMATION: thymidine DNA w/3' phosphorothioate
<220> FEATURE:
<221> NAME/KEY: misc_feature
<222> LOCATION: (14)..(14)
<223> OTHER INFORMATION: 5-methyl cytosine LNA w/3' phosphorothioate
<220> FEATURE:
<221> NAME/KEY: misc_feature
<222> LOCATION: (15)..(15)
<223> OTHER INFORMATION: 5-methyl cytosine LNA

<400> SEQUENCE: 16
ccattgtcac actcc                                                      15

<210> SEQ ID NO 17
<211> LENGTH: 112
```

```
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (20)..(22)
<223> OTHER INFORMATION: n is a, c, g, or t
<220> FEATURE:
<221> NAME/KEY: misc_feature
<222> LOCATION: (38)..(40)
<223> OTHER INFORMATION: n is a, c, g, or t
<220> FEATURE:
<221> NAME/KEY: misc_feature
<222> LOCATION: (56)..(58)
<223> OTHER INFORMATION: n is a, c, g, or t
<220> FEATURE:
<221> NAME/KEY: misc_feature
<222> LOCATION: (74)..(76)
<223> OTHER INFORMATION: n is a, c, g, or t
<220> FEATURE:
<221> NAME/KEY: misc_feature
<222> LOCATION: (92)..(94)
<223> OTHER INFORMATION: n is a, c, g, or t
<220> FEATURE:
<221> NAME/KEY: misc_feature
<222> LOCATION: (110)..(112)
<223> OTHER INFORMATION: n is a, c, g, or t

<400> SEQUENCE: 17
taatacgact cactataggn nnggagtgtg acaatggnnn ggagtgtgac aatggnnngg      60
agtgtgacaa tggnnnggag tgtgacaatg gnnnggagtg tgacaatggn nn            112

<210> SEQ ID NO 18
<211> LENGTH: 112
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t
<220> FEATURE:
<221> NAME/KEY: misc_feature
<222> LOCATION: (37)..(39)
<223> OTHER INFORMATION: n is a, c, g, or t
<220> FEATURE:
<221> NAME/KEY: misc_feature
<222> LOCATION: (55)..(57)
<223> OTHER INFORMATION: n is a, c, g, or t
<220> FEATURE:
<221> NAME/KEY: misc_feature
<222> LOCATION: (73)..(75)
<223> OTHER INFORMATION: n is a, c, g, or t
<220> FEATURE:
<221> NAME/KEY: misc_feature
<222> LOCATION: (91)..(93)
<223> OTHER INFORMATION: n is a, c, g, or t

<400> SEQUENCE: 18
nnnccattgt cacactccnn nccattgtca cactccnnnc cattgtcaca ctccnnncca      60
ttgtcacact ccnnnccatt gtcacactcc nnncctatag tgagtcgtat ta            112

<210> SEQ ID NO 19
<211> LENGTH: 110
<212> TYPE: DNA
<213> ORGANISM: Artificial Sequence
<220> FEATURE:
```

```
<223> OTHER INFORMATION: Synthetic polynucleotide

<400> SEQUENCE: 19
tgttgtgtta cttgtcaaga aagaagcaat gttcttcagt aacagaatga gttggtttat    60
ggggaaaaga gaagagaatc taaaaaataa acaaatccct aacacgtggt              110

<210> SEQ ID NO 20
<211> LENGTH: 110
<212> TYPE: DNA
<213> ORGANISM: Artificial Sequence
<220> FEATURE:
<223> OTHER INFORMATION: Synthetic polynucleotide

<400> SEQUENCE: 20
accacgtgtt agggatttgt ttatttttta gattctcttc tcttttcccc ataaaccaac    60
tcattctgtt actgaagaac attgcttctt tcttgacaag taacacaaca              110

<210> SEQ ID NO 21
<211> LENGTH: 146
<212> TYPE: DNA
<213> ORGANISM: Artificial Sequence
<220> FEATURE:
<223> OTHER INFORMATION: Synthetic polynucleotide

<400> SEQUENCE: 21
attacgttgc acccattgtc acactccatt acgtgcaccc attgtcacac tccattacgt    60
tgcacccatt gtcacactcc attacgttgc acccattgtc acactccatt acgttgcacc  120
cattgtcaca ctccattacg ttgcac                                       146

<210> SEQ ID NO 22
<211> LENGTH: 147
<212> TYPE: DNA
<213> ORGANISM: Artificial Sequence
<220> FEATURE:
<223> OTHER INFORMATION: Synthetic polynucleotide

<400> SEQUENCE: 22
gtgcaacgta atggagtgtg acaatgggtg caacgtaatg gagtgtgaca atgggtgcaa    60
cgtaatggag tgtgacaatg ggtgcaacgt aatggagtgt gacaatgggt gcaacgtaat   120
ggagtgtgac aatgggtgca acgtaat                                       147
```